(12) United States Patent
Bold et al.

(10) Patent No.: US 7,329,660 B2
(45) Date of Patent: **\*Feb. 12, 2008**

(54) PHTHALAZINE DERIVATIVES FOR TREATING INFLAMMATORY DISEASES

(75) Inventors: Guido Bold, Gipf-Oberfrick (CH); Janet D King, Bennwil (CH); Joerg Frei, Hoelstein (CH); Richard Heng, Hegenheim (FR); Paul W Manley, Arlesheim (CH); Bernhard Wietfeld, Efringen-Kirchen (DE); Jeanette M Wood, Biel-Benken (CH)

(73) Assignee: Novartis AG, Basel (CH)

( \* ) Notice: Subject to any disclaimer, the term of this patent is extended or adjusted under 35 U.S.C. 154(b) by 0 days.

This patent is subject to a terminal disclaimer.

(21) Appl. No.: 11/441,961

(22) Filed: May 26, 2006

(65) Prior Publication Data

US 2006/0217388 A1 Sep. 28, 2006

Related U.S. Application Data

(60) Continuation of application No. 11/099,292, filed on Apr. 5, 2005, now abandoned, which is a division of application No. 10/723,238, filed on Nov. 26, 2003, now Pat. No. 6,911,440, which is a division of application No. 09/964,025, filed on Sep. 26, 2001, now Pat. No. 6,686,347, which is a continuation of application No. PCT/EP00/02726, filed on Mar. 28, 2000.

(30) Foreign Application Priority Data

| Mar. 30, 1999 | (CH) | 603/99 |
| Jul. 8, 1999 | (GB) | 9916064.0 |

(51) Int. Cl.
*A01N 43/58* (2006.01)
*A01N 43/60* (2006.01)
*A61K 31/50* (2006.01)
*A61K 31/495* (2006.01)

(52) U.S. Cl. .................................. 514/248
(58) Field of Classification Search ................ None
See application file for complete search history.

(56) References Cited

U.S. PATENT DOCUMENTS

| 2,960,504 A | 11/1960 | Druey et al. ............. 260/450 |
| 4,665,181 A | 5/1987 | Thomas et al. ............ 544/237 |
| 6,514,974 B2 | 2/2003 | Bold et al. ............. 514/252.03 |
| 6,686,347 B2 | 2/2004 | Bold et al. ................. 514/183 |

FOREIGN PATENT DOCUMENTS

| EP | 0 722 936 | 7/1996 |
| GB | 871753 | 6/1961 |
| GB | 1293565 | 10/1972 |
| WO | WO 98/35958 | 8/1998 |

OTHER PUBLICATIONS

Hawley's Condensed Chemical Dictionary © 1997 by Van Nostrand Reinhold, p. 604.\*
"Leukemia: Types" printout from the website "Oncology Channel®" http://www.oncologychannel.com/leukemias/types.shtml (generated Feb. 15, 2007, © 1998-2007).\*
Verstovesek et al, "Prognostic significance of cellular vascular endothelial growth factor expression in chronic phase chronic myeloid leukemia" Blood, vol. 99(6), pp. 2265-2267 (2002).\*
Aguayo et al, "Angiogenesis in acute and chronic leukemias and myelodisplastic syndromes" Blood, vol. 96(6), pp. 2240-2245 (2000).\*
Bold et al, "New Anillinophthalazines as Potent and Orally Well Absorbed Inhibitors of the VEGF Receptor Tyrosine Kinases Useful as Antagonists of Tumor-Driven Angiogenesis" Journal of Medicinal Chemistry, vol. 43(12), pp. 2310-2323 (2000).\*
Hennequin et al., "Design and Structure-Activity Relationship of a New Class of Potent VEGF Receptor Tyrosine Kinase Inhibitors," J. Med. Chem., vol. 42, No. 26, pp. 5369-5389 (1999).
Ishihara H. et al., "Pharmacological Characterization of a novel, potent and selective phosphodiesterase 5 inhibitor, E4010," Jpn. J. Pharmacol, vol. 76, p. 175 (1998).
Watanabe N. et al., "4-benzylamino-1-chloro-6-substituted phthalazines: synthesis and inhibitory activity toward phosphodiesterase 5,j" J. Med. Chem., vol. 41, pp. 3367-3372 (1998).
Hawley's Condensed Chemical Dictionary, 13th ed., p. 604, © 1997 by Van Nostrand Reinhold.

\* cited by examiner

*Primary Examiner*—Zachary C Tucker

(57) ABSTRACT

The invention relates to the treatment of leukemias with an inhibitor of the activity of VEGF receptor tyrosine kinase of the formula I, $$X-(CR_aR_a')_n-Y \quad (I)$$

the substituents being defined in the specification; as well as to new phthalazine derivatives; processes for the preparation thereof; the application thereof in a process for the treatment of the human or animal body; the use thereof for the treatment of a disease, especially a disease caused by ocular neovascularization, such as age-related macula degeneration or diabetic retinopathy, or other diseases that respond to the inhibition of tyrosine kinases, such as a proliferative disease; a method for the treatment of such disease in mammals; and the use of such a compound for the manufacture of a pharmaceutical preparation for the treatment especially of a disease as mentioned above.

4 Claims, No Drawings

PHTHALAZINE DERIVATIVES FOR TREATING INFLAMMATORY DISEASES

This application is a continuation of U.S. patent application Ser. No. 11/099,292 filed Apr. 5, 2005 now abandoned, which is a divisional of U.S. patent application Ser. No. 10/723,238, filed Nov. 26, 2003 now U.S. Pat. No. 6,911,440, which is a divisional of U.S. patent application Ser. No. 09/964,025, filed Sep. 26, 2001 now U.S. Pat. No. 6,686,347, which is a continuation of International Application No. PCT/EP00/02726, filed Mar. 28, 2000, the contents of which are incorporated herein by reference.

The invention relates to a new medical use for phthalazine derivatives, especially for the treatment of inflammatory rheumatic or rheumatoid diseases and/or pain, more especially for the treatment of rheumatoid arthritis and/or pain; as well as to new phthalazine derivatives, processes for the preparation thereof, the application thereof in a process for the treatment of the human or animal body, the use thereof— alone or in combination with one or more other pharmaceutically active compounds—for the treatment of a disease, especially as mentioned above, a disease caused by ocular neovascularisation, such as age-related macula degeneration or diabetic retinopathy, or other diseases that respond to the inhibition of tyrosine kinases, such as a proliferative disease, such as a tumour disease, a method for the treatment of such disease in mammals, especially in humans, and the use of such a compound—alone or in combination with one or more other pharmaceutically active compounds—for the manufacture of a pharmaceutical preparation (medicament) for the treatment especially a disease as mentioned above or of a proliferative disease, such as a tumour disease.

BACKGROUND OF THE INVENTION

Two processes, the de novo formation of vessels from differentiating endothelial cells or angioblasts in the developing embryo (vasculogenesis) and the growth of new capillary vessels from existing blood vessels (angiogenesis), are involved in the development of the vascular systems of animal organs and tissues, as well as in transitory phases of angiogenesis, for example during the menstrual cycle, in pregnancy, or in wound healing. On the other hand, a number of diseases are known to be associated with deregulated angiogenesis, for example diseases caused by ocular neovascularisation, such as retinopathies (including diabetic retinopathy), age-related macula degeneration, psoriasis, haemangioblastoma, haemangioma, an inflammatory disease, such as a rheumatoid or rheumatic inflammatory disease, especially arthritis, such as rheumatoid arthritis, and especially neoplastic diseases, for example so-called solid tumours and liquid tumours (such as leucemias).

Recent findings show that at the centre of the network regulating the growth and differentiation of the vascular system and its components, both during embryonic development and normal growth and in a wide number of pathological anomalies and diseases, lies the angiogenic factor known as "Vascular Endothelial Growth Factor" (=VGEF), along with its cellular receptors (see Breier, G., et al., Trends in Cell Biology 6, 454-6-[1996] and the references cited therein).

VEGF is a dimeric, disulfide-linked 46-kDa glycoprotein and is related to "Platelet-Derived Growth Factor" (PDGF). It is produced by normal cell lines and tumour cell lines, is an endothelial cell-specific mitogen, shows angiogenic activity in in vivo test systems (e.g. rabbit cornea), is chemotactic for endothelial cells and monocytes, and induces plasminogen activators in endothelial cells, which are then involved in the proteolytic degradation of extracellular matrix during the formation of capillaries. A number of isoforms of VEGF are known which show comparable biological activity, but differ in the type cells that secrete them and in their heparin-binding capacity. In addition, there are other members of the VEGF family, such as "Placenta Growth Factor" (PLGF) and VEGF-C.

VEGF receptors, however, are transmembranous receptor tyrosine kinases and have an extracellular domain with seven immunoglobulin-like domains and an intracellular tyrosine kinase domain. Various types are known, e.g. VEGFR-1, VEGFR-2, and VEGFR-3.

A large number of human tumours, especially gliomas and carcinomas, express high levels of VEGF and its receptors. This has led to the hypothesis that the VEGF released by tumour cells could stimulate the growth of blood capillaries and the proliferation of tumour endothelium in a paracrine manner and thus, through the improved blood supply, accelerate tumour growth. Increased VEGF expression could explain the occurrence of cerebral oedema in patients with glioma. Direct evidence of the role of VEGF as a tumour angiogenesis factor in vivo has been obtained from studies in which VEGF expression or VEGF activity was inhibited. This was achieved with antibodies which inhibit VEGF activity, with dominant-negative VEGFR-2 mutants which inhibited signal transduction, or with the use of antisense-VEGF RNA techniques. All approaches led to a reduction in the growth of glioma cell lines or other tumour cell lines in vivo as a result of inhibited tumour angiogenesis.

Hypoxia and also a large number of growth factors and cytokines, e.g. Epidermal Growth Factor, Transforming Growth Factor α, Transforming Growth Factor β, Interleukin 1, and Interleukin 6, induce the expression of VEGF in cell experiments. Angiogenesis is regarded as an absolute prerequisite for those tumours which grow beyond a maximum diameter of about 1-2 mm; up to this limit, oxygen and nutrients may be supplied to the tumour cells by diffusion. Every tumour, regardless of its origin and its cause, is thus dependent on angiogenesis for its growth after it has reached a certain size.

Three principal mechanisms play an important part in the anti-tumour activity of angiogenesis inhibitors: 1) Inhibition of the growth of vessels, especially capillaries, into avascular resting tumours, with the result that there is no net tumour growth owing to the balance that is achieved between apoptosis and proliferation; 2) Prevention of the migration of tumour cells owing to the absence of bloodflow to and from tumours; and 3) Inhibition of endothelial cell proliferation, thus avoiding the paracrine growth-stimulating effect exerted on the surrounding tissue by the endothelial cells which normally line the vessels.

SUMMARY OF THE INVENTION

Surprisingly, it has now been found that phthalazine derivatives of formula I, described hereinafter, have advantageous pharmacological properties and inhibit, for example, the activity of VEGF receptor tyrosine kinase and VEGF-dependent cell proliferation, or the treatment of especially inflammatory rheumatic or rheumatoid diseases, such as rheumatoid arthritis, and/or pain, or the other diseases mentioned above and below.

The compounds of formula I permit, for example, an unexpected new therapeutic approach, especially for diseases in the treatment of which, and also for the prevention of which, an inhibition of angiogenesis and/or of the VEGF receptor tyrosine kinase shows beneficial effects.

FULL DESCRIPTION OF THE INVENTION

In accordance with the present invention it has now surprisingly been found that the compounds of the formula I defined below have use in the treatment of inflammatory rheumatic and rheumatoid diseases, especially of the inflammation, e.g. of inflammatory processes, conditions, events and disease, as well as their sequelae or symptoms, associated with a rheumatic or rheumatoid disease; and/or for the treatment of pain.

The invention relates to the treatment of an inflammatory disease, especially an inflammatory rheumatoid or rheumatic disease, more especially to the treatment of arthritis, preferably rheumatoid arthritis, and/or pain, or (especially in the case of new compounds of the formula I) any other disease mentioned hereinbefore and hereinafter, with a compound of the formula I,

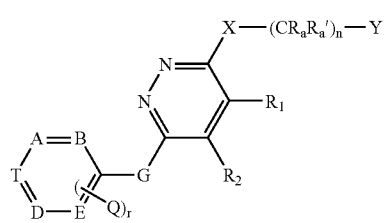

wherein
r is 0 to 2,
n is 0 to 3
$R_1$ and $R_2$
a) are independently in each case a lower alkyl;
b) together form a bridge of subformula I*,

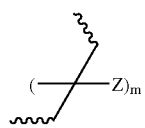

wherein the bond is achieved via the two terminal C atoms and m is 0 to 4, or
c) together form a bridge of subformula I**,

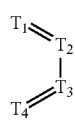

wherein one or two of the ring members $T_1$, $T_2$, $T_3$ and $T_4$ are nitrogen, and the others are in each case CH, and the bond is achieved via atoms $T_1$ and $T_4$;
G is —C(=O)—, —CHF—, —CF$_2$—, lower alkylene, $C_2$-$C_6$alkenylene, lower alkylene or $C_3$-$C_6$alkenylene substituted by acyloxy or hydroxy, —CH$_2$—O—, —CH$_2$—S—, —CH$_2$—NH—, —CH$_2$—O—CH$_2$—, —CH$_2$—S—CH$_2$—, —CH$_2$—NH—CH$_2$—, oxa (—O—), thia (—S—), imino (—NH—), —CH$_2$—O—CH$_2$—, —CH$_2$—S—CH$_2$— or —CH$_2$—NH—CH$_2$—;
A, B, D, E and T are independently N or CH subject to the proviso that at least one and not more than three of these radicals are N;
Q is lower alkyl, lower alkoxy or halogen;
$R_a$ and $R_a'$ are each independently H or lower alkyl;
X is imino, oxa, or thia;
Y is hydrogen, aryl, heteroaryl, or unsubstituted or substituted cycloalkyl; and
Z is mono- or disubstituted amino, halogen, alkyl, substituted alkyl, hydroxy, etherified or esterified hydroxy, nitro, cyano, carboxy, esterified carboxy, alkanoyl, carbamoyl, N-mono- or N,N-disubstituted carbamoyl, amidino, guanidino, mercapto, sulfo, phenylthio, phenyl lower alkylthio, alkylphenylthio, phenylsulfinyl, phenyl-lower alkylsulfinyl, alkylphenylsulfinyl, phenylsulfonyl, phenyl-lower alkylsulfonyl, alkylphenylsulfonyl, or (alternatively or, in a broader aspect of the invention, in addition) selected from the group consisting of ureido, halo-lower alkylthio, halo-lower alkansulfonyl, pyrazolyl, lower-alkyl pyrazolyl and $C_2$-$C_7$alkenyl;
wherein—if more than 1 radical Z (m≧2) is present—the substituents Z are selected independently from each other;
and wherein the bonds characterized in subformula I* by a wavy line are either single or double bonds;
or an N-oxide of said compound, wherein 1 or more N atoms carry an oxygen atom;
or a pharmaceutically acceptable salt thereof, for the treatment of an inflammatory rheumatic or rheumatoid disease and/or pain; preferably
for the manufacture of a pharmaceutical preparation for the treatment of an inflammatory rheumatic or rheumatoid disease and/or pain; a pharmaceutical preparation for the treatment of an inflammatory rheumatic or rheumatoid disease and/or pain comprising said compound or a pharmaceutically acceptable salt thereof and a pharmaceutically acceptable carrier; the use of said compound or pharmaceutically acceptable salt thereof for the treatment of an inflammatory rheumatic or rheumatoid disease and/or pain; or a method of treatment comprising administering said compound of the formula I, or a pharmaceutically acceptable salt thereof, for the treatment of an inflammatory rheumatic or rheumatoid disease and/or pain to a warm-blooded animal in need of such treatment.
or an N-oxide of said compound, wherein 1 or more N atoms carry an oxygen atom;
or a pharmaceutically acceptable salt thereof.

The invention relates especially to the use of a compound of formula I for the manufacture of a pharmaceutical preparation for the treatment of an inflammatory rheumatic or rheumatoid disease and/or pain; a pharmaceutical preparation for the treatment of an inflammatory rheumatic or rheumatoid disease and/or pain comprising said compound or a pharmaceutically acceptable salt thereof and a pharmaceutically acceptable carrier; the use of said compound or pharmaceutically acceptable salt thereof for the treatment of an inflammatory rheumatic or rheumatoid disease and/or pain; or a method of treatment comprising administering said compound of the formula I, or a pharmaceutically acceptable salt thereof, for the treatment of an inflammatory rheumatic or rheumatoid disease and/or pain to a warm-blooded animal in need of such treatment.

The invention also relates to novel compounds of the formula I, especially a compound of formula I

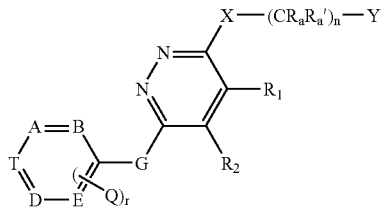

wherein
r is 0 to 2,
n is 0 to 2,
R₁ and R₂
a) are independently in each case a lower alkyl;
b) together form a bridge of subformula I*,
wherein the bond is achieved via the two terminal C atoms and m is 0 to 4, or
c) together form a bridge of subformula I**,
wherein one or two of the ring members T₁, T₂, T₃ and T₄ are nitrogen, and the others are in each case CH, and the bond is achieved via atoms T₁ and T₄;
G represents
i) $C_2$-$C_6$alkenylene, $C_2$-$C_6$alkylene or $C_3$-$C_6$alkenylene substituted by acyloxy or hydroxy, —CH₂—O—, —CH₂—S—, —CH₂—NH—, —CH₂—O—CH₂—, —CH₂—S—CH₂—, —CH₂—NH—CH₂—, oxa (—O—), thia (—S—), imino (—NH—), —C(=O)—, —CHF— or —CF₂—; or
ii) $C_2$-$C_6$alkylene if Q is lower alkyl, or
iii) $C_1$-$C_6$alkylene if Q is lower alkoxy or halogen;
A, B, D, E and T are independently N or CH subject to the proviso that at least one and not more than three of these radicals are N, and that T is only N when α) G is $C_2$-$C_6$alkenylene or $C_3$-$C_6$alkenylene substituted by acyloxy or hydroxy, or β) when Q is lower alkoxy or halogen;
Q is lower alkyl, lower alkoxy or halogen;
$R_a$ and $R_a'$ are each independently H or lower alkyl;
X is imino, oxa, or thia;
Y is hydrogen, aryl, heteroaryl, or unsubstituted or substituted cycloalkyl; and
Z is mono- or disubstituted amino, halogen, alkyl, substituted alkyl, hydroxy, etherified or esterified hydroxy, nitro, cyano, carboxy, esterified carboxy, alkanoyl, carbamoyl, N-mono- or N,N-disubstituted carbamoyl, amidino, guanidino, mercapto, sulfo, phenylthio, phenyl lower alkylthio, alkylphenylthio, phenylsulfinyl, phenyl-lower alkylsulfinyl, alkylphenylsulfinyl, phenylsulfonyl, phenyl-lower alkylsulfonyl, or alkylphenylsulfonyl, wherein—if more than 1 radical Z (m≧2) is present—the substituents Z are selected independently of each other.

and wherein the bonds characterized in subformula I* by a wavy line are either single or double bonds;

or an N-oxide of said compound, wherein 1 or more N atoms carry an oxygen atom;

or a salt thereof.

The invention also relates to a compound of the formula IA (that falls under formula I),

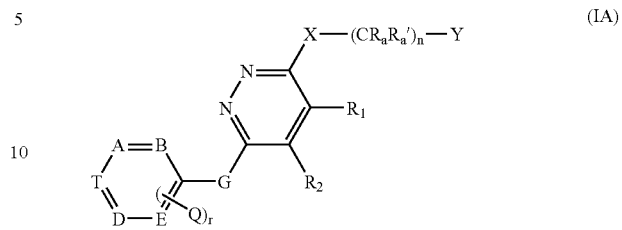

wherein
r is 0 or 1
n is 0 to 3;
R₁ and R₂ together form a bridge as shown in subformula I***,

wherein either each of Z₁ and Z₂ is hydrogen, or one is hydrogen, the other methyl;
the binding being achieved via the two terminal CH groups in subformula I*** and to the two adjacent carbon atoms binding R₁ and R₂ in formula IA, so that a six-membered ring is formed;
A, B, D and E are CH and T is N;
Q is lower alkyl;
G is lower alkylene, hydroxy-methylene (—CH(OH)—), —CHF—, —CF₂— or —C(=O)—;
each of $R_a$ and $R_a'$ is hydrogen;
X is imino;
Y is phenyl that is substituted by one or more, especially on to three, more specifically 1 or 2 substituents selected from the group consisting of lower alkyl, especially methyl, ethyl, n-propyl or isopropyl; ureido; lower alkoxy, especially methoxy; halogen-lower alkylthio, especially trifluormethylthio; halo-lower alkansulfonyl, especially trifluormethylsulfonyl; pyrazolyl or lower-alkylpyrazolyl, especially pyrazol-3-yl or 1-methyl-pyrazol-3-yl; N-lower-alkyl-carbamoyl, especially N-tert-butyl-carbamoyl; hydroxy; lower alkoxycarbonyl, especially methoxycarbonyl or tert-butoxycarbonyl; $C_2$-$C_7$-alkenyl, especially vinyl; halo, especially fluoro, chloro, bromo or iodo; halo-lower alkyl, especially trifluoromethyl or 2,2,2-trifluoroethyl; and sulfamoyl;
or is naphthyl; quinolyl, especially quinolin-6-yl; lower alkyl-pyridinyl, especially 5-methyl-pyridin-2-yl or 6-methyl-pyridin-2-yl; lower alkylpyrimidinyl, especially 4-methylpyrimidin-2-yl or 6-tert-butyl-pyrimidin-4-yl; halo-lower alkylpyridyl, especially 5-trifluoromethyl-pyridin2-yl; lower alkoxy-pyridyl, especially 5-methoxy-pyridin-2-yl; di-lower alkyl-pyridyl, especially 2,6-dimethyl-pyridin-4-yl or 4,6-dimethyl-pyridin-2-yl; di-lower alkylpyrimidinyl, especially 2,6-dimethyl-pyrimidin-4-yl; or halo-pyridyl, especially 5-bromo-pyridin-2-yl or 6-chloro-pyridin-3-yl;

or is cyclohexyl substituted with lower alkyl, especially 4-tert-butyl-cyclohexyl;

or an N-oxide thereof, wherein 1 or more nitrogen atoms carry an oxygen atom;

or a salt thereof; or especially the use of a compound in the treatment of a rheumatoid or rheumatic inflammatory disease and/or pain.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Any asymmetric carbon atoms (for example in compounds of formula I [or an N-oxide thereof], wherein n=1 and R is lower alkyl) may be present in the (R)-, (S)- or (R,S)-configuration, preferably in the (R)- or (S)-configuration. Substituents at a double bond or a ring may be present in cis- (=Z-) or trans (=E-) form. The compounds may thus be present as mixtures of isomers or as pure isomers, preferably as enantiomer-pure diastereomers.

The present invention relates also to possible tautomers of the compounds of formula I.

"Treatment" (or "use in the treatment") as used herein includes, if not mentioned otherwise, use for the alleviation, amelioration or control of inflammation, especially of inflammatory rheumatic or rheumatoid disease, process, condition or event, and/or of pain. It also includes intervention for the alleviation, amelioration or control of the sequelae or symptoms of such inflammation, for example degeneration (e.g. of cells, synovium or tissues), or especially swelling, exudation or effusion, or pain. In this context the term "treatment" is further to be understood as embracing use to reverse, restrict or control progression of any specified disease, process, condition, event or the like, including use for disease modifying effect. If any of the mentioned diseases, processes, conditions or events is associated with pain, the term "treatment" preferably encompasses the alleviation, amelioration or control (including temporal or permanent removal) of at least one further sequela or symptom in addition to pain, such as swelling, effusion, exudation or degeneration, more preferably of all symptoms and most preferably of the total clinical picture of the respective disease, irritation or manifestation.

The compounds of the formula I are in particular applicable to the treatment of: an inflammatory rheumatoid or rheumatic disease, especially of manifestations at the locomotor apparatus, such as various inflammatory rheumatoid diseases, especially (1) chronic polyarthritis (=rheumatoid arthritis (very preferred)), including juvenile arthritis or psoriasis arthropathy;

(2) paraneoplastic syndrome or tumor-induced inflammatory diseases, (3) turbid effusions, (4) collagenosis, such as systemic Lupus erythematosus, poly-myositis, dermato-myositis, systemic sclerodermia or mixed collagenosis;

(5) postinfectious arthritis (where no living pathogenic organism can be found at or in the affected part of the body), or (6) seronegative spondylarthritis, such as spondylitis ankylosans; or further (7) vasculitis, (8) sarcoidosis, or (9) arthrosis;

or further any combinations thereof.

An example of a preferred inflammation to be treated is
(a) synovial inflammation, for example, synovitis, including any of the particular forms of synovitis recited in Dorland's Illustrated Medical Dictionary, 26th edition, pub. W. B. Saunders and Co. at page 1301, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans.

The present invention is further applicable to the systemic treatment of:
b) Inflammation, e.g. inflammatory diseases or conditions, of the joints or locomotor apparatus in the region of the tendon insertions and tendon sheaths.

Such inflammation may be, for example, be consequential to or associated with disease or further (in a broader sense of the invention) with surgical intervention, e.g. as recited under a) above, including, in particular conditions such as insertion endopathy, myofasciale syndrome and tendomyosis.

The present invention is further especially applicable to the treatment of:
c) Inflammation, e.g. inflammatory disease or condition, of connective tissues.

Such diseases or conditions include in particular dermatomyositis and myositis.

From the foregoing it will be understood that the present invention is to be further understood as embracing the treatment, e.g. therapy, of any disease or condition as set forth above, for example rheumatoid arthritis, arthroses, dermatomyositis etc., for example, for the alleviation or control of inflammatory processes or events and the sequelae associated therewith or consequential thereto, e.g. for the treatment of rheumatoid arthritis, e.g. to alleviate or control joint inflammation or effusion.

In the case of the inflammatory diseases, diseases where a living pathogen, e.g. a virus, a bacterium, a fungus, a protozoon or a parasite or the like, is still present, the treatment of should first aim at removal of the pathogen causative for the disease, before treatment with a compound of the formula I or a salt thereof is used, as otherwise there is the danger that the causative pathogen remains intact. Then the mere treatment with a compound of the formula I, or a salt thereof, may be contraindicated in order to avoid survival or even further spread of the causative infection. This is also valid in the case of combination with an anti-inflammatory glucocorticosteroid as described in the following.

In a further aspect it has been found in accordance with the present invention that systemic administration of a compound of the formula 1, or a salt thereof, is useful as replacement therapy for anti-inflammatory glucocorticosteroid, e.g. cortisone or the like, therapy. For example for use in any means of treatment as hereinbefore set forth.

The term "treatment", if not otherwise defined, thus also refers specifically to I. A method of treating rheumatic or rheumatoid inflammation and/or pain, for example treating any process, condition, event, or disease as hereinbefore set forth, in a subject in need thereof, which method comprises administering an effective amount of a compound of the formula I, or a pharmaceutically acceptable salt thereof to a person in need of such treatment;

II. A method of providing replacement therapy for anti-inflammatory glucocorticosteroid therapy in a subject receiving such glucocorticosteroid therapy, for example for or in the treatment of a rheumatic or rheumatoid inflammatory disease and/or pain, especially any process, condition, event or disease as hereinbefore set forth, which process comprises systemicalls administering to said subject an effective amount, e.g. an anti-inflammatory glucocorticosteroid sparing amount, of a compound of the formula I, or a pharmaceutically acceptable salt thereof;

III. A method of treating an inflammatory rheumatoid or rheumatic disease and/or pain, for example treating any process, condition, event or disease as hereinbefore set forth, in a subject in need thereof, which method comprises systemically administering an effective amount of a compound of the formula I, or a pharmaceutically acceptable salt thereof, together with an anti-inflammatory glucocorticosteroid.

Where co-administration is practiced as under III above the drug substances, i.e. a compound of the formula I and an anti-inflammatory glucocorticosteroid may be administered sequentially or simultaneously or substantially simultaneously, e.g. employing a fixed combination dosage form.

In further aspects the present invention, when the term "treatment" is used, also provides, if not defined otherwise:

IV. A compound of the formula I, or a pharmaceutically acceptable salt thereof, for use in, or for use in the manufacture of a pharmaceutical composition for use in; or the use of a pharmaceutical composition comprising a compound of the formula I, or a pharmaceutically acceptable salt thereof, for use:
  a) in the treatment of an inflammatory rheumatoid or rheumatic disease and/or pain, for example any inflammatory process, condition, event or disease as hereinbefore set forth and/or pain;
  b) as replacement therapy for anti-inflammatory glucocorticosteroid therapy in the treatment of an inflammatory rheumatoid or rheumatic disease and/or pain, for example in the treatment of any inflammatory process, condition, event or disease as hereinbefore set forth, and/or of pain; or
  c) for co-administration together with an anti-inflammatory glucocorticosteroid in the treatment of an inflammatory rheumatic or rheumatoid disease and/or pain, for example in the treatment of any inflammatory process, condition, event or disease as hereinbefore set forth, and/or of pain; as well as V. A pharmaceutical dosage form for systemic administration comprising a compound of the formula I, or a pharmaceutically acceptable salt thereof, together with an anti-inflammatory glucocorticosteroid.

The index r in formula I is preferably 0 or 1.

The index n in formula I is preferably 0 or 1, or it is 2 or 3.

In the preferred embodiment, $R_1$ and $R_2$ together form a bridge in subformula I*. The index m is preferably 0, 1 or 2. In particular, m is preferably 0 or 1, most especially 0.

In subformula I**, the ring member $T_2$ or $T_3$ is preferably nitrogen, and each of the other ring members are CH.

Of ring members A, B, D, E and T in formula I, not more than 3 may be N, and the remainder are CH. For the case of a novel compound of the formula I, in the preferred embodiment, one of the ring members A or B, especially ring member A, is N, and the remainder are CH.

If G is a bivalent group —$CH_2$—O—, —$CH_2$—S—, or —$CH_2$—NH—, the methylene group in each case is bound to the ring with ring members A, B, D, and E, whereas the heteroatom (O, S, or NH) is bound to the phthalazine ring in formula I.

Lower alkylene (in formula I and IA), $C_2$-$C_6$alkylene and $C_2$-$C_6$alkenylene G may be branched or preferably unbranched and are in particular methylene (where lower alkylene is encompassed) or $C_2$-$C_4$alkylene or $C_2$-$C_4$alkenylene, above all ethylene (—$CH_2$—$CH_2$—), ethenylene, (—CH=CH—), propenylene (—CH=CH—$CH_2$—), propylene (—$CH_2$—$CH_2$—$CH_2$—) or tetramethylene (—$CH_2$—$CH_2$—$CH_2$—$CH_2$—). G is preferably in particular methylene or (especially in novel compounds of the formula I) ethylene, ethenylene or propylene. In $C_2$-$C_6$alkenylene G, the substituents on the double bond are preferably present in the E- (=trans-) form.

Acyl in lower alkylene, especially $C_2$-$C_6$alkylene, or $C_3$-$C_6$alkenylene, substituted by acyloxy is preferably arylcarbonyloxy, wherein aryl is as defined below, in particular benzoyloxy, or lower alkanoyloxy, especially benzoyloxy; in novel compounds of the formula I, $C_2$-$C_6$alkylene substituted by acyloxy is in particular ethylene substituted by benzoyloxy, while in the other compounds of formula I to be used for the treatment of an inflammatory rheumatoid or rheumatic disease and/or pain, methylene substituted by benzoyloxy is especially preferred.

Lower alkylene substituted by hydroxy is especially hydroxymethylene; $C_2$-$C_6$alkylene substituted by hydroxy is preferably hydroxyethylene ($CH_2$—CH(OH)).

Lower alkyl is especially $C_1$-$C_4$alkyl, e.g. n-butyl, sec-butyl, tert-butyl, n-propyl, isopropyl, or especially methyl or also ethyl.

Aryl is preferably an aromatic radical having 6 to 14 carbon atoms, especially phenyl, naphthyl, fluorenyl or phenanthrenyl, the radicals defined above being unsubstituted or substituted by one or more, preferably up to three, especially one or two substituents, especially selected from the group consisting of amino, mono- or disubstituted amino, halogen, alkyl, substituted alkyl, hydroxy, etherified or esterified hydroxy, nitro, cyano,-carboxy, esterified carboxy, alkanoyl, carbamoyl, N-mono- or N,N-disubstituted carbamoyl, especially N-methylcarbamoyl or N-tert-butylcarbamoyl; amidino, guanidino, mercapto, sulfo, phenylthio, phenyl-lower alkylthio, alkylphenylthio, phenylsulfinyl, phenyl-lower alkylsulfinyl, alkylphenylsulfinyl, phenylsulfonyl, phenyl-lower alkylsulfonyl, lower alkenyl, such as ethenyl, phenyl, lower alkylthio, such as methylthio, lower alkanoyl, such as acetyl, lower alkylmercapto, such as methylmercapto (—S—$CH_3$), halogen-lower alkylmercapto, such as trifluoromethylmercapto (—S—$CF_3$), lower alkylsulfonyl, halogen-lower alkylsulfonyl, such as especially trifluoromethane sulfonyl, dihydroxybora (—B(OH)$_2$), heterocyclyl, and lower alkylene dioxy bound at adjacent C-atoms of the ring, such as methylene dioxy; or further or alternatively selected from the group consisting of ureido and sulfamoyl; for example, aryl is phenyl, which is either unsubstituted or substituted by one or two substituents selected independently of one another from the group consisting of amino; lower alkanoylamino, especially acetylamino; halogen, especially fluorine, chlorine, bromine, or iodine; lower alkyl, especially methyl or also ethyl, propyl, or t-butyl; halogen-lower alkyl, especially trifluoromethyl; hydroxy; lower alkoxy, especially methoxy or also ethoxy; phenyl-lower alkoxy, especially benzyloxy; and cyano, or (as an alternative or in addition to the previous group of substituents) $C_8$-$C_{12}$alkoxy, especially n-decyloxy, carbamoyl, lower alkylcarbamoyl, such as n-methyl- or n-tert-butylcarbamoyl, lower alkanoyl, such as acetyl, phenyloxy, halogen-lower alkyloxy, such as trifluoromethoxy or 1,1,2,2-tetrafluoroethyloxy, lower alkoxycarbonyl, such as methoxy-, tert- butoxy- or ethoxycarbonyl, lower alkylmercapto, such as methylmercapto, halogen-lower alkylmercapto, such as trifluoromethylmercapto, hydroxy-lower alkyl, such as hydroxymethyl or 1-hydroxymethyl, lower alkylsulfonyl, such as methane sulfonyl, halogen-lower alkylsulfonyl, such as trifluoromethane sulfonyl, phenylsulfonyl, dihydroxybora (—B(OH)$_2$), 2-methyl-pyrimidin-4-yl, oxazol-5-yl, 2-methyl-1,3-dioxolan-2-yl, 1H-pyrazol-3-yl, 1-methyl-pyrazol-3-yl and lower alkylenedioxy bound to two adjacent C-atoms, such as methylene dioxy or, alternatively or in addition to the previous group of substituents, ureido, vinyl, pyrazol-3-yl and 1-methyl-pyrazol-3-yl, especially preferred are (especially with regard to a novel compound of the formula I as described hereinbefore and hereinafter) one or two substituents independently selected from lower alkyl, especially methyl, halogen, especially chlorine or bromine, and halogen lower alkyl, especially trifluoromethyl. In the cases where Y is aryl, it is in particular preferred that aryl is phenyl preferably substituted by one or two substituents independently selected from the group consisting of lower alkyl, in particular methyl, ethyl, n-propyl, i-propyl or t-butyl; halogen, in particular fluorine, chlorine, bromine or iodine; lower alkoxy, in particular ethoxy; and halogen lower alkyl, in particular trifluoromethyl; special preference being for substitution by one or two substitutents independently selected from the group consisting of lower alkyl, in particular methyl or t-butyl; halogen, in particular chlorine; and halogen lower alkyl, in particular trifluoromethyl; or that (especially in a novel compound of the formula I) aryl is napthyl, especially 2-naphthyl.

Heteroaryl is preferably a heterocyclic radical unsaturated in the bonding ring and is preferably monocyclic or in a broader sense bicyclic or tricyclic; wherein at least in the ring bonding to the radical of the molecule of formula I one or more, preferably one to four, especially one or two carbon atoms of a corresponding aryl radical are substituted by a heteroatom selected from the group consisting of nitrogen, oxygen and sulfur, the bonding ring preferably having 4 to 12, especially 5 to 7 ring atoms; heteroaryl being unsubstituted or substituted by one or more, especially 1 to 3, independently selected from the group consisting of the substituents defined above as substituents of aryl; and especially being a heteroaryl radical selected from the group consisting of imidazolyl, thienyl, furyl, pyranyl, thianthrenyl, isobenzofuranyl, benzofuranyl, chromenyl, 2H-pyrrolyl, pyrrolyl, lower alkyl-substituted imidazolyl, benzimidazolyl, pyrazolyl, thiazolyl, isothiazolyl, oxazolyl, isoxazolyl, pyridyl, pyrazinyl, pyrimidinyl, pyridazinyl, indolizinyl, isoindolyl, 3H-indolyl, indolyl, indazolyl, triazolyl, tetrazolyl, purinyl, 4H-quinolizinyl, isoquinolyl, quinolyl, phthalazinyl, naphthyridinyl, quinoxalyl, quinazolinyl, cinnolinyl, pteridinyl, carbazolyl, phenanthridinyl, acridinyl, perimidinyl, phenanthrolinyl and furazanyl, each of these radicals being bonded to at least one heteroatom and the radical of the molecule of formula I via a ring and each of these radicals being unsubstituted or (in case of a novel compound of the formula IA preferably) substituted by one to two radicals selected from the group consisting of lower alkyl, especially methyl or tert-butyl, lower alkoxy, especially methoxy, and halo, especially bromo or chloro; pyridyl is especially preferred; also especially preferred (especially in the case of a novel compound of the formula IA) are quinolyl, especially quinolin-6-yl; lower alkyl-pyridyl, especially 5-methyl-pyridin-2-yl or 6-methyl-pyridin-2-yl; lower alkylpyrimidinyl, especially 4-methylpyrimidin-2-yl or 6-tert-butyl-pyrimidin-4-yl; halo-lower alkylpyridyl, especially 5-trifluoromethyl-pyridin2-yl; lower alkoxy-pyridyl, especially 5-methoxy-pyridin-2-yl; di-lower alkyl-pyridyl, especially 2,6-dimethyl-pyridin-4-yl or 4,6-dimethyl-pyridin-2-yl; di-lower alkylpyrimidinyl, especially 2,6-dimethyl-pyrimidin-4-yl; or halo-pyridyl, especially 5-bromo-pyridin-2-yl or 6-chloro-pyridin-3-yl.Pyridyl Y is preferably 3- or 4-pyridyl.

Mono- or disubstituted amino is especially amino substituted by one or two radicals selected independently of one another from lower alkyl, such as methyl; hydroxy-lower alkyl, such as 2-hydroxyethyl; phenyl-lower alkyl; lower alkanoyl, such as acetyl; benzoyl; substituted benzoyl, wherein the phenyl radical is unsubstituted or especially substituted by one or more, preferably one or two, substituents selected from nitro or amino, or also from halogen, amino, N-lower alkylamino, N,N-di-lower alkylamino, hydroxy, cyano, carboxy, lower alkoxycarbonyl, lower alkanoyl, and carbamoyl; and phenyl-lower alkoxycarbonyl, wherein-the phenyl radical is unsubstituted or especially substituted by one or more, preferably one or two, substituents selected from nitro or amino, or also from halogen, amino, N-lower alkylamino, N,N-di-lower alkylamino, hydroxy, cyano, carboxy, lower alkoxycarbonyl, lower alkanoyl, and carbamoyl; and is preferably N-lower alkylamino, such as N-methylamino, hydroxy-lower alkylamino, such as 2-hydroxyethylamino, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, or a substituent selected from the group consisting of benzoylamino and phenyl-lower alkoxycarbonylamino, wherein the phenyl radical in each case is unsubstituted or especially substituted by nitro or amino, or also by halogen, amino, N-lower alkylamino, N,N-di-lower alkylamino, hydroxy, cyano, carboxy, lower alkoxycarbonyl, lower alkanoyl or carbamoyl, or as an alternative or in addition to the previous group of radicals by aminocarbonylamino.

Halo or halogen is above all fluorine, chlorine, bromine, or iodine, especially fluorine, chlorine, or bromine.

Alkyl has preferably up to a maximum of 12 carbon atoms and is especially lower alkyl, especially methyl, or also ethyl, n-propyl, isopropyl, or tert-butyl.

Substituted alkyl is alkyl as last defined, especially lower alkyl, preferably methyl; where one or more, especially up to three, substituents may be present, primarily from the group selected from halogen, especially fluorine, and also from amino, N-lower alkylamino, N,N-di-lower alkylamino, N-lower alkanoylamino, hydroxy, cyano, carboxy, lower alkoxycarbonyl, and phenyl-lower alkoxycarbonyl. Trifluoromethyl is especially preferred. In a novel compound of the formula I, methyl is especially preferred.

Etherified hydroxy is especially $C_8$-$C_{20}$alkyloxy, such as n-decyloxy, lower alkoxy (preferred), such as methoxy, ethoxy, isopropyloxy, or n-pentyloxy, phenyl-lower alkoxy, such as benzyloxy, or also phenyloxy, or as an alternative or in addition to the previous group halogen-lower alkyloxy, such as trifluoromethyloxy or 1,1,2,2-tetrafluoroethoxy.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxycarbonyloxy.

Esterified carboxy is especially lower alkoxycarbonyl, such as tert-butoxycarbonyl or ethoxycarbonyl, or further methoxycarbonyl, phenyl-lower alkoxycarbonyl, or phenyloxycarbonyl.

Alkanoyl is above all alkylcarbonyl, especially lower alkanoyl, e.g. acetyl.

N-mono- or N,N-disubstituted carbamoyl is especially substituted by one or two substituents selected from the group consisting of lower alkyl, especially methyl, phenyl-lower alkyl, or hydroxy-lower alkyl, at the terminal nitrogen atom.

Alkylphenylthio is especially lower alkylphenylthio.

Alkylphenylsulfinyl is especially lower alkylphenylsulfinyl.

Halo-lower alkylthio is preferably trifluormethylthio.

Halo-lower alkansulfonyl is preferably trifluormethylsulfonyl.

Pyrazolyl is preferably pyrazol-3-yl, lower alkylpyrazolyl is preferably 1-methyl-pyrazol-3-yl.

$C_2$-$C_7$-Alkenyl is preferably vinyl.

Unsubstituted or substituted cycloalkyl is preferably $C_3$-$C_8$cycloalkyl, which is unsubstituted or substituted in the same way as aryl, especially as defined for phenyl. Cyclohexyl and in the broader sense cyclopentyl or cyclopropyl are preferred.

Z in a novel compound of the formula I is preferably amino, hydroxy-lower alkylamino, such as 2-hydroxyethylamino, lower alkanoylamino, such as acetylamino, nitrobenzoylamino, such as 3-nitrobenzoylamino, aminobenzoylamino, such as 4-aminobenzoylamino, phenyl-lower alkoxycarbonylamino, such as benzyloxycarbonylamino, or halogen, such as bromine; preferably only one substituent is present (m=1), especially one of the last mentioned, especially halogen. A compound of formula I wherein $R_1$ and $R_2$ together form a bridge of the subformula I*, especially a compound of the formula IA wherein Z is absent (m=0), is quite especially preferred.

Heterocyclyl is especially a five or six-membered heterocyclic system with 1 or 2 heteroatoms selected from the group consisting of nitrogen, oxygen, and sulfur, which may be unsaturated or wholly or partly saturated, and is unsubstituted or substituted, especially by lower alkyl, such as methyl; a radical selected from 2-methylpyrimidin-4-yl, oxazol-5-yl, 2-methyl-1,3-dioxolan-2-yl, 1H-pyrazol-3-yl, and 1-methyl-pyrazol-3-yl is preferred.

Aryl in the form of phenyl which is substituted by lower alkylene dioxy bound to two adjacent C-atoms, such as methylene dioxy, is preferably 3,4-methylene dioxyphenyl.

The bonds in subformula I* characterized by wavy lines are present either as single or as double bonds. Preferably both are at the same time either single or double bonds. It is especially preferred when both are double bonds at the same time.

The bridges formed from $R_1$ and $R_2$ in formula I and formula IA which are of subformula I*, I or I* form, together with the carbon atoms bonding $R_1$ and $R_2$, a ring with 6 ring atoms.

An N-oxide of a compound of formula I or IA is preferably an N-oxide in which a phthalazine-ring nitrogen or a nitrogen in the ring with ring members A, B, D, and E carries an oxygen atom, or several of said nitrogen atoms carry an oxygen atom.

Salts are especially the pharmaceutically acceptable salts of compounds of formula I or IA (or an N-oxide thereof).

Such salts are formed, for example, as acid addition salts, preferably with organic or inorganic acids, from compounds of formula I or IA (or an N-oxide thereof) with a basic nitrogen atom, especially the pharmaceutically acceptable salts. Suitable inorganic acids are, for example, halogen acids, such as hydrochloric acid; sulfuric acid; or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, 2-hydroxybutyric acid, gluconic acid, glucosemonocarboxylic acid, fumaric acid, succinic acid, adipic-acid, pimelic acid, suberic acid, azelaic acid, malic acid, tartaric acid, citric acid, glucaric acid, galactaric acid, amino acids, such as glutamic acid, aspartic acid, N-methylglycine, acetylaminoacetic acid, N-acetylasparagine or N-acetylcysteine, pyruvic acid, acetoacetic acid, phosphoserine, 2- or 3-glycerophosphoric acid, maleic acid, hydroxymaleic acid, methylmaleic acid, cyclohexanecarboxylic acid, benzoic acid, salicylic acid, 1- or 3-hydroxynaphthyl-2-carboxylic acid, 3,4,5-trimethoxybenzoic acid, 2-phenoxybenzoic acid, 2-acetoxybenzoic acid, 4-aminosalicylic acid, phthalic acid, phenylacetic acid, glucuronic acid, galacturonic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalenedisulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline. earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

In the presence of a basic group and an acid group in the same molecule, a compound of formula I or IA (or an N-oxide thereof) may also form internal salts.

For isolation or purification purposes it is also possible to use pharmaceutically unacceptable salts, for example picrates or perchlorates. Only the pharmaceutically acceptable salts or free compounds (if the occasion arises, in the form of pharmaceutical preparations) attain therapeutic use, and these are therefore preferred.

In view of the close relationship between the novel compounds in free form and in the form of their salts, including those salts that can be used as intermediates, for example in the purification or identification of the novel compounds, any reference hereinbefore and hereinafter to the free compounds is to be understood as referring also to the corresponding salts, as appropriate and expedient.

The compounds of formula I and of formula IA (or an N-oxide thereof) have valuable pharmacological properties, as described hereinbefore and hereinafter.

The efficacy of the compounds of the formula I, especially the novel compounds and the compounds of formula IA, as inhibitors of VEGF-receptor tyrosine kinase activity can be demonstrated as follows:

Test for activity against VEGF-receptor tyrosine kinase: the test is conducted using Flt-1 VEGF-receptor tyrosine kinase. The detailed procedure is as follows: 30 μl kinase solution (10 ng of the kinase domain of Flt-1, Shibuya et al., Oncogene 5, 519-24 [1990]) in 20 mM Tris•HCl pH 7.6, 3 mM manganese dichloride (MnCl$_2$), 3 mM magnesium chloride (MgCl$_2$) and 3 µg/ml poly(Glu,Tyr) 4:1 (Sigma, Buchs, Switzerland), 8 µM [$^{33}$P]-ATP (0.2 µCi/batch), 1% dimethyl sulfoxide, and 0 to 50 µM of the compound to be tested are incubated together for 15 minutes at room temperature. The reaction is then ended by the addition of 10 µl 0.25 M ethylenediaminetetraacetate (EDTA) pH 7. Using a multichannel dispenser (LAB SYSTEMS, USA), an aliquot of 20 µl is applied to a PVDF (=polyvinyl difluoride) Immobilon P membrane (Millipore, USA), which is incorporated into a Millipore microtitre filter manifold, and connected to a vacuum. Following complete elimination of the liquid, the membrane is washed 4 times successively in a bath containing 0.5% phosphoric acid (H$_3$PO$_4$), incubated for 10 minutes each time while shaking, then mounted in a Hewlett Packard TopCount Manifold and the radioactivity measured after the addition of 10 µl Microscint® (β-scintillation counter liquid; Packard USA). IC$_{50}$-values are determined by linear regression analysis of the percentages for the inhibition of each compound in three concentrations (as a rule 0.01, 0.1, and 1 µM). Preferably inhibitory concentrations (IC$_{50}$ with 50% maximum inhibition versus control without inhibitory substance of formula I) in the range 10 nmol/litre to 100 µmol/litre are found here, especially in the range 10 to 2000 nmol/litre.

The antitumour efficacy of the compounds of formula I, especially the novel compounds of formula I or of the formula IA, can be demonstrated in vivo as follows:

In vivo activity in the nude mouse xenotransplant model: female BALB/c nude mice (8-12 weeks old, for example Novartis Animal Farm, Sisseln, Switzerland) are kept under sterile conditions with water and feed ad libitum. Tumours are induced by subcutaneous injection of tumour cells (human epithelial cell line A-431; American Type Culture Collection (ATCC), Rockville, Md., USA, Catalogue Number ATCC CRL 1555; cell line from an 85-year-old woman; epidermoid carcinoma cell line) into carrier mice. The resulting tumours pass through at least three consecutive transplantations before the start of treatment. Tumour fragments (about 25 mg) are implanted subcutaneously in the left flank of the animals using a 13-gauge trocar needle under Forene® anaesthesia (Abbott, Switzerland). Treatment with the test compound is started as soon as the tumour has reached a mean volume of 100 mm$^3$. Tumour growth is measured two to three times a week and 24 hours after the last treatment by determining the length of two perpendicular axes. The tumour volumes are calculated in accordance with published methods (see Evans et al., Brit. J. Cancer 45, 466-8 [1982]). The antitumour efficacy is determined as the mean increase in tumour volume of the treated animals divided by the mean increase in tumour volume of the untreated animals (controls) and, after multiplication by 100, is expressed as T/C%. Tumour regression (given in %) is reported as the smallest mean tumour volume in relation to the mean tumour volume at the start of treatment. The test compound is administered daily by gavage.

As an alternative to cell line A-431, other cell lines may also be used in the same manner, for example:

the MCF-7 breast adenocarcinoma cell line (ATCC No. HTB 22; see also J. Natl. Cancer Inst. (Bethesda) 51, 1409-16 [1973]);

the MDA-MB 468 breast adenocarcinoma cell line (ATCC No. HTB 132; see also In Vitro 14,911-15 [1978]);

the MDA-MB 231 breast adenocarcinoma cell line (ATCC No. HTB 26; see also J. Natl. Cancer Inst. (Bethesda) 53, 661-74 [1974]);

the Colo 205 colon carcinoma cell line (ATCC No. CCL 222; see also Cancer Res. 38, 1345-55 [1978]);

the HCT 116 colon carcinoma cell line (ATCC No. CCL 247; see also Cancer Res. 41, 1751-6 [1981]);

the DU145 prostate carcinoma cell line DU 145 (ATCC No. HTB 81; see also Cancer Res. 37, 4049-58 [1978]); and the PC-3 prostate carcinoma cell line PC-3 (ATCC No. CRL 1435; see also Cancer Res. 40, 524-34 [1980]).

In vivo tumor inhibition can be observed e.g. at 50 mg/kg in mice.

The inhibition of VEGF-induced KDR-receptor autophosphorylation can be confirmed with a further in vitro experiment in cells: transfected CHO cells, which permanently express human VEGF receptor (KDR), are seeded in culture medium (with 10% fetal calf serum=FCS) in 6-well cell-culture plates and incubated at 37° C. under 5% CO$_2$ until they show about 80% confluency. The compounds to be tested are then diluted in culture medium (without FCS, with 0.1% bovine serum albumin) and added to the cells. (Controls comprise medium without test compounds). After two hours' incubation at 37° C., recombinant VEGF is added; the final VEGF concentration is 20 ng/ml). After a further five minutes' incubation at 37° C., the cells are washed twice with ice-cold PBS (phosphate-buffered saline) and immediately lysed in 100 µl lysis buffer per well. The lysates are then centrifuged to remove the cell nuclei, and the protein concentrations of the supernatants are determined using a commercial protein assay (BIORAD). The lysates can then either be immediately used or, if necessary, stored at −20° C.

A sandwich ELISA is carried out to measure the KDR-receptor phosphorylation: a monoclonal antibody to KDR (for example Mab 1495.12.14; prepared by H. Towbin) is immobilized on black ELISA plates (OptiPlate™ HTRF-96 from Packard). The plates are then washed and the remaining free protein-binding sites are saturated with 1% BSA in PBS. The cell lysates (20 µg protein per well) are then incubated overnight at 4° C. with an antiphosphotyrosine antibody coupled with alkaline phosphatase (PY20:AP from Transduction Laboratories). The binding of the antiphosphotyrosine antibody is then demonstrated using a luminescent AP substrate (CDP-Star, ready to use, with Emerald II; TROPIX). The luminescence is measured in a Packard Top Count Microplate Scintillation Counter (Top Count). The difference between the signal of the positive control (stimulated with VEGF) and that of the negative control (not stimulated with VEGF) corresponds to VEGF-induced KDR-receptor phosphorylation (=100%). The activity of the tested substances is calculated as % inhibition of VEGF-induced KDR-receptor phosphorylation, wherein the concentration of substance that induces half the maximum inhibition is defined as the ED50 (effective dose for 50% inhibition). Compounds of formula I here preferably show ED50 values in the range of 1 nM to 20 µM, preferably 1 nM to 500 nM.

Compounds of formula I or IA, or N-oxides thereof, inhibit to varying degrees also other tyrosine kinases involved in signal transduction which are mediated by trophic factors, for example Abl kinase, kinases from the Src family, especially c-Src kinase, Lck, and Fyn; or in a broader sense kinases of the EGF family, for example, c-erbB2 kinase (HER-2), c-erbB3 kinase, c-erbB4 kinase; insulin-like growth factor receptor kinase (IGF-1 kinase), especially members of the PDGF-receptor tyrosine kinase family, such as PDGF-receptor kinase, CSF-1-receptor kinase, Kit-receptor kinase and VEGF-receptor kinase, especially KDR and Flk, and the angiopoetin 1 and 2 receptor Tek; or in a broader sense also serine/threonine kinases, all of which play a role in growth regulation and transformation in mammalian cells, including human cells. The respective assays can be done utilizing the respective tyrosine kinase expressed as GST-fusion protein using the baculovirus system. The respective kinases are purified via a glutathione-Sepharose column and utilized to determine the $IC_{50}$s for the compounds.

The inhibition of c-erbB2 tyrosine kinase (HER-2) can be measured, for example, in the same way as the inhibition of EGF-R protein kinase (see House et al., Europ. J. Biochem. 140, 363-7 [1984]). The erbB2 kinase can be isolated, and its activity determined, using methods known per se (see Akiyama et al., Science 232, 1644 [1986]).

In particular, an inhibitory effect-can also be found on PDGF-receptor kinase, which is determined according to the method described by Trinks et al. (see J. Med. Chem. 37(7): 1015-27 [1994]).

The usefulness of a compound of the formula I in the treatment of arthritis as an example of an inflammatory rheumatic or rheumatoid disease can be demonstrated as follows:

The well-known rat adjuvant arthritis model (Pearson, Proc. Soc. Exp. Biol. 91, 95-101 (1956)) is used to test the anti-arthritic activity of compounds of the formula I, or salts thereof. Adjuvant Arthritis can be treated uwing two different dosing schedules: either (i) starting time of immunisation with adjuvant (prophylactic dosing); or from day 15 when the arthritic response is already established (therapeutic dosing). Preferably a therapeutic dosing schedule is used. For comparison, e.g. SDZ115-155 (=DUP697) is administered in a separate group.

In detail, male Wistar rats (5 animals per group, weighing epproximately 200 g, supplied by Iffa Credo, France) are injected i.d. (intra-dermally) at the base of the tail with 0.1 ml of mineral oil containing 0.6 mg of lyophilised heat-killed *Mycobacterium tuberculosis*. The rats are treated with the test compound (3, 10 or 30 mg/kg p.o. once per day), or vehicle (water) from day 15 to day 22 (therapeutic dosing schedule). At the end of the experiment, the swelling of the tarsal joints is measured by means of a mico-calliper. Percentage inhibition of paw swelling is calculated by reference to vehicle treated arthritic animals (0% inhibition) and vehicle treated normal animals (100% inhibition).

A compound of the formula I if administered at a 30 mg/kg dose here preferably shows activity in the range of 20 to 100%, more prefeably 25 to 90% inhibition.

The activity of compounds of the formula I against pain can be shown in the following model of nociception (pain). In this model, the hyperalgesia caused by an intra-planar yeast injection is measured by applying increased pressure to the foot until the animal vocalizes or withdraws its foot from the applied pressure pad. The model is sensitive to COX inhibitors, and diclofenac at 3 mg/kg is used as a positive control.

Method: The baseline pressure required to induce vocalization or withdrawal of the paw of male Sprague Dawley rats (weighing approximately 180 g, supplied by Iffa Credo, France) is measured (2 hours before treatment), followed by an intra-planar injection of 100 µl of a 20% yeast suspension in water in the hind paw. The rats are treated orally with the test compound (3, 10 or 30 mg/kg), diclofenac (3 mg/kg) or vehicle (saline) p.o. 2 hours later (time point 0 hours), and the pressure test is repeated 1 and 2 hours after dosing. Using the standard apparatus supplied by Ugo Basile, Italy, the pressure required to induce vocalisation or paw withdrawal of the compound-treated rats at these time points is compared to that of vehicle-treated animals.

A test compound of the formula I inhibits paw hyperalgesia both at 1 and 2 hours after dosing in the Randall-Selitto test preferably at the 30 mg/kg p.o. dose, preferably by 10 to 100%, demonstrating that the compound has analgesic activity.

On the basis of these studies, a compound of formula I surprisingly is appropriate for the treatment of inflammatory (especially rheumatic or rheumatoid) diseases and/or pain. The compounds of the formula I, especially IA, (or an N-oxide thereof) according to the invention also show therapeutic efficacy especially against other disorders dependent on protein kinase, especially proliferative diseases.

On the basis of their efficacy as inhibitors of VEGF-receptor tyrosine kinase activity, the compounds of the formula I, especially the novel compounds of the formula IA, primarily inhibit the growth of blood vessels and-are thus, for example, effective against a number of diseases associated with deregulated angiogenesis, especially diseases caused by ocular neovascularisation, especially retinopathies, such as diabetic retinopathy or age-related macula degeneration, psoriasis, haemangioblastoma, such as haemangioma, mesangial cell proliferative disorders, such as chronic or acute renal diseases, e.g. diabetic nephropathy, malignant nephrosclerosis, thrombotic microangiopathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atheroma, arterial restenosis, autoimmune diseases, acute inflammation, fibrotic disorders (e.g. hepatic cirrhosis), diabetes, neurodegenerative disorders and especially neoplastic diseases (solid tumours, but also leucemias and other "liquid tumours", especially those expressing c-kit, KDR or fit-1), such as especially breast cancer, cancer of the colon, lung cancer (especially small-cell lung cancer), cancer of the prostate or Kaposi's sarcoma. A compound of formula I (or an N-oxide thereof) inhibits the growth of tumours and is especially suited to preventing the metastatic spread of tumours and the growth of micrometastases.

A compound of formula I, especially IA, (or an N-oxide thereof) can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. In particular, a compound of formula I, especially IA, (or an N-oxide thereof) can besides or in addition be administered for example in the case of tumour therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumour regression, or even chemopreventive therapy, for example in patients at risk.

Therapeutic agents for possible combination are especially one or more antiproliferative, cytostatic or cytotoxic compounds, for example a chemotherapeutic agent or several selected from the group consisting of an inhibitor of polyamine biosynthesis, an inhibitor of protein kinase, especially of serine/threonine protein kinase, such as protein kinase C, or of tyrosine protein kinase, such as epidermal growth factor receptor tyrosine kinase, a cytokine, a negative growth regulator, such as TGF-β or IFN-β, an aromatase inhibitor and a classical cytostatic agent.

Other combination partners are mentioned above under the term "treatment".

A compound according to the invention is not only for the (prophylactic and preferably therapeutic) management of humans, but also for the treatment of other warm-blooded animals, for example of commercially useful animals, for example rodents, such as mice, rabbits or rats, or guinea-pigs. Such a compound may also be used as a reference standard in the test systems described above to permit a comparison with other compounds.

In general, the invention relates also to the use of a compound of formula IA (or an N-oxide thereof) for the inhibition of VEGF-receptor tyrosine kinase activity.

A compound of formula I, especially IA, (or an N-oxide thereof) may also be used for diagnostic purposes, for example with tumours that have been obtained from warm-blooded animal "hosts", especially humans, and implanted into mice to test them for decreases in growth after treatment with such a compound, in order to investigate their sensitivity to said compound and thus to improve the detection and determination of possible therapeutic methods for neoplastic diseases in the original host.

With the groups of preferred compounds of formula I, especially IA, mentioned hereinafter, definitions of substituents from the general definitions mentioned hereinbefore may reasonably be used, for example, to replace more general definitions with more specific definitions or especially with definitions characterized as being preferred; in each case, the definitions described hereinbefore as being preferred or exemplary are preferred.

For use in the treatment of an inflammatory rheumatic or rheumatoid disease, especially rheumatoid arthritis, and/or pain, especially the compounds of formula I mentioned in PCT application WO 98/35958 are to be included into the present invention; WO 98/35958 is therefore included by reference.

Especially preferred is the use in the treatment of a rheumatic or rheumatoid inflammatory disease, especially rheumatoid arthritis, and/or pain, especially as defined in more-detail hereinbefore and hereinafter, of a compound of the formula I wherein
r is 0 to 2,
n is 0 to 3
$R_1$ and $R_2$
a) are independently in each case a lower alkyl;
b) together form a bridge of subformula I*,
wherein the bond is achieved via the two terminal C atoms and m is 0 to 4, or
c) together form a bridge of subformula I**,
wherein one or two of the ring members $T_1$, $T_2$, $T_3$ and $T_4$ are nitrogen, and the others are in each case CH, and the bond is achieved via atoms $T_1$ and $T_4$;
G is —C(=O)—, —CHF—, —CF$_2$—, lower alkylene, $C_2$-$C_6$alkenylene, lower alkylene or $C_3$-$C_6$alkenylene substituted by acyloxy or hydroxy, —CH$_2$—O—, —CH$_2$—S—, —CH$_2$—NH—, —CH$_2$—O—CH$_2$—, —CH$_2$—S—CH$_2$—, —CH$_2$—NH—CH$_2$—, oxa (—O—), thia (—S—), imino (—NH—), —CH$_2$—O—CH$_2$—, —CH$_2$—S—CH$_2$— or —CH$_2$—NH—CH$_2$—;
A, B, D, E and T are independently N or CH subject to the proviso that at least one and not more than three of these radicals are N;
Q is lower alkyl, especially methyl;
$R_a$ and $R_a'$ are each independently H or lower alkyl;
X is imino, oxa, or thia;
Y is hydrogen, aryl, heteroaryl, or unsubstituted or substituted cycloalkyl; and
Z is mono- or disubstituted amino, halogen, alkyl, substituted alkyl, hydroxy, etherified or esterified hydroxy, nitro, cyano, carboxy, esterified carboxy, alkanoyl, carbamoyl, N-mono- or N,N-disubstituted carbamoyl, amidino, guanidino, mercapto, sulfo, phenylthio, phenyl lower alkylthio, alkylphenylthio, phenylsulfinyl, phenyl-lower alkylsulfinyl, alkylphenylsulfinyl, phenylsulfonyl, phenyl-lower alkylsulfonyl, alkylphenylsulfonyl, or (alternatively or, in a broader aspect of the invention, in addition) selected from the group consisting of ureido, halo-lower alkylthio, halo-lower alkansulfonyl, pyrazolyl, lower-alkyl pyrazolyl and $C_2$-$C_7$alkenyl;

wherein—if more than 1 radical Z (m≧2) is present—the substituents Z are selected independently from each other;

and wherein the bonds characterized in subformula I* by a wavy line are either single or double bonds;

or an N-oxide of the defined compound, wherein 1 or more N atoms carry an oxygen atom.

More preferred is the use in the treatment of an inflammatory rheumatic or rheumatoid disease, especially rheumatoid arthritis, and/or pain of a compound falling under formula I wherein
r is 0 to 2,
n is 0 to 2,
m is 0 to 4,
$R_1$ and $R_2$ (i) are lower alkyl, especially methyl, or
(ii) together form a bridge in subformula I*,
the binding being achieved via the two terminal carbon atoms, or
(iii) together form a bridge in subformula I**, wherein one or two of the ring members $T_1$, $T_2$, $T_3$ and $T_4$ are nitrogen, and the others are in each case CH, and the binding is achieved via $T_1$ and $T_4$;
A, B, D, and E are, independently of one another, N or CH, with the stipulation that not more than 2 of these radicals are N;
T is nitrogen;
G is lower alkylene, lower alkylene substituted by acyloxy or hydroxy, —CH$_2$—O—, —CH$_2$—S—, —CH$_2$—NH—, oxa (—O—), thia (—S—), or imino (—NH—);
Q is lower alkyl, especially methyl;
R is H or lower alkyl;
X is imino, oxa, or thia;
Y is aryl, pyridyl, or unsubstituted or substituted cycloalkyl; and
Z is mono- or disubstituted amino, halogen, alkyl, substituted alkyl, hydroxy, etherified or esterified hydroxy, nitro, cyano, carboxy, esterified carboxy, alkanoyl, carbamoyl, N-mono- or N,N-disubstituted carbamoyl, amidino, guanidino, mercapto, sulfo, phenylthio, phenyl lower alkylthio, alkylphenylthio, phenylsulfinyl, phenyl-lower alkylsulfinyl, alkylphenylsulfinyl, phenylsulfonyl, phenyl-lower alkylsulfonyl, or alkylphenylsulfonyl, wherein—if more than 1 radical Z (m=≧2) is present— the substituents Z are are selected independently from one another;

and wherein the bonds characterized, if present, by a wavy line are either single or double bonds;

or an N-oxide of the defined compound, wherein 1 or more N atoms carry an oxygen atom;

preferably with the stipulation that, if Y is pyridyl or unsubstituted cycloalkyl, X is imino, and the remaining radicals are as defined, G is selected from the group comprising lower alkylene, —CH$_2$—O—, —CH$_2$—S—, oxa and thia;

or of a pharmaceutically acceptable salt thereof.

This class of compounds, its synthesis and other uses are known from PCT application WO 98/35958, which is incorporated herewith by reference.

Even more preferred is the use in the treatment of an inflammatory rheumatic or rheumatoid disease, especially rheumatoid arthritis, and/or pain of a compound falling under formula I that is preferred in WO 98/35958.

Most preferably, for use in the treatment of a rheumatic or rheumatoid inflammatory disease, especially rheumatoid arthritis, and/or pain, a compound selected from the group consisting of the following compounds, or a pharmaceutically acceptable salt thereof, is chosen:

1-(4-Chloroanilino)-4-(4-pyridylmethyl)phthalazine (especially the succinate salt thereof);

[4-(4-chloroanilino)phthalazin-1-yl](pyridin-4-yl)methanol (Example 78 in WO 98/35958); and 1-(4-chloroanilino) 4-[(1-oxypyridin-4-yl)methyl]phthalazine (Example 65 in WO 98/35958).

The invention relates also to novel compounds of the formula I, especially of the formula IA.

A compound of the formula I is preferred wherein wherein r is 0 to 2, n is 0 to 2, R$_1$ and R$_2$ a) are independently in each case a lower alkyl;

b) together form a bridge of subformula I*, wherein the bond is achieved via the two terminal C atoms and m is 0 to 4, or c) together form a bridge of subformula I**, wherein one or two of the ring members T$_1$, T$_2$, T$_3$ and T$_4$ are nitrogen, and the others are in each case CH, and the bond is achieved via atoms T$_1$ and T$_4$;

G represents i) C$_2$-C$_6$alkylene, C$_2$-C$_6$alkylene or C$_3$-C$_6$alkenylene substituted by acyloxy or hydroxy, —CH$_2$—O—, —CH$_2$—S—, —CH$_2$—NH—, —CH$_2$—O—CH$_2$—, —CH$_2$—S—CH$_2$—, —CH$_2$—NH—CH$_2$—, oxa (—O—), thia (—S—), imino (—NH—), —C(=O)—, —CHF— or —CF$_2$—; or ii) C$_2$-C$_6$alkylene if Q is lower alkyl, or iii) C$_1$-C$_6$alkylene if Q is lower alkoxy or halogen;

A, B, D, E and T are independently N or CH subject to the proviso that at least one and not more than three of these radicals are N, and that T is only N when α) G is C$_2$-C$_6$alkenylene or C$_3$-C$_6$alkenylene substituted by acyloxy or hydroxy, or β) when Q is lower alkoxy or halogen;

Q is lower alkyl, lower alkoxy or halogen;

R$_a$ and R$_a$' are each independently H or lower alkyl;

X is imino, oxa, or thia;

Y is hydrogen, aryl, heteroaryl, or unsubstituted or substituted cycloalkyl; and Z is mono- or disubstituted amino, halogen, alkyl, substituted alkyl, hydroxy, etherified or esterified hydroxy, nitro, cyano, carboxy, esterified carboxy, alkanoyl, carbamoyl, N-mono- or N,N-disubstituted carbamoyl, amidino, guanidino, mercapto, sulfo, phenylthio, phenyl lower alkylthio, alkylphenylthio, phenylsulfinyl, phenyl lower alkylsulfinyl, alkylphenylsulfinyl, phenylsulfonyl, phenyl-lower alkylsulfonyl, or alkylphenylsulfonyl, wherein—if more than 1 radical Z (m≧2) is present—the substituents Z are selected independently of each other and wherein the bonds characterized in subformula I* by a wavy line are either single or double bonds;

or an N-oxide of said compound, wherein 1 or more N atoms carry an oxygen atom;

or a salt thereof.

More preferred is a compound of the formula I is preferred wherein r is 0 to 2, n is 0 to 2, R$_1$ and R$_2$ together form a bridge in subformula I*, m is 0 to 4, G is C$_2$-C$_6$alkylene, C$_2$-C$_6$alkenylene, C$_2$-C$_6$alkylene hydroxy or C$_3$-C$_6$alkenylene substituted by acyloxy or, —CH$_2$—O—, —CH$_2$—S—, —CH$_2$—NH—, oxa (—O—), thia (—S—) or imino (—NH—); or, in addition to the group of moieties mentioned so far or alternatively, is —C(=O)—, —CHF— or —CF$_2$—;

A, B, D, E and T are independently N or CH subject to the proviso that at least one and not more than three of these radicals are N, and that T is only N when G is C$_2$-C$_6$alkenylene or is C$_3$-C$_6$alkenylene substituted by acyloxy or hydroxy;

Q is lower alkyl;

R$_a$ and R$_a$' are each independently H or lower alkyl;

X is imino, oxa, or thia;

Y is hydrogen, aryl, heteroaryl, or unsubstituted or substituted cycloalkyl; and Z is mono- or disubstituted amino, halogen, alkyl, substituted alkyl, hydroxy, etherified or esterified hydroxy, nitro, cyano, carboxy, esterified carboxy, alkanoyl, carbamoyl, N-mono- or N,N-disubstituted carbamoyl, amidino, guanidino, mercapto, sulfo, phenylthio, phenyl-lower alkylthio, alkylphenylthio, phenylsulfinyl, phenyl-lower alkylsulfinyl, alkylphenylsulfinyl, phenylsulfonyl, phenyl-lower alkylsulfonyl, or alkylphenylsulfonyl, wherein—if more than 1 radical Z (m≧2) is present—the substituents Z are selected independently from one another;

and wherein the bonds characterized by a wavy line are either single or double bonds;

or an N-oxide of the defined compound, wherein 1 or more N atoms carry an oxygen atom;

or a salt thereof.

Preference is also for a compound of formula I wherein r is 0 to 2, n is 0 to 2, R$_1$ and R$_1$ together form a bridge in subformula I*, m is 0 to 4, G is C$_2$-C$_6$alkylene, C$_2$-C$_6$alkenylene, C$_2$-C$_6$alkylene substituted by acyloxy or hydroxy or C$_3$-C$_6$alkenylene, —CH$_2$—O—, —CH$_2$—S—, —CH$_2$—NH—, oxa (—O—), thia (—S—) or imino (—NH—);

A, B, D, and E are, independently of one another, N or CH, subject to the proviso that not more than 2 of these radicals are N, and T is CH;

Q is is lower alkyl;

R$_a$ and R$_a$' are each independently H or lower alkyl;

X is imino, oxa, or thia;

Y is aryl, heteroaryl, or unsubstituted or substituted cycloalkyl; and

Z is amino, mono- or disubstituted amino, halogen, alkyl, substituted alkyl, hydroxy, etherified or esterified hydroxy, nitro, cyano, carboxy, esterified carboxy, alkanoyl, carbamoyl, N-mono- or N,N-disubstituted carbamoyl, amidino, guanidino, mercapto, sulfo, phenylthio, phenyl-lower alkylthio, alkylphenylthio, phenylsulfinyl, phenyl-lower alkylsulfinyl, alkylphenylsulfinyl, phenylsulfonyl, phenyl-lower alkylsulfonyl, or alkylphenylsulfonyl, wherein—if more than 1 radical Z (m≧2) is present—the substituents Z are selected independently from one another;

and wherein the bonds characterized by a wavy line are either single or double bonds;

or an N-oxide of the defined compound, wherein 1 or more N atoms carry an oxygen atom;

or a salt thereof.

Likewise preferred is a compound of formula I wherein
r is 0 or 1,
n is 0 or 1,
$R_1$ and $R_2$ together form a bridge in subformula I*,
m is 0 or 1,
B, E, D and T are each CH and A is N;
G is $C_2$-$C_6$alkylene or $C_2$-$C_6$alkenylene;
Q is methyl;
$R_a$ and $R_a'$ are each independently H or lower alkyl;
X is imino, oxa, or thia,
Y is phenyl, which is unsubstituted or is substituted independently by one or two substituents from the group consisting of amino; lower alkanoylamino; halogen, lower alkyl; halogen-lower alkyl; lower alkoxy; phenyl-lower alkoxy; cyano; lower alkenyl, $C_8$-$C_{12}$alkoxy, lower alkoxycarbonyl, carbamoyl, lower alkylcarbamoyl, lower alkanoyl, phenyloxy, halogen-lower alkyloxy, lower alkoxycarbonyl, lower alkylmercapto, halogen-lower alkylmercapto, hydroxy-lower alkyl, lower alkylsulfonyl, halogen-lower alkylsulfonyl, phenylsulfonyl, dihydroxybora, 2-methylpyrimidin-4-yl, oxazol-5-yl, 2-methyl-1,3-dioxolan-2-yl, 1H-pyrazol-3-yl, 1-methylpyrazol-3-yl, and lower alkylenedioxy bound to two adjacent C atoms;
Z is amino; N-lower alkylamino; hydroxy-lower alkylamino; phenyl-lower alkylamino; N,N-di-lower alkylamino; n-phenyl-lower alkyl-N-lower alkylamino; N,N-di-lower alkylphenylamino; lower alkanoylamino; or a substituent from the group consisting of benzoylamino and phenyl-lower alkoxycarbonylamino, wherein the phenyl radical in each case is unsubstituted or substituted by nitro, halogen, amino, N-lower alkylamino, N,N-di-lower alkylamino, hydroxy, cyano, carboxy, lower alkoxycarbonyl, lower alkanoyl or carbamoyl; or is halogen; and the bonds characterized by a wavy line are in each case a double bond or in each case also a single bond;

or a salt thereof.

In addition a compound of formula I is preferred wherein
r is 0 or 1,
n is 0 or 1,
$R_1$ and $R_2$ together form a bridge in subformula I*,
m is 0;
B, E, D and T are each CH and A is N;
G is $C_2$-$C_6$alkylene or $C_2$-$C_6$alkenylene;
Q is methyl;
$R_a$ and $R_a'$ are each independently H or lower alkyl;
X is imino, oxa, or thia,
Y is phenyl, which is unsubstituted or is substituted independently by one or two substituents from the group consisting of amino; lower alkanoylamino, halogen, lower alkyl; halogen-lower alkyl, lower alkoxy, phenyl-lower alkoxy, cyano, lower alkenyl, $C_8$-$C_{12}$alkoxy, lower alkoxycarbonyl, carbamoyl, lower alkylcarbamoyl, lower alkanoyl, phenyloxy, halogen-lower alkyloxy, lower alkoxycarbonyl, lower alkylmercapto, halogen-lower alkylmercapto, hydroxy-lower alkyl, lower alkylsulfonyl, halogen-lower alkylsulfonyl, phenylsulfonyl, dihydroxybora, 2-methylpyrimidin-4-yl, oxazol-5-yl, 2-methyl-1,3-dioxolan-2-yl, 1H-pyrazol-3-yl, 1-methylpyrazol-3-yl, and lower alkylenedioxy bound to two adjacent C atoms; and the bonds characterized by a wavy line are in each case a double bond or in each case also a single bond;

or a salt thereof.

Special preference is given to a compound of formula I wherein
r is 0;
n is 0;
$R_1$ and $R_2$ together form a bridge in subformula I*,
m is 0;
B, D and E are each CH and A or T is in each case N;
G is ethylene, propylene or ethenylene;
$R_a$ and $R_a'$ are each independently H or lower alkyl;
X is imino,
Y is phenyl, which is unsubstituted or substituted by one or two substituents selected independently from the group consisting of halogen; lower alkyl; and halogen-lower alkyl; and
the bonds characterized by a wavy line are double bonds;

or a salt thereof.

A further especially preferred embodiment of the invention relates to compounds in which
r is 0;
n is 0;
$R_1$ and $R_2$ together form a bridge in subformula I*,
m is 0;
G is ethylene, propylene or ethenylene;
A is N and B, D, E and T are CH;
$R_a$ and $R_a'$ are each independently H or lower alkyl;
X is imino;
Y is phenyl, which is unsubstituted or substituted by one or two substituents selected independently from the group consisting of lower alkyl, halogen, and trifluoromethyl;
and the bonds characterized by a wavy line are either single or double bonds;

or an N-oxide of said compound, wherein one or more N atoms carry an oxygen atom;

or a salt thereof.

The invention also relates to a compound of the formula IA shown above (that falls under formula I), wherein
r is 0 to 2, especially 0 or 1;
n is 0 to 3;
$R_1$ and $R_2$ together form a bridge as shown in subformula I***,

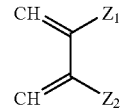

(I***)

wherein either each of $Z_1$ and $Z_2$ is hydrogen, or one is hydrogen, the other methyl;

the binding being achieved via the two terminal CH groups in subformula I*** and to the two adjacent carbon atoms binding $R_1$ and $R_2$ in formula IA, so that a six-membered ring is formed;

A, B, D and E are CH and T is N,

Q is methyl (preferably bound to A and/or D);

G is —C(=O)—, —CHF— or —CF$_2$—;

each of $R_a$ and $R_a'$ is hydrogen;

X is imino;

Y is 4-chlorophenyl, 4-tert-butyl-phenyl, 3,5-dimethyl-phenyl, 2-methyl-6-ethyl-phenyl, 3-isopropyl-5-methyl-phenyl, 3-ureido-phenyl, 3-chloro-4-methoxy-phenyl, 4-chloro-3-methoxy-phenyl, 3-methoxy-4-methyl-phenyl, 3-methoxy-4-ethyl-phenyl, 3-(trifluoro-methylthio)-phenyl, 6-chloro-3-(trifluoromethylsulfonyl)-phenyl, 3-(N-methylcarbamoyl)-phenyl, 4-(N-tert-butylcarbamoyl)-phenyl, 3-(pyrazol-3-yl)-phenyl, 3-([1-methyl-pyrazol]-3-yl)-phenyl, 4-(tert-butoxycarbonyl)-phenyl, 3,5-bis(methoxycarbonyl)-phenyl, 3-vinyl-phenyl, 3,4- or 3,5-bis(trifluoromethyl)-phenyl, 3-chloro-4-methyl-phenyl, 3-bromo-4-methyl-phenyl, 3-bromo-4-ethyl-phenyl, 4-bromo-3-isopropyl-phenyl, 4-bromo-3-n-propyl-phenyl, 3-iodo-4-methylphenyl, 4-iodo-3-isopropyl-phenyl, 4-fluoro-3-trifluoromethyl-phenyl, 3-chloro-5-trifluoromethyl-phenyl, 4-chloro-3-trifluoromethyl-phenyl, 3-bromo-5-trifluoromethyl-phenyl, 4-bromo-3-trifluoromethyl-phenyl, 4-iodo-3-trifluormethyl-phenyl, 3-bromo-5-(2,2,2-trifluoroethyl)-phenyl, 3-iodo-5-trifluoromethyl-phenyl, 3-methyl-5-trifluoromethylphenyl or 4-sulfamoyl-phenyl, or (especially if n is other than 0) is 4-methylphenyl, 3-methylphenyl, 4-ethyl-phenyl, 3-ethyl-phenyl, 2-methylphenyl, 3- or 4-trifluoromethyl-phenyl, 2-chlorophenyl, 3-chlorophenyl or 3-fluoro-5-trifluoromethyl-phenyl, or is 2-naphthyl; quinolin-6-yl; 5-methyl-pyridin-2-yl; 6-methyl-pyridin-2-yl; 4-methylpyrimidin-2-yl; 6-tert-butyl-pyrimidin-4-yl; 5-trifluoromethyl-pyridin2-yl; 5-methoxy-pyridin-2-yl; 2,6-dimethyl-pyridin-4-yl or 4,6-dimethyl-pyridin-2-yl; 2,6-dimethyl-pyrimidin-4-yl; 5-bromo-pyridin-2-yl or 6-chloro-pyridin-3-yl;

or is 4-tertbutylcyclohexyl;

or an N-oxide thereof, wherein 1 or more nitrogen atoms carry an oxygen atom;

or a salt thereof.

The invention also relates to a compound of the formula IA shown above (that falls under formula I), wherein r is 0 to 2, especially 0 or 1;

n is 0 to 3;

$R_1$ and $R_2$ together form a bridge as shown in subformula I***, wherein either each of $Z_1$ and $Z_2$ is hydrogen, or one is hydrogen, the other methyl;

the binding being achieved via the two terminal CH groups in subformula I*** and to the two adjacent carbon atoms binding $R_1$ and $R_2$ in formula IA, so that a six-membered ring is formed;

A, B, D and E are CH and T is N,

Q is methyl (preferably bound to A and/or D);

G is methylene or hydroxymethylene;

each of $R_a$ and $R_a'$ is hydrogen;

X is imino;

Y is 3-isopropyl-5-methyl-phenyl, 4-chloro-3-methoxy-phenyl, 3,4-bis(trifluoromethyl)-phenyl, 3-chloro-4-methyl-phenyl, 3-bromo-4-methyl-phenyl, 3-bromo-4-ethyl-phenyl, 4-bromo-3-isopropyl-phenyl, 4-bromo-3-n-propyl-phenyl, 3-iodo-4-methylphenyl, 4-iodo-3-isopropyl-phenyl, 4-fluoro-3-trifluoromethyl-phenyl, 3-chloro-5-trifluoromethyl-phenyl, 4-bromo-3-trifluoromethyl-phenyl, 4-iodo-3-trifluormethyl-phenyl, 3-bromo-5-(2,2,2-trifluoroethyl)-phenyl, 3-iodo-5-trifluoromethyl-phenyl, 3-methyl-5-trifluoromethylphenyl or 4-sulfamoylphenyl, or (if n is other than 0) is 4-methylphenyl, 3-methylphenyl, 4-ethyl-phenyl, 3-ethyl-phenyl, 2-methylphenyl, 3- or 4-trifluoromethyl-phenyl, 2-chlorophenyl, 3-chlorophenyl, 4-chlorophenyl, 4-chloro-3-trifluoromethyl-phenyl, 3-bromo-5-trifluoromethyl-phenyl or 3-fluoro-5-trifluoromethyl-phenyl, or is 2-naphthyl; quinolin-6-yl; 5-methyl-pyridin-2-yl; 6-methyl-pyridin-2-yl; 4-methylpyrimidin-2-yl; 6-tert-butyl-pyrimidin-4-yl; 5-trifluoromethyl-pyridin-2-yl; 5-methoxy-pyridin-2-yl; 2,6-dimethyl-pyridin-4-yl or 4,6-dimethyl-pyridin-2-yl; 2,6-dimethyl-pyrimidin-4-yl; 5-bromo-pyridin-2-yl or 6-chloro-pyridin-3-yl;

or is 4-tertbutylcyclohexyl;

or an N-oxide thereof, wherein 1 or more nitrogen atoms carry an oxygen atom;

or a salt thereof.

Most special preference is given to a compound of the formula IA as described above, where the compound is selected from the group consisting of the following compounds, or a pharmaceutically acceptable salt thereof:

1-(3-Bromo-4-methyl-anilino)-4-(pyridin-4-yl-methyl)-phthalazine (see example 13h below);

[4-(4-chloroanilino)phthalazin-1-yl]-(pyridin-4-yl)ketone; and

[4-(4-chloroanilino)phthalazin-1-yl]-(1-oxypyridin-4-yl) methanol.

Special preference is also given to a compound of the formula IA, wherein r is 0;

n is 0;

$R_1$ and $R_2$ together form a bridge as shown in subformula I***, wherein one of $Z_1$ and $Z_2$ is hydrogen, the other methyl;

the binding being achieved via the two terminal CH groups in subformula I*** and to the two adjacent carbon atoms binding $R_1$ and $R_2$ in formula IA, so that a six-membered ring is formed;

A, B, D and E are CH and T is N,

G is methylene;

X is imino; and

Y is 4-chlorophenyl, 4-chloro-3-methoxy-phenyl, 3-iodo-4-methyl-phenyl, 4-chloro-3-trifluoro-methyl-phenyl, 3-bromo-5-trifluoromethyl-phenyl or 4-bromo-3-trifluoromethyl-phenyl;

or an N-oxide thereof, wherein 1 or more nitrogen atoms carry an oxygen atom;

or a salt thereof.

Special preference is also given to a compound of the formula IA, wherein r is 1;

n is 0;

R₁ and R₂ together form a bridge as shown in subformula I***, wherein each of Z₁ and Z₂ is hydrogen;

the binding being achieved via the two terminal CH groups in subformula I*** and to the two adjacent carbon atoms binding R₁ and R₂ in formula IA, so that a six-membered ring is formed;

A, B, D and E are CH and T is N,

G is methylene;

X is imino; and

Y is 4-chloro-3-trifluoromethyl-phenyl, 3-chloro-5-trifluoromethylphenyl, 4-tert-butylphenyl, 3-bromo-4-methylphenyl, 3-bromo-4-ethylphenyl or 4,5-bis(trifluoromethyl)-phenyl;

or an N-oxide thereof, wherein 1 or more nitrogen atoms carry an oxygen atom;

or a salt thereof.

One preferred embodiment of the invention is represented by a compound of formula I wherein r is 0 or 1, n is 0 or 1, R₁ and R₂ together form a bridge in subformula I*, m is 0 or 1, G represents i) C₂-C₆alkenylene, C₂-C₆alkylene or C₃-C₆alkenylene substituted by acyloxy or hydroxy, —CH₂—O—, —CH₂—S—, —CH₂—NH—, —CH₂—O—CH₂—, —CH₂—S—CH₂—, —CH₂—NH—CH₂—, oxa (—O—), thia (—S—), imino (—NH—), —C(=O)—, —CHF— or —CF₂—; or ii) C₂-C₆alkylene if Q is lower alkyl, or iii) C₁-C₆alkylene if Q is lower alkoxy or halogen;

A, B, D, E and T are independently N or CH subject to the proviso that at least one and not more than three of these radicals are N, and that T is only N when α) G is C₂-C₆alkenylene or C₃-C₆alkenylene substituted by acyloxy or hydroxy, or β) when Q is lower alkoxy or halogen;

Q is lower alkyl, lower alkoxy or halogen;

R_a and R_a' are each independently H or lower alkyl;

X is imino, oxa, or thia,

Y is phenyl, which is unsubstituted or is substituted independently by one or two substituents from the group consisting of amino; lower alkanoylamino, halogen, lower alkyl, halogen-lower alkyl, lower alkoxy, phenyl-lower alkoxy, cyano, lower alkenyl, C₈-C₁₂alkoxy, lower alkoxycarbonyl, carbamoyl, lower alkylcarbamoyl, lower alkanoyl, phenyloxy, halogen-lower alkyloxy, lower alkoxycarbonyl, lower alkylmercapto, halogen-lower alkylmercapto, hydroxy-lower alkyl, lower alkylsulfonyl, halogen-lower alkylsulfonyl, phenylsulfonyl, dihydroxybora, 2-methylpyrimidin-4-yl, oxazol-5-yl, 2-methyl-1,3-dioxolan-2-yl, 1H-pyrazol-3-yl, 1-methylpyrazol-3-yl, and lower alkylenedioxy bound to two adjacent C atoms;

Z is amino; N-lower alkylamino; hydroxy-lower alkylamino; phenyl-lower alkylamino; N,N-di-lower alkylamino; n-phenyl-lower alkyl-N-lower alkylamino; N,N-di-lower alkylphenylamino; lower alkanoylamino; or a substituent from the group consisting of benzoylamino and phenyl-lower alkoxycarbonylamino, wherein the phenyl radical in each case is unsubstituted or substituted by nitro, halogen, amino, N-lower alkylamino, N,N-di-lower alkylamino, hydroxy, cyano, carboxy, lower alkoxycarbonyl, lower alkanoyl or carbamoyl; or is halogen; and, the bonds characterized by a wavy line in each case represent a double bond or in the broader sense also a single bond;

or a salt thereof.

Another preferred embodiment of the invention is represented by a compound of formula I wherein r is 1;

n is 0;

R₁ and R₂ together form a bridge in subformula I*, m is 0;

G is methylene;

T is N and A, B, D, and E are CH;

Q is lower alkoxy or halogen;

X is imino;

Y is phenyl, which is substituted by one or two substituents selected independently from the group consisting of lower alkyl; lower alkoxy; halogen; and trifluoromethyl; and the bonds characterized by a wavy line are double bonds;

or an N-oxide of said compound, wherein one or more N atoms carry an oxygen atom;

or a salt thereof.

Special preference is for a compound of formula I, such as is mentioned in the Examples below, or a pharmaceutically acceptable salt thereof, especially a compound specifically mentioned in the Examples or a salt thereof except for a compound as such of Example 11.

Also especially preferred are all compounds of formula I which, in the test described in Example 9, have an IC₅₀ below 10 μM, and very special preference is for those with an IC₅₀ of less than 1 μM.

Very much preferred is the compound designated 1-(3-methylanilino)-4-[(2-(pyridin-3-yl)-ethyl]phthalazine (wherein the symbols in relation to formula I have the following meanings: R₂ and R₃ together form a bridge in subformula I*; r=n=m=0; A=N; B=D=E=T=CH; G=CH₂—CH₂; X=NH; Y=3-methylphenyl); or a salt thereof.

A compound of the invention may be prepared by processes known per se for other compounds, especially a) for the preparation of a compound of formula I, in which G is —CH₂—O—, —CH₂—NH—, —CH₂—S—, —O—, —S—, or —NH—, by reacting a compound of formula II,

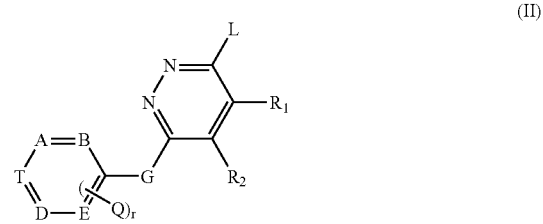

wherein A, B, D, E, T, G, Q, R₁, and R₂ are as defined for a compound of formula I and L is a nucleofugal leaving group, with a compound of formula III

wherein n, R_a, R_a', X, and Y are as defined for a compound of formula I;

b) for the preparation of a compound of formula I, in which G is lower alkylene, especially C₂-C₆alkylene, C₂-C₆- alkenylene; or lower alkylene, especially $C_2$-$C_6$alkylene, or $C_3$-$C_6$alkenylene substituted by acyloxy or hydroxy; by reacting a compound of formula IV,

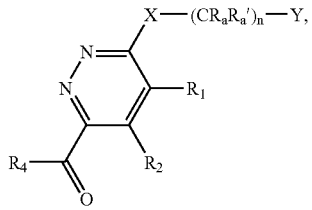
(IV)

wherein n, $R_a$, $R_a'$, X, Y, $R_1$ and $R_2$ are as defined for a compound of formula I, and $R_4$ is H or alkyl, in the presence of a base with a compound of formula V

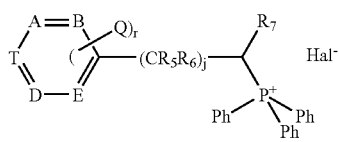
(V)

wherein r, A, B, D, E, T and Q are as defined for a compound of formula I, $R_5$, $R_6$ and $R_7$ are independently alkyl or H, j represents a whole number between 0 and 5, and Ph is phenyl, and reacting the resulting compound of formula I with $G=-CR_4=CR_7-(CR_5R_6)_j-$ if so desired for example by hydrogenation with side-group metal catalysis or addition of water and possibly subsequent acylation to form a different compound of formula I;

c) for the preparation of a compound of formula I in which G is $-CH_2-O-CH_2-$, by reacting a compound of formula IV*,

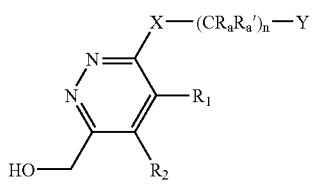
(IV*)

wherein n, $R_a$, $R_a'$, X, Y, $R_1$ and $R_2$ are as defined for a compound of formula I, in the presence of a base with a compound of formula VI,

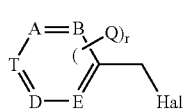
(VI)

wherein r, A, B, D, E, T and Q are as defined for a compound of formula I and Hal is halogen;

d) for the preparation of a compound of formula I in which G is $-CH_2-S-CH_2-$, by reacting a compound of formula IV**,

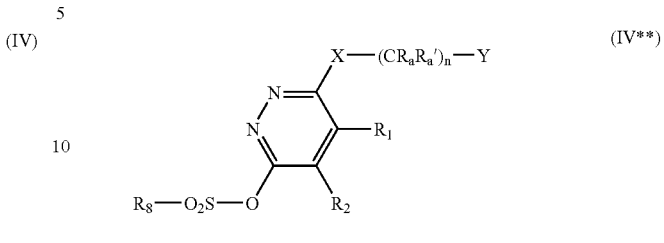
(IV**)

wherein n, $R_a$, $R_a'$, X, Y, $R_1$ and $R_2$ are as defined for a compound of formula I and $R_8$ is alkyl, for example methyl, or alkylaryl, for example tolyl, with a compound of formula VII

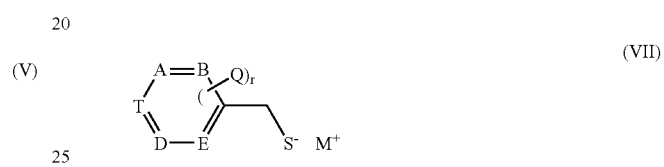
(VII)

wherein r, A, B, D, E, T and Q are as defined for a compound of formula I and $M^+$ is a metal cation containing a single charge, for example a sodium or potassium cation;

e) for the preparation of a compound of formula I in which G is $-CH_2-NHCH_2-$, by reacting a compound of formula IV***,

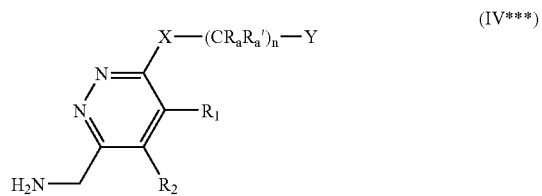
(IV***)

wherein n, $R_a$, $R_a'$, X, Y, $R_1$ and $R_2$ are as defined for a compound of formula I, with a compound of formula V*,

(V*)

wherein r, A, B, D, E, T and Q are as defined for a compound of formula I, in the presence of hydrogen and a catalyst;

wherein in compounds of formulae I to VII, IV*, IV, IV* and V*, functional groups which do not participate in the reaction are present in protected form where necessary, and removing any protective groups present, whereas said starting compounds may also be present in the form of salts if a salt-forming group is present and the reaction in salt form is possible;

and, if so desired, converting an obtainable compound of formula I or an N-oxide thereof into another compound of formula I or an N-oxide thereof, converting a free compound of formula I or an N-oxide thereof into a salt, converting an obtainable salt of a compound of formula I or an N-oxide thereof into the free compound or another salt, and/or separating a mixture of isomeric compounds of formula I or N-oxides thereof into the individual isomers.

Compounds of formula I, in which G is methylen and Q is halogen or lower alkoxy, are prepared in analogy to the methods for preparation described in the Examples and on pages 22 and 23 of WO 98/35958, wherein in formula (VI) as defined in WO 98/35958 the group Q is halogen or lower alkoxy.

DETAILED DESCRIPTION OF METHOD VARIANTS

In the more detailed description of the process method below, r, n, A, B, D, E, T, G, Q, $R_a$, $R_a'$, $R_1$, $R_2$, X and Y are as defined for compounds of formula 1, unless otherwise indicated.

Many of the compounds of the formula I, as well as their salts, the respective starting materials and intermediates can be obtained as described in WO 98/35958, or prepared by or in analogy to the methods described in WO 98/35958, which is incorporated by reference.

Process a)

In the compound of formula II, a nucleofugal leaving group L is especially halogen, above all bromine, especially chlorine or iodine.

The reaction between the compound of formula II and the compound of formula III takes place in suitable, inert polar solvents, especially alcohols, e.g. lower alcohols, such as methanol, propanol or especially ethanol or n-butanol, or in a melt without the addition of a solvent, especially if one of the reaction partners is present in liquid form. The reaction takes place at elevated temperatures, preferably between about 60° C. and the reflux temperature of the solvent used, for example under reflux conditions, or at a temperature between approximately 70 and approximately 120° C. The compound of formula III may also be used as a salt, for example as an acid addition salt with a strong acid, such as a hydrogen halide, for example as a hydrochloride salt, or the corresponding acid, for example hydrochloric acid, can be added in a suitable solvent, for example an ether, such as dioxane. If L is iodine, the reaction is preferably allowed to proceed in an inert solvent, such as toluene, in the presence of a base, especially an alkali metal carbonate, such as dipotassium carbonate, in the presence of catalytic amounts of tetrakis-(triphenylphosphin)-palladium, at elevated temperature, e.g. at 180 to 115° C.

Process b)

In formula IV, $R_4$ may be hydrogen or alkyl. In particular, $R_4$ is lower alkyl or hydrogen.

In formula V, the phenyl radicals on the phosphorus may also be freely substituted. In the preferred embodiment, the phenyl radicals on the phosphorus are unsubstituted. Instead of said phosphorus compounds, corresponding arsenic compounds may also be used. Hal⁻ in formula V is iodide and especially chloride or bromide.

An alkali metal hydride, such as sodium hydride, an alkali metal amide, such as sodium amide, an alkyl lithium compound, such as butyl lithium, an alkali metal alcoholate, such as sodium ethanolate or sodium methanolate, an alkali metal carbonat, such as sodium carbonate, or an alkaline earth metal carbonate, such as magnesium carbonate, may be used for example as a base.

The reaction is preferably carried out in the absence of water and oxygen in a suitable solvent, such as dimethyl sulfoxide, for example, at temperatures between −10° C. und +80° C., preferably between 0° C. and 40° C., for example at room temperature.

The hydrogenation with side-group metal catalysis which may subsequently be carried out if so desired can take place in a simple solvent, for example water, alcohol, ethyl acetate, dioxane or tetrahydrofuran, a mixture of these solvents, or without solvent.

Elemental gaseous hydrogen is preferably used as reaction partner for the olefin. The reaction is carried out under normal pressure or a hydrogen pressure up to 200 atm and at temperatures between 10° C. and 100° C.

In particular, platinum, palladium and nickel, as well as chemical compounds comprising these elements, for example palladium oxide or platinum oxide, can be used as catalysts. The catalyst may be bound to a substrate, for example activated carbon, barium sulfate, strontium sulfate, calcium carbonate or aluminium oxide, or may be prepared as a metal foam from a binary alloy by extraction of a partner using an acid or alkali, for example Raney nickel.

The addition of water which may be subsequently be carried out if so desired can take place by reacting the olefin first with a mercury compound, for example mercury acetate, and then with sodium borohydride or by reacting the olefins with water in the presence of an acid, for example sulfuric acid or nitric acid.

Process c)

The reaction takes place preferably in a solvent, for example dimethyl sulfoxide or dichloromethane, at temperatures between 0° C. and the boiling point of the solvent used. The base used may for example be potassium hydroxide, a mixture of HgO and $HBF_4$, or silver carbonate or silver oxide. Alternatively, the compound of formula IV* may also be deprotonated to form the corresponding alcoholate before the reaction with halogen compound VI takes place. In both cases, the reaction can be supported by the addition of phase-transfer catalysts.

Process d)

The reaction takes place preferably in a suitable polar solvent at temperatures between 0° C. and the boiling point of the solvent used. The reaction may also be enhanced by the addition of a phase-transfer catalyst.

Alternatively, instead of a compound of formula VII, the corresponding mercaptan may be used. In this case, the reaction preferably takes place in known manner in a non-polar solvent, for example benzene, preferably in the presence of DBU (1,8-diazabicyclo[5.4.0]undec-7-ene).

Process e)

The reaction takes place preferably in an inert solvent, for example an alcohol such as methanol, at temperatures between 0° C. and 100° C., preferably between 50° C. and 90° C. in a stirred autoclave at a pressure of 50 to 150 atm hydrogen, especially at a pressure of 80 to 120 atm hydrogen. One of the side-group metal catalysts described in process b can be used as catalyst. The use of Raney nickel is especially preferred.

Additional Process Steps

In the additional process steps which are carried out as desired, functional groups of the starting compounds which should not take part in the reaction may be present in unprotected form or may be protected for example by one or more of the protecting groups mentioned hereinabove. The protecting groups are then wholly or partly removed according to one of the methods described.

If one or more other functional groups, for example carboxy, hydroxy, amino, or mercapto, are or need to be protected in a compound of formulae 11 to VII, because they should not take part in the reaction, these are such as are usually used in the synthesis of peptide compounds, and also of cephalosporins and penicillins, as well as nucleic acid derivatives and sugars. The protecting groups may already be present in precursors and should protect the functional groups concerned against unwanted secondary reactions, such as acylations, etherifications, esterifications, oxidations, solvolysis, and similar reactions. In certain cases, the protecting groups may, in addition to this protection, effect a selective, typically stereoselective, course of reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. A person skilled in the art knows, or can easily establish, which protecting groups are suitable with the reactions mentioned hereinabove and hereinafter.

The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosäuren, Peptide, Proteine" (*Amino acids, peptides, proteins*). Verlag Chemie, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974.

The protecting groups mentioned in the Examples are preferably introduced according to the methods described and where necessary removed.

Salts of a compound of formula I (or an N-oxide thereof) with a salt-forming group may be prepared in a manner known per se. Acid addition salts of compounds of formula I or of N-oxides thereof may thus be obtained by treatment with an acid or with a suitable anion exchange reagent. A salt with two acid molecules (for example a dihalogenide of a compound of formula I [or an N-oxide thereof]) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of formula I (or an N-oxide thereof).

Salts can usually be converted to free compounds, e.g. by treating with suitable basic agents, for example with alkali metal carbonates, hydrogencarbonates, or hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of one of the starting compounds or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

A compound of formula I can be converted to a corresponding N-oxide. The reaction is carried out with a suitable oxidizing agent, preferably a peroxide, for example m-chloroperbenzoic acid or Oxone® (trademark by DuPont, USA; potassium monopersulfate triple salt), in a suitable solvent, e.g. a halogenated hydrocarbon, typically chloroform or dichloromethane, or in a lower alkanecarboxylic acid, typically acetic acid, preferably at a temperature between 0° C. and the boiling temperature of the reaction mixture, especially at about room temperature.

A compound of formula I (or an N-oxide thereof), wherein $R_1$ and $R_2$ together form a bridge in subformula I* and wherein Z is lower alkanoylamino, can be hydrolysed to a corresponding amino compound (Z=amino), for example by hydrolysis with an inorganic acid, especially hydrochloric acid (HCl) in an aqueous solution, further solvents possibly being added, preferably at elevated temperature, e.g. under reflux.

A compound of formula I (or an N-oxide thereof), wherein $R_1$ and $R_2$ together form a bridge in subformula I* and wherein Z is amino substituted by one or two radicals selected independently from lower alkyl, hydroxy-lower alkyl, and phenyl-lower alkyl, can be converted to a compound that is correspondingly substituted at the amino group, for example by reaction with a lower alkyl halide, if necessary a hydroxy-protected (see process a)) hydroxy-lower alkyl halide or phenyl-lower alkyl halide, under reaction conditions as described under process a). For the introduction of 2-hydroxy-lower alkyl substituents at the amino group Z, addition based on an epoxide (for example ethylene oxide) is also possible. The addition takes place especially in aqueous solution and/or in the presence of polar solvents, typically alcohols, for example methanol, ethanol, isopropanol, or ethylene glycol, ethers, typically dioxane, amides, typically dimethylformamide, or phenols, typically phenol, and also under non-aqueous conditions, in non-polar solvents, typically benzene and toluene, or in benzene/water emulsions, where applicable in the presence of acidic or basic catalysts, for example alkaline solutions, typically sodium hydroxide solution, or in the presence of solid-phase catalysts, typically aluminium oxide, that have been doped with hydrazine, in ethers, for example diethylether, generally at temperatures from about 0° C. to the boiling temperature, of the corresponding reaction mixture, preferably between 20° C. and reflux temperature, if necessary under increased pressure, e.g. in a sealed tube, whereby the boiling temperature may also be exceeeded, and/or under inert gas, typically nitrogen or argon. Reductive alkylation of an amino group Z with a lower alkanaldehyde, a phenyl-lower alkanaldehyde, or a hydroxy-lower alkanaldehyde (hydroxy -protected if necessary), is also possible. Reductive alkylation takes place preferably under hydrogenation in the presence of a catalyst, especially a precious-metal catalyst, typically platinum or especially palladium, which is preferably bound to a carrier, such as carbon, or in the presence of a heavy-metal catalyst, typically Raney-Nickel, at normal pressure or at pressures from 0.1 to 10 megapascal (MPa), or under reduction using complex hydrides, typically boranes, especially alkali cyanoborohydride, for example sodium cyanoborohydride, in the presence of a suitable acid, preferably a relatively weak acid, typically a lower alkanecarboxylic acid or especially a sulfonic acid, such as p-toluenesulfonic acid; in customary solvents, for example alcohols, such as methanol or ethanol, or ethers, for example cyclic ethers, such as tetrahydrofuran, in the presence or absence of water.

In a compound of formula I (or an N-oxide thereof), wherein $R_1$ and $R_2$ together form a bridge in subformula I*, an amino group Z can be converted by acylation to form an amino group substituted by lower alkanoyl, benzoyl, substituted benzoyl or phenyl-lower alkoxycarbonyl, wherein the phenyl radical is unsubstituted or substituted. The corresponding acids comprise a free carboxy group or are present as reactive acid derivatives thereof, for example derivative activated esters or reactive anhydrides, and also reactive cyclic amides. The reactive acid derivatives may also be formed in situ. Activated esters are especially unsaturated esters at the bonding carbon atom of the radical to be esterified, for example of the vinyl ester type, typically vinyl ester (obtainable for example by reesteriication of an appropriate ester with vinyl acetate; method of activated vinyl ester), carbamoyl ester (obtainable for example by treatment of the corresponding acid with an isoxazolium reagent; 1,2-oxazolium or Woodward method), or 1-lower alkoxyvinyl ester (obtainable for example by treatment of the corresponding acid with a lower alkoxyacetylene; ethoxyacetylene method), or esters of the amidino type, typically N,N'-disubstituted amidino ester (obtainable for example by treatment of the corresponding acid with a suitable N,N'-disubstituted carbodiimide, for example N,N'-dicyclohexylcarbodiimide or especially N-(3-dimethylaminopropyl)-N'-ethylcarbodiimide; carbodiimide method), or N,N-disubstituted amidino ester (obtainable for example by treatment of the corresponding acid with an N,N-disubstituted cyanamide; cyanamide method), suitable aryl esters, especially phenyl esters suitably substituted by electrophilic substituents (obtainable for example by treatment of the corresponding acid with a suitably substituted phenol, for example 4-nitrophenol, 4-methylsulfonylphenol, 2,4,5-trichlorophenol, 2,3,4,5,6-pentachlorophenol or 4-phenyl-diazaphenol, in the presence of a condensing agent, typically N,N'-dicyclohexylcarbodiimide; method of activated aryl esters), cyanomethyl esters (obtainable for example by treatment of the corresponding acid with chloroacetonitrile in the presence of a base; cyanomethyl ester method), thioesters, where appropriate especially phenylthio esters substituted, for example, by nitro (obtainable for example by treatment of the corresponding acid where appropriate with thiophenols substituted, for example, by nitro, with the aid also of the anhydride or carbodiimide method; method of activated thiolesters), or especially amino or amido esters (obtainable for example by treatment of the corresponding acid with an N-hydroxyamino- or N-hydroxyamido compound, for example N-hydroxysuccinimide, N-hydroxypiperidine, N-hydroxyphthalimide, N-hydroxy-5-norbornene-2,3-dicarboximide, 1-hydroxybenztriazole or 3-hydroxy-3,4-dihydro-1,2,3-benztriazin-4-one, for example according to the anhydride or carbodiimide method; method of activated N-hydroxy esters). Internal esters, for example γ-lactones, can also be used. Anhydrides of acids can be symmetrical or preferably mixed anhydrides of these acids, for example anhydrides with inorganic acids, typically acid halides, especially acid chloride (obtainable for example by treatment of the corresponding acid with thionyl chloride, phosphorus pentachloride, phosgene or oxalyl chloride; acid chloride method), azide (obtainable for example from a corresponding acid ester via the corresponding hydrazide and treatment thereof with nitrous acid; azide method), anhydrides with carbonic acid semi-esters, e.g. carbonic acid-lower alkyl semi-esters (especially methyl chlorocarbonate) (obtainable for example by treatment of the corresponding acid with chlorocarbonic acid-lower alkyl esters or with a 1-lower alkoxycarbonyl-2-lower alkoxy-1,2-dihydroquinoline; method of mixed O-alkylcarbonic anhydrides), or anhydrides with dihalogenated, especially dichlorinated phosphoric acid (obtainable for example by treatment of the corresponding acid with phosphoroxychloride; phosphoroxychloride method), anhydrides with other phosphoric acid derivatives (for example, such that can be obtained with phenyl-N-phenylphosphoramidochloridate or by reaction of alkylphosphoric acid amides in the presence of sulfonic acid anhydrides and/or racemization-reducing additives, typically N-hydroxybenztriazole, or in the presence of cyanophosphonic acid diethyl ester) or with phosphorous acid derivatives, or anhydrides with organic acids, such as mixed anhydrides with organic carbonic acids (obtainable for example by treatment of the corresponding acid with a lower alkane or phenyl-lower alkanecarboxylic acid halide, substituted where appropriate, typically phenyl-acetyl, pivaloyl, or trifluoroacetic acid chloride; method of mixed carboxylic acid anhydrides) or with organic sulfonic acids (obtainable for example by treatment of a salt, typically an alkali metal salt, the corresponding acid with a suitable organic sulfonic acid halide, typically lower alkane or aryl, for example methane or p-toluenesulfonic acid chloride; method of mixed sulfonic acid anhydrides), as well as symmetrical anhydrides (obtainable for example through condensation of the corresponding acid in the presence of a carbodiimide or of 1-diethylaminopropine; method of symmetrical anhydrides). Suitable cyclic amides are especially amides with five-member diazacycles of aromatic character, typically amides with imidazolene, for example imidazole (obtainable for example by treatment of the corresponding acid with N,N'-carbonyldiimidazole; imidazole method), or pyrazole, for example 3,5-dimethylpyrazole (obtainable for example via the acid hydrazide by treatment with acetylacetone; pyrazolide method). As mentioned, carboxylic acid derivatives, which are used as acylation agents, can also be formed in situ. For example, N,N'-disubstituted amidino esters can be formed in situ by reacting the mixture of the starting material of formula I and the acid used as acylation agent in the presence of a suitable N,-N'-disubstituted carbodiimide, for example N,-N'-cyclohexylcarbodiimide or in particular N-(3-dimethylaminopropyl)-N'-ethylcarbodiimide. Amino or amido esters of the acids used as acylation agents can also be formed in the presence of the starting material of formula I that is to be acylated by reacting the mixture of the corresponding acid and amino starting materials in the presence of an N,N'-disubstituted carbodiimide, for example N,N'-dicyclohexylcarbodiimide, and an N-hydroxyamine or N-hydroxyamide, for example N-hydroxysuccinimide, where appropriate in the presence of a suitable base, for example 4-dimethylaminopyridine. Activation can also be achieved in situ through reaction with N,N,N',N'-tetraalkyluronium compounds, typically O-benztriazol-1yl-N,N,N',N'-tetramethyluronium hexafluorophosphate, O-(1,2-dihydro-2-oxo-1-pyridyl)-N,N,N',N'-tetramethyluronium tetrafluoroborate (in the presence or absence of 1,8-diazabicyclo[5.4.0]undec-7-ene-(1,5-5)), or O-(3,4-dihydro-4-oxo-1,2,3-benztriazolin-3-yl)-N,N,N',N'-tetramethyluronium tetrafluoroborate. Finally, phosphoric acid anhydrides of carboxylic acids can be prepared in situ by reacting an alkylphosphoric acid amide, typically hexamethylphosphoric acid triamide, in the presence of a sulfonic acid anhydride, typically 4-toluenesulfonic acid anhydride, with a salt, such as tetrafluoroborate, for example sodium tetrafluoroborate, or with another derivative of hexamethylphosphoric acid triamide, typically benzotriazol-1-yl-oxy-tris-(dimethylamino)-phosphonium hexafluoride. If desired, an organic base is added, preferably a tertiary amine, for example a tri-lower alkylamine, especially ethyldiisopropylamine or above all triethylamine, and/or a heterocyclic base, for example 4-dimethylaminopyridine or preferably N-methylmorpholine or pyridine. Condensation is carried out preferably in an inert, aprotic, preferably non-aqueous solvent or solvent mixture, typically in a carboxamide, for example formamide or dimethylformamide, a halogenated hydrocarbon, for example dichloromethane, tetrachloromethane, or chlorobenzene, a ketone, for example acetone, a cyclic ether, for example tetrahydrofuran or dioxane, an ester, for example ethyl acetate, or a nitrile, for example acetonitrile, or in a mixture thereof, where appropriate at reduced or elevated temperature, for example in a range from about −40° C. to about +100° C., preferably from about −10° C. to about +70° C., also from about +100° C. to +200° C. when arylsulfonyl esters are used, especially at temperatures between 10 and 30° C., and where appropriate under inert gas, for example nitrogen or argon. Aqueous, typically alcoholic, for example ethanol, or aromatic solvents, for example benzene or toluene, are also possible.

A nitro group Z in a compound of formula I, wherein $R_1$ and $R_2$ together form a bridge in subformula I*, can be reduced to an amino group, for example by reduction with metals or by selective hydrogenation; for example by reaction with magnesium/ammonium sulfate in a water/alcohol mixture, typically methanol/water, at elevated temperature, for example between 30 and 60° C. (see Synth. Commun. 25 [2], 4025-8 [1995]); by reaction with zinc/borohydride in an acid amide, typically dimethylformamide, at temperatures below room temperature, for example at about 0° C.; by reaction with 1,1'-dioctyl4,4'-bipyridinium dibromide/sodium tetrathionate/potassium carbonate in water/halogenated hydrocarbon mixtures, for example water/dichloromethane mixtures, at elevated temperature, for example from 25 to 35° C. (see Tetrahedron Lett. 34(46), 7445-6 (1993)); with sodium borohydride on Amberlyte IRA-400 ion exchanger in the chloride form in an alcohol, typically methanol/water, at preferred temperatures between 0 and 40° C. (see Synthetic Commun. 19(5/6), 805-11 (1989)); with potassium borohydride in a halogenated hydrocarbon/alcohol mixture, for example dichloromethane/methanol, at preferred temperatures between 10 and 35° C. (see Synthetic Commun. 19(17), 3047-50 (1989)); with sodium borohydride in dioxane; with borane in tetrahydrofuran; by hydrogenation in the presence of Pd/C in an alcohol at a preferred temperature of 0 to 35° C. and in the presence of ammonium formate (see Tetrahedron Lett. 25(32), 3415-8 (1989)); with titanium tetrachloride/lithium aluminium hydride or titanium tetrachloride/magnesium in an ether, typically tetrahydrofuran (see Bull. Chem. Soc. Belg. 97 [1], 51-3 [1988]); or with ferric ammonium chloride/water at elevated temperature, preferably under reflux (Synth. Commun. 22, 3189-95 [1992]).

In a compound of formula I, wherein G is lower alkyl substituted by acyloxy and the other radicals are as defined under formula I, the acyl radical can be removed by hydrolysis, resulting in the corresponding compound of formula I, in which G is lower alkylene substituted by hydroxy. The hydrolysis is carried out preferably under the usual conditions, typically in the presence of acids or bases, such as HCl or NaOH, in aqueous solution or a suitable solvent or solvent mixture.

From a compound of formula I wherein G is methylene or $C_2$-$C_6$alkylene substituted by hydroxy, a compound of formula I wherein G is methylene or $C_2$-$C_6$alkylene can also be prepared by dehydrogenation. From a compound of formula I wherein G is $C_2$-$C_6$alkenylene, a compound of formula I wherein G is $C_2$-$C_6$alkylene can also still be prepared by hydrogenation. The reaction takes place here preferably with catalytic hydrogenation under the conditions stated hereinabove.

A compound of the formula I, wherein G is methylene, can be converted into the corresponding compound of the formula I, especially IA, wherein G is hydroxymethyl or —C(═O)— by oxidation, e.g. by heating, for example boiling, over charcoal in an alcohol, e.g. methanol, in the presence of air or an atmosphere enriched with oxygen.

A compound of the formula I, especially IA, wherein G is methylene can be converted into the corresponding compound of the formula I wherein G is —CHF— or —$CF_2$— by reaction with electrophilic fluorine, e.g. according to the method described in Tetrahedron Lett. 32, 1779 (1991), that is, by adding the compound of the formula I to be converted in an appropriate solvent, e.g. a cyclic ether, such as tetrahydrofurane, preferably under an inert gas, e.g. in a $N_2$-atmosphere, preferably dropwise to a solution of potassium bis(trimethylsilyl)amide in an appropriate solvent, e.g. a cyclic ether, such as tetrahydrofurane, in the cold, e.g. cooled to 0 to about −80° C., e.g. at about −78° C.; and then slow addition of 2-fluoro-3,3-dimethyl-2,3-dihydro-1,2-benzisothiazole in the same solvent, and allowing to react-in the same temperature range.

General Process Conditions

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralisiing agents, for example ion exchangers, typically cation exchangers, for example in the H⁺ form, depending on the type of reaction and/or reactants at reduced, normal, or elevated temperature, for example in the range from −100° C. to about 190° C., preferably from about −80° C. to about 150° C., for example at −80 to 60, at room temperature, at −20 to 40° C. or at the boiling point of the solvent used, under atmospheric pressure or in a closed vessel, if need be under pressure, and/or in an inert, for example an argon or nitrogen, atmosphere.

Salts may be present in all starting compounds and intermediates, if these contain salt-forming groups. Salts may also be present during the reaction of such compounds, provided the reaction is not thereby disturbed.

At all reaction stages, isomeric mixtures that occur can be separated into their individual isomers, e.g. diastereomers or enantiomers, or into any mixtures of isomers, e.g. racemates or diastereomeric mixtures, typically as described under "Additional process steps".

In certain cases, typically in dehydrogenation, it is possible to achieve stereoselective reactions, allowing for example easier recovery of individual isomers.

The solvents from which those can be selected which are suitable for the reaction in question include for example water, esters, typically lower alkyl-lower alkanoate, e.g diethyl acetate, ethers, typically aliphatic ethers, e.g. diethylether, or cyclic ethers, e.g. tetrahydrofuran, liquid aromatic hydrocarbons, typically benzene or toluene, alcohols, typically methanol, ethanol or 1- or 2-propanol, nitrites, typically acetonitrile, halogenated hydrocarbons, typically dichloromethane, acid amides, typically dimethylformamide, bases, typically heterocyclic nitrogen bases, e.g. pyridine, carboxylic acids, typically lower alkanecarboxylic acids, e.g. acetic acid, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process. Such solvent mixtures may also be used in processing, for example through chromatography or distribution.

The invention relates also to those forms of the process in which one starts from a compound obtainable at any stage as an intermediate and carries out the missing steps, or breaks off the process at any stage, or forms a starting material under the reaction conditions, or uses said starting material in the form of a reactive derivative or salt, or produces a compound obtainable by means of the process according to the invention and processes said compound in situ. In the preferred embodiment, one starts from those starting materials which lead to the compounds described hereinabove as preferred, particularly as especially preferred, primarily preferred, and/or preferred above all.

In the preferred embodiment, a compound of formula I (or N-oxides thereof) is prepared according to the processes and process steps defined in the Examples.

The compounds of formula I (or N-oxides thereof), including their salts, are also obtainable in the form of hydrates, or their crystals can include for example the solvent used for crystallization (present as solvates).

Pharmaceutical Preparations, Methods, and Uses

The present invention relates also to pharmaceutical compositions that comprise a compound of formula I (or an N-oxide thereof) as active ingredient and that can be used especially in the treatment of the diseases mentioned at the beginning. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient (a compound of the formula I, or a pharmaceutically acceptable salt thereof) alone or, preferably, together with a pharmaceutically acceptable carrier. The dosage of the active ingredient depends upon the disease to be treated and upon the species, its age, weight, and individual condition, the individual pharmacokinetic data, and the mode of administration.

The invention relates also to pharmaceutical compositions for use in a method for the prophylactic or especially therapeutic management of the human or animal body, to a process for the preparation thereof (especially in the form of compositions for the treatment of tumours) and to a method of treating tumour diseases, especially those mentioned above, where especially a novel compound of the formula I, especially IA, is used.

The invention relates also to processes and to the use of compounds of formula I (or an N-oxide thereof) for the preparation of pharmaceutical preparations which comprise compounds of formula I (or an N-oxide thereof) as active component (active ingredient).

The said pharmaceutical preparations may also, if so desired, comprise other active components, for example cytostatic agents, and/or be used in combination with known therapeutic methods, for example the administration of hormones or irradiation.

Preference is for a pharmaceutical preparation which is suitable for administration to a warm-blooded animal, especially humans or commercially useful mammals suffering from an inflammatory rheumatoid or rheumatic disease and/or pain, or a disease which responds to an inhibition of angiogenesis or of VEGF-receptor tyrosine kinase, for example psoriasis or especially a neoplastic disease, comprising an effective quantity of a compound of formula I (or an N-oxide thereof) for the inhibition of angiogenesis or of VEGF-receptor tyrosine kinase, or a pharmaceutically acceptable salt thereof, if salt-forming groups are present, together with at least one pharmaceutically acceptable carrier.

A pharmaceutical composition for the prophylactic or especially therapeutic management of a rheumatoid or rheumatic inflammatory disease and/or pain, or a neoplastic and other proliferative disease of a warm-blooded animal, especially a human or a commercially useful mammal requiring such treatment, especially suffering from such a disease, comprising as active ingredient in a quantity that is prophylactically or especially therapeutically active against said diseases a new compound of formula I (or an N-oxide thereof), is likewise preferred.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories, or capsules. Examples are capsules containing from about 0.05 g to about 1.0 g of active substance.

The pharmaceutical compositions of the, present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilised compositions which comprise the active ingredient on its own or together with a carrier, can be made up before use. The pharmaceutical compositions may be sterilised and/or may comprise excipients, for example preservatives, stabilisers, wetting agents and/or emulsifiers, solubilisers, salts for regulating the osmotic pressure and/or buffers and are prepared in a manner known per se, for example by means of conventional dissolving and lyophilising processes.

Suspensions in oil comprise as the oil component the vegetable, synthetic, or semi-synthetic oils customary for injection purposes. Such components are in particular liquid fatty acid esters, for example ethyl oleate, isopropyl myristate, isopropyl palmitate, "Labrasol" (Gatte-fossé, Paris), and/or "Miglyol 812" (Hüls AG, Germany), but especially vegetable oils such as cottonseed oil, almond oil, olive oil, castor oil, sesame oil, soybean oil and more especially groundnut oil.

The manufacture of injectable preparations is usually carried out under sterile conditions, as is the filling, for example, into ampoules, and the sealing of the containers.

Pharmaceutical compositions for oral administration can be obtained, for example, by combining the active ingredient with one or more solid carriers, if need be granulating a resulting mixture, and processing the mixture or granules, if desired, to form tablets or tablet cores, if need be by the inclusion of additional excipients.

Suitable carriers are especially fillers, such as sugars, for example saccharose, mannitol or sorbitol, cellulose preparations, and/or calcium phosphates, and also binders, such as starches, for example corn, wheat, rice or potato starch, methylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof and/or polyethylene glycol, or derivatives thereof.

Tablet cores may be provided with suitable, if need be enteric, coatings, using inter alia concentrated sugar solutions which may comprise gum arabic, talc, polyvinylpyrrolidone, polyethylene glycol and/or titanium dioxide, or coating solutions in suitable organic solvents or, for the preparation of enteric coatings, solutions of suitable cellulose preparations, such as acetylcellulose phthalate or hydroxypropylmethylcellulose phthalate. Dyes or pigments may be added to the tablets or tablet coatings, for example to indicate different doses of active ingredient.

Orally administrable pharmaceutical compositions also include hard capsules consisting of gelatin, and also soft, sealed capsules consisting of gelatin and a plasticiser, such as glycerol or sorbitol. The hard capsules may contain the active ingredient in the form of granules, for example in admixture with fillers, such as corn starch, binders, and/or glidants, and if need be stabilisers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilisers and detergents may also be added.

Suitable rectally administrable pharmaceutical compositions are, for example, suppositories that consist of a combination of the active ingredient and a suppository base.

The aqueous solutions suitable for parenteral administration are especially those of an active ingredient in water-soluble form, for example in the form of a water-soluble salt, or aqueous injection suspensions that contain viscosity-increasing-substances, for example sodium carboxymethylcellulose or dextran, and, if need be, stabilisers. The active ingredient, where applicable together with excipients, may be present in the form of a lyophilizate and rendered into solution before administration. Solutions such as are used for parenteral administration can also be employed as infusion solutions.

Preferred preservatives are, for example, antioxidants, such as ascorbic acid, or microbicides, such as sorbic acid or benzoic acid.

The invention relates likewise to a process or a method for the treatment of one of the pathological conditions mentioned hereinabove, especially an inflammatory rheumatic or rheumatoid disease and/or pain, or (especially in the case of novel compounds of the formula I) a disease which responds to an inhibition of the VEGF-receptor tyrosine kinase or an inhibition of angiogenesis, especially a corresponding neoplastic disease or also psoriasis. The compounds of formula I (or an N-oxide thereof) can be administered as such or in the form of pharmaceutical compositions, prophylactically or therapeutically, preferably in an amount effective against said diseases, to a warm-blooded animal, for example a human, requiring such treatment, the compounds especially being used in the form of pharmaceutical compositions. In the case of an individual having a bodyweight of about 70 kg the daily dose administered is from approximately 0.1 g to approximately 5 g, preferably from approximately 0.5 g to approximately 2 g, of a compound of the present invention.

The present invention relates especially also to the use of a compound of formula I (or an N-oxide thereof), or a pharmaceutically acceptable salt thereof, especially a compound of formula I which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, preferably an inflammatory rheumatic or rheumatoid disease and/or pain, or (especially in the case of novel compounds of the formula I) a disease which responds to an inhibition of VEGF-receptor tyrosine kinase or an inhibition of angiogenesis, especially a neoplastic disease or also psoriasis, above all if said disease responds to an inhibition of VEGF-receptor tyrosine kinase or angiogenesis.

The present invention relates especially also to the use of a compound of formula I (or an N-oxide thereof), or a pharmaceutically acceptable salt thereof, especially a compound of formula I which is said to be preferred, or a pharmaceutically acceptable salt thereof, for the preparation of a pharmaceutical formulation for the therapeutic and also prophylactic management of one or more of the diseases mentioned hereinabove, especially a rheumatic or rheumatoid inflammatory disease and/or pain, or (especially in the case of novel compounds of the formula I) a neoplastic disease or also psoriasis, above all if the disease responds to an inhibition of VEGF-receptor tyrosine kinase or angiogenesis.

The preferred dose quantity, composition, and preparation of pharmaceutical formulations (medicines) which are to be used in each case are described above.

Starting Materials

New starting materials and/or transients, as well as processes for the preparation thereof, are likewise the subject of this invention. In the preferred embodiment, such starting materials are used and reaction conditions so selected as to enable the preferred compounds to be obtained.

The starting materials of formulae II to VII are known, capable of being prepared according to known processes, or commercially obtainable; in particular, they can be prepared using processes as described in the Examples.

In the preparation of starting materials, existing functional groups which do not participate in the reaction should, if necessary, be protected. Preferred protecting groups, their introduction and their removal are described hereinabove or in the Examples. In place of the respective starting materials and transients, salts thereof may also be used for the reaction, provided that salt-forming groups are present and the reaction with a salt is also possible. Where the term starting materials is used hereinbefore and hereinafter, the salts thereof are always included, insofar as reasonable and possible.

A compound of formula II, wherein G is —CH$_2$—O, —CH$_2$—S—, —CH$_2$—NH—, oxa, thia, or imino and the remaining symbols are as defined under formula I, can be prepared for example by reacting a compound of formula VIII,

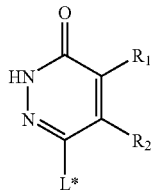

(VIII)

wherein L* is a nucleofugal leaving group, especially halo, for example bromo, and $R_1$ and $R_2$ are as defined for a compound of formula I, with a compound of formula VII,

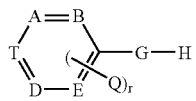

(VII)

wherein G is —$CH_2$—O—, —$CH_2$—S— or —$CH_2$—NH—, or in the broader sense oxa, thia or imino and A, B, D, E, T, Q and r are as defined for compounds of formula I, preferably under conditions analogous to those stated under process a) for the reaction of a compound of formula II with a compound of formula III. This then results in a compound of formula II*

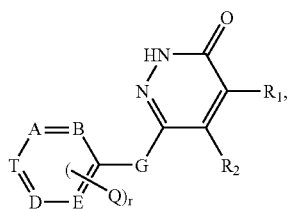

(II*)

wherein $R_1$ and $R_2$ as well as A, B, D, E, T, Q and r are as defined for a compound of formula I and wherein G is —$CH_2$—O—, —$CH_2$—S— or —$CH_2$—NH—, or in the broader sense oxa, thia or imino.

From this the corresponding compound of formula II can be prepared by introducing a leaving group L, as defined under formula II, with an inorganic acid chloride, for example phosphoryl chloride ($POCl_3$), phosgene ($COCl_2$) or thionyl chloride ($SOCl_2$), for the introduction of L=Cl or another reagent suitable for the reaction of a compound of formula II* to form a compound of formula II.

The starting materials of formulae VII to VIII are known, capable of being prepared according to known processes, or commercially obtainable; in particular, they can be prepared using processes as described in the Examples.

A compound of formula V can be obtained by reacting triarylphosphine with a compound of formula VI*, wherein A, B, D, E, T, Q, r, $R_5$, $R_6$, $R_7$, j and Hal are as defined for a compound of formula V,

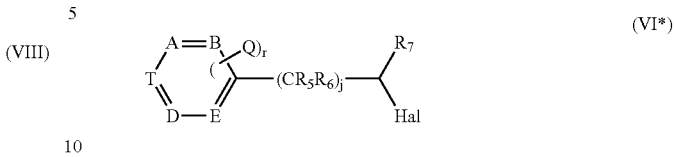

(VI*)

in an inert solvent, for example toluene, at temperatures between 20° C. and 110° C., in particular 60° C. and 80° C.

A compound of formula IV is obtainable for example by the following reaction sequence. A compound of formula IX,

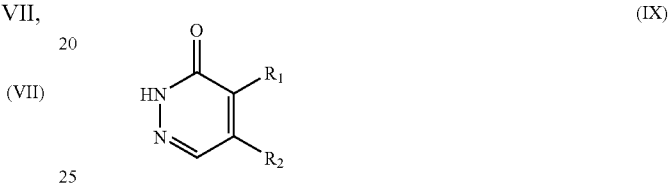

(IX)

wherein $R_1$ and $R_2$ are as defined for a compound of formula I, is reacted with an inorganic acid chloride, for example phosphoryl chloride ($POCl_3$), phosgene ($COCl_2$) or thionyl chloride ($SOCl_2$), in a suitable solvent, such as acetonitrile or dioxane, or a mixture of such solvents at temperatures between 20° C. and 80° C., for example 50° C., initially to form a compound of formula X,

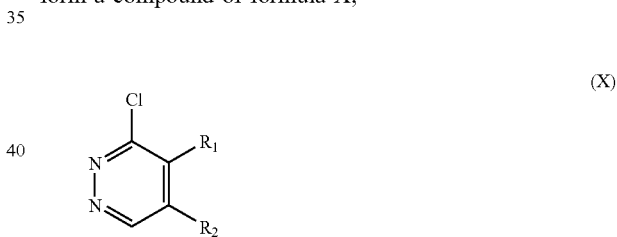

(X)

This compound of formula X is then reacted with a compound of formula III, preferably under reaction conditions analogous to those stated under process a) for the reaction of a compound of formula II with a compound of formula III. This then results in a compound of formula XI,

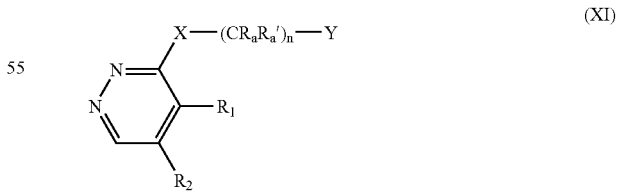

(XI)

which is converted with a 2,4,6-tri-lower alkyl-1,3,5-trioxane or 1,3,5-trioxane and an alkyl hydroperoxide, for example tert-butyl hydroperoxide, in the presence of an iron(II) compound, for example iron(II) sulfate, at temperatures between 60° C. and 100° C., for example 80° C., in a suitable solvent, for example acetonitrile, and trifluoroacetic acid to form a compound of formula XII,

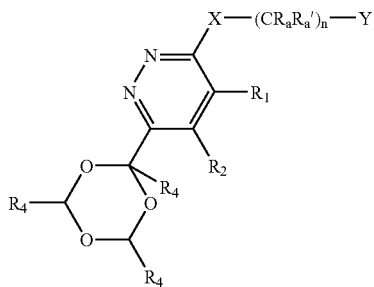

wherein $R_1$ and $R_2$ and X, Y, n, $R_a$ and $R_{a'}$ are as defined for a compound of formula I and wherein $R_4$ is H or lower alkyl. The reaction of a compound of formula XII in aqueous acid, for example 10% aqueous sulfuric acid, at temperatures between 75° C. and 110° C., preferably 90 to 100° C., yields a compound of formula IV.

The preparation of compounds of formula I, in which G is —$CH_2$—O—$CH_2$—, $CH_2$—S—$CH_2$— or —$CH_2$—NH—$CH_2$—, can take place for example in each case starting from a compound of formula IV, wherein n, $R_a$, $R_a'$, X, Y, $R_1$ and $R_2$ are as defined for a compound of formula I.

The reaction of a compound of formula IV in known manner with a reducing agent, such as lithium aluminium hydride, in a suitable solvent, for example diethyl ether or tetrahydrofuran, yields a compound of formula IV* for process c) for the preparation of compounds of formula I in which G is —$CH_2$—O—$CH_2$—.

A compound of formula IV* can be reacted with an alkylsulfonyl chloride, for example methanesulfonic acid chloride, or an alkylarylsulfonyl chloride, for example toluenesulfonic acid chloride, to form a compound of formula IV**, which can be used as described under process d) for preparing compounds of formula I in which G is —$CH_2$—S—$CH_2$—.

The reaction of a compound of formula IV with ammonia yields in known manner a compound of formula XIII

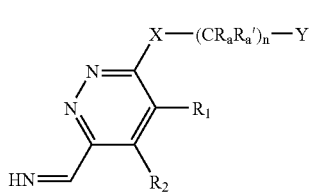

wherein n, $R_a$, $R_a'$, X, Y, $R_1$ and $R_2$ are as defined for a compound of formula I. The reaction of this compound with a reducing agent, such as lithium aluminium hydride or sodium borohydride, yields a compound of formula IV*** for process e) for the preparation of compounds of formula I in which G is —$CH_2$—N—$CH_2$—.

The starting materials are known, capable of being prepared according to known processes, or commercially available; in particular, they can be prepared using processes identical or analogous to those described in the Examples.

EXAMPLES

The following Examples serve to illustrate the invention without limiting the invention in its scope.

Temperatures are measured in degrees Celsius. Unless otherwise indicated, the reactions take place at room temperature. The $R_f$ values, which indicate the difference between the distance run by the substance in question and the distance run by the solvent front, are determined by thin-layer chromatography on silica gel thin-layer plates (Merck, Darmstadt, Germany) using said solvent systems.

HPLC:

Gradients:
Grad$_{20-100}$ 20%→100% a) in b) for 13 min+5 min 100% a).
Grad$_{5-40}$ 5%→40% a) in b) for 7.5 min+7 min 40% a).

Solvent System:
a): Acetonitrile+0.05% TFA; b): water+0.05% TFA. Column (250×4.6 mm) packed with reversed-phase material C18-Nucleosil (5 μm mean particle size, with silica gel covalently derivatized with octadecylsilanes, Macherey & Nagel, Düren, Germany). Detection by UV absorption at 215 nm. The retention times ($t_R$) are given in minutes. Flow rate: 1 ml/min.

Further short forms and abbreviations used have the following definitions:
abs. absolute (non-aqueous solvent)
an. calc. Calculated (theoretical) proportions of elements in elemental analysis
an. meas. Actual measured proportions of elements in elemental analysis
DIPE Diisopropyl ether
DMSO Dimethyl sulfoxide
Ether Diethyl ether
EtOAc Acetic acid ethyl ester
FAB-MS Fast atom bombardment mass spectroscopy
sat. Saturated
h Hour(s)
HV High vacuum
min Minute(s)
RT Room temperature
RE Rotary evaporator
m.p. Melting point
brine Saturated sodium chloride solution
THF Tetrahydrofuran (dist. over Na/benzophenone)
TFA Trifluoroacetic acid
TLC Thin-layer chromatogram Example 1

E-1-(3-Methylanilino)-4-[(2-(pyridin-3-yl)vinyl]phthalazine and Z-1-(3-methyl-anilino)-4-[(2-(pydridin-3-yl)vinyl]phthalazine Under $N_2$ atmosphere, 178 mg NaH (60% in oil; 4.45 mmol) is washed 3 times with hexane, 6 ml DMSO is added, and the mixture heated for 30 min to 70° C. (gas evolution). At RT, the mixture is diluted with 4 ml DMSO, 1.58 g (4.05 mmol) triphenyl(pyridin-3-yl-methyl)phosphonium chloride (see 1.1) is added in portions, and the reddish-black solution is stirred for 10 min. Then 1.07 g (4.06 mmol) 1-(3-methylanilino)phthalazine-4-carbaldehyde (for preparation see Example 1e) is rinsed with 10 ml DMSO into the reaction mixture and stirred at RT. After 21 h, the reaction mixture is poured onto water/EtOAc, the aqueous phase is separated off, and extracted twice with EtOAc. The organic phases are washed three times with water and brine, dried ($Na_2SO_4$) and concentrated by evaporation. Column chromatography ($SiO_2$; EtOAc/toluene 3:1) yields the E-isomer, followed by the Z-isomer. E-isomer: TLC (EtOAc) $R_f$=32; $HPLC_{20-100}$ $t_R$=6.2; $^1$H-NMR (DMSO-$d_6$) 9.10 (s, HN), 8.89 (d, 1H), 8.52 (m, 2H), 8.44 (dd, 1H), 8.23 (dt, 1H), 8.12 (d, J=15.8 Hz, HC$^{vinyl}$), 7.93 (m, 2H), 7.80 (d, J=15.8 Hz, HC$^{vinyl}$), 7.75 (s, 1H), 7.64 (d, 1H), 7.37 (dd, 1H), 7.16 (dd, 1H), 6.78 (d, 1H), 2.26 (s, 3H); FAB-MS (M+H)$^+$=339; an. calc. ($C_{22}H_{18}N_4$.0.1 $H_2O$) C, 77.67%; H, 5.39%; N, 16.47%; meas. C, 77.62%; H, 5.55%; N, 16.25%. Z-isomer: TLC (EtOAc) $R_f$=0.25; $HPLC_{20-100}$ $t_R$=5.9; $^1$H-NMR (DMSO-$d_6$) 9.18 (s, HN), 8.62 (d, 1H), 8.36 (d, 1H), 8.31 (dd, 1H), 7.97 (m, 2H), 7.89 (dd, 1H), 7.75 (s, 1H), 7.71 (d, 1H), 7.52 (dt, 1H), 7.26-7.15 (m, 3H), 7.03 (d, J=12.2 Hz, HC$^{vinyl}$), 6.86 (d, 1H), 2.33 (s, 3H); FAB-MS (M+H)$^+$=339.

The starting material is prepared as follows:

1a) Triphenyl(pyridin-3-yl-methyl)phosphonium chloride

To an ice-cooled 2-phase mixture of 55.8 g (195 mmol) $Na_2CO_3$.10 $H_2O$ in 200 ml water and 100 ml toluene, 21.3 g (133 mmol) 3-chloromethylpyridine hydrochloride is added in portions. The mixture is stirred at 0° C. until a clear solution is obtained, the aqueous phase separated off, and the mixture extracted twice with 50 ml toluene. The toluene phases are dried ($Na_2SO_4$) and evaporated in the RE (10 mbar, 30° C.) to about half its original volume. To the yellowish solution, 68.1 g (259 mmol) triphenylphosphine is added and the mixture stirred for several days under a $N_2$ atmosphere at 70° C. The title compound is precipitated off in the process. It is filtered off and washed with toluene and hexane; $^1$H-NMR (DMSO-$_6$) 8.47 (m, 1H$^{Py}$), 8.18 (sb, 1H$^{Py}$), 7.91 (m, 3H), 7.72 (m, 12H), 7.37 (m, 1H$^{Py}$), 7.26 (m, 1H$^{Py}$), 5.33 (d, J=15 Hz, $H_2C$); FAB-MS (M-Cl)$^+$=354; an. calc. ($C_{24}H_{21}NClP$.0.17 $H_2O$) C, 73.36%; H, 5.47%; N, 3.56%; Cl, 9.02%; P, 7.88%; $H_2O$, 0.78%; meas. C, 73.11%; H, 5.43%; N, 3.82%; Cl, 9.49%; P, 7.98%; $H_2O$, 0.77%.

1b) 1-Chlorophthalazine hydrochloride

A suspension of 50 g (342 mmol) phthalazone, 1370 ml acetonitrile, 66 ml (0.72 mol) $POCl_3$ and 85 ml 4 N HCl in dioxane is stirred for 8 h at 50° C. The resulting solution is cooled to RT, evaporated to a volume of about 0.8 l and diluted with 1.2 l DIPE. Filtration and washing with DIPE yield the title compound: FAB-MS (M+H)$^+$=165/167.

1c) 1-(3-Methylanilino)phthalazine

Under a $N_2$ atmosphere, 30 g (149 mmol) 1-chlorophthalazine hydrochloride in 0.6 l n-butanol is mixed with 16.2 ml (149 mmol) m-toluidine and stirred for 1 h at 65° C. The solution is concentrated by evaporation and the residue distributed between dichloromethane/MeOH 10:1 and $Na_2CO_3$ solution (80 g in 0.5 l $H_2O$). The aqueous phase is extracted twice with dichloromethane/MeOH 10:1, the organic phases are washed with $Na_2CO_3$ solution (80 g in 0.5 l $H_2O$) and brine, dried ($Na_2SO_4$) and evaporated. The residue is taken up in 200 ml boiling dichloromethane/acetone 1:1, filtered hot, and partly evaporated. Then addition of DIPE leads to crystallization of the title compound, which is filtered off and washed with DIPE: m.p. 176-177° C.; $^1$H-NMR (DMSO-$d_6$) 9.12 (s, HN), 9.08 (s, 1H), 8.59 (m, 1H), 7.99 (m, 3H), 7.76 (s, 1H), 7.73 (d, 1H), 7.24 (t, 1H), 6.86 (d, 1H), 2.32 (s, 3H); FAB-MS (M+H)$^+$=236; an. calc. ($C_{15}H_{13}N_3$.0.05 $H_2O$) C, 76.28%; H, 5.59%; N, 17.79%; meas. C, 76.04%; H, 5.53%; N, 17.68%.

1d) 1-(3-Methylanilino)-4-([1,3,5]trioxan-2-yl)phthalazine

To a suspension of 9.6 g (40.8 mmol) 1-(3-methylanilino)phthalazine and 173 g 1,3,5-trioxane in 570 ml acetonitrile, 3.12 ml (40.8 mmol) trifluoroacetic acid, 11.0 ml (80% in $^tBuOO^tBu$; 87.4 mmol) $^tBuOOH$ and 190 mg (0.68 mmol) $FeSO_4$.7 $H_2O$ are added, and the mixture stirred for 17 h at 80° C. The cooled reaction mixture is partly evaporated in the RE, diluted with EtOAc and water and adjusted to an alkaline pH with 1 N NaOH. The aqueous phase is separated off and twice extracted with EtOAc. The organic phases are washed twice with water and brine, dried ($Na_2SO_4$) and evaporated. Column chromatography ($SiO_2$; EtOAc/toluene 1:3; applied as solution in dichloromethane/acetone 9:1) yields the title compound after crystallization with the addition of DIPE; m.p. 161° C.; DC (EtOAc/toluene 1:3) $R_f$=0.27; $^1$H-NMR (DMSO-$d_6$) 9.27 (s, HN), 8.74 (m, 1H), 8.61 (m, 1H), 8.00 (m, 2H), 7.72 (s, 1H), 7.68 (d, 1H), 7.25 (t, 1H), 6.89 (d, 1H), 6.39 (s, 1H), 5.47 (d, 2H), 5.41 (d, 2H), 2.33 (s, 3H); FAB-MS (M+H)$^+$=324; anal. calc. ($C_{18}H_{17}N_3O_3$) C, 66.86%; H, 5.30%; N, 13.00%; meas. C, 66.83%; H, 5.36%; N, 12.81%.

1e) 1-(3-Methylanilino)phthalazine-4-carbaldehyde

A suspension of 3.15 g (9.74 mmol) 1-(3-methylanilino)-4-([1,3,5]trioxan-2-yl)phthalazine in 150 ml $H_2SO_4$ (10% in $H_2O$) is stirred for 7 h at 100° C. The suspension is cooled to RT and adjusted to alkaline pH with NaOH (20% in $H_2O$), the title compound that precipitates out is filtered off and washed with water, $^1$H-NMR (DMSO-$d_6$) 10.17 (s, HCO), 9.84 (s, HN), 9.02 (d, 1H), 8.67 (d, 1H), 8.03 (m, 2H), 7.8-7.6 (2 sb, 2H), 7.30 (t, 1H), 6.98 (d, 1H), 2.36 (s, 3H); FAB-MS (M-H)$^+$=262.

Example 2

1-(3-Methylanilino)-4-[2-(pydridin-3-yl)ethyl]phthalazine

In a mixture of 12 ml EtOAc and 5 ml THF, 0.33 g (0.98 mmol) 1-(3-methylanilino)-4-[2-(pyridin-3-yl)vinyl]phthalazine (E/Z mixture) is hydrogenated in the presence of 0.1 g Pd/C (10%). Filtration via Celite, evaporation, column chromatography ($SiO_2$; EtOAc) and crystallization from ether yield the title compound: m.p. 136° C.; DC (EtOAc) $R_f$=0.15; $^1$H-NMR (DMSO-$d_6$, 120° C.) 8.66 (s, HN), 8.53 (m, 1H), 8.50 (s, 1H), 8.38 (dd, 1H), 8.15 (sb, 1H), 7.92 (sb, 2H), 7.69 (m, 3H), 7.26 (m, 1H), 7.22 (dd, 1 H), 6.85 (d, 1H), 3.53 (t, 2H), 3.22 (t, 2H), 2.36 (s, 3H); FAB-MS (M+H)$^+$=341; an. calc.($C_{22}H_{20}N_4$) C, 77.62%; H, 5.92%; N, 16.46%; meas. C, 77.30%; H, 6.10%; N, 16.34%.

Example 3

1-(3-Methylanilino)-4-[2-(pyridin-4-yl)vinyl]phthalazine

Under $N_2$ atmosphere, 58 mg NaH (60% in oil; 1.45 mmol) is washed 3 times with hexane, 2 ml DMSO is added, and the mixture heated for 30 min to 80° C. (gas evolution). At RT, 572 mg (1.32 mmol) triphenyl(pyridin-4-yl-methyl)

phosphonium bromide (preparation: P. Earsky, S. Hunig, I. Stemmler and D. Scheutzow, *Lieb. Ann. Chem.* 1980, 291) is added with 3 ml DMSO and the mixture stirred for 10 min. Then 350 mg (1.33 mmol) 1-(3-methylanilino)phthalazine-4-carbaldehyde (for preparation see Example 1e) is added to the reaction mixture and stirred at RT. After 3 h, the mixture is heated again for 30 min to 60° C., poured on water and extracted 3 times with EtOAc. The organic phases are washed three times with water and brine, dried ($Na_2SO_4$) and concentrated by evaporation. Column chromatography ($SiO_2$; toluene/acetone 2:1) yields an E/Z mixture (about 5:3) of the title compound; TLC (toluene/acetone 1:1) $R_f$=0.34; $HPLC_{20-100}$ $t_R$=5.7/6.1; $^1$H-NMR (DMSO-$d_6$) inter alia 9.24 and 9.19 (2s, 1H), 2.35 and 2.32 (2s, $H_3C$); FAB-MS $(M+H)^+$=339.

Example 4

1-(4-Chloro-3-trifluoromethylanilino)-4-[(2-(pyridin-3-yl)ethyl]phthalazine

A solution of 260 mg (0.96 mmol) 1-chloro-4-[2-(pyridin-3-yl)ethyl]phthalazine, 188 mg (0.96 mmol) 3-trifluoromethyl-4-chloroaniline in 3 ml ethanol and 0.24 ml 4 N HCl in dioxane is stirred for 2 h at 80° C. To the cooled reaction solution, 4.3 ml water and 0.93 ml sat. $NH_3$ solution are added, and the mixture is stirred for 3 h at RT. The title compound is filtered off and washed with a little acetonitrile and water: m.p. 164-167° C.; $^1$H-NMR (DMSO-$d_6$) 9.53 (s, HN), 8.57 (m, 3H), 8.35 (m, 3H), 8.02 (m, 2H), 7.77 (dt, 1H), 7.70 (d, 1H), 7.32 (dd, 1H), 3.55 (m, 2H), 3.18 (m, 2H); FAB-MS $(M+H)^+$=429.

The starting material is prepared as follows:

4a) Phthalazin-1(2H-one-4-carboxylic acid

A mixture of 400 g (3.12 mol) naphthalene and 96.05 g (0.695 mol) $K_2CO_3$ in 6.66 l water is heated to 60° C. A 75° C. solution of 2480 g (15.69 mol) $KMnO_4$ in 13.30 l water is added dropwise with occasional cooling (70° C.). Stirring is continued without heating until the exothermy subsides (about 2 h) and heating is then resumed for 5 h to 80° C. After cooling to RT, the mixture is filtered through Celite and the residue washed with water. To the slightly yellow, clear filtrate, 288 g (2.21 mol) hydrazine sulfate is added and the mixture heated for 2 h to 70° C. The cooled reaction solution is adjusted to pH 1 with conc. HCl solution, at which the product precipitates out. Cooling to 15° C., filtration via a nutsch filter and washing with water yield the title compound, m.p. 256-257° C.; $^1$H-NMR (DMSO-$d_6$) 8.57 (d, 1H), 8.30 (d, 1H), 7.95 (m, 2H); FAB-MS $(M+H)^+$=191.

4b) 4-Hydroxymethylphthalazin-1 (2H)-one

With the exclusion of moisture, a solution of 155 ml (1.19 mol) isobutyl chloroformate in 620 ml THF is added dropwise to a suspension of 207 g (1.089 mol) phthalazin-1(2H-one-4-carboxylic acid in 6 l THF and 166 ml (1.188 mol) triethylamine at about 10° C. After stirring for 3 h at RT, the mixture is filtered and the residue washed with 0.5 l THF. The yellow filtrate is cooled to 15° C., then 93 g (2.46 mol) sodium borohydride is added and the suspension stirred for about 8 h at RT. To complete the reduction, another 10 g sodium borohydride is added and the mixture heated for 5 h to 40° C. Then 0.5 l water and finally 0.5 l of 5 N HCl are added dropwise at 15° C. and the turbid solution is stirred for 30 min. The reaction mixture is diluted with 3 l EtOAc and 2 l semisaturated brine, the aqueous phase is separated off and extracted 3 times with 2 l EtOAc. The organic phases are washed twice each time with semisaturated brine and brine, dried ($Na_2SO_4$) and concentrated by evaporation. Stirring in water at 90° C., cooling and filtration yield the title compound; m.p. 199-201° C.; $^1$H-NMR (DMSO-$d_6$) 12.52 (s, HN), 8.25 (d, 1H), 8.11 (d, 1H), 7.9 (m, 2H), 5.49 (t, HO), 4.68 (d, 2H); FAB-MS $(M+H)^+$=177.

4c) Phthalazin-1(2H)-one-4-carbaldehyde

Under $N_2$ atmosphere, 50 g (284 mmol) 4-hydroxymethylphthalazin-1(2H)-one is dissolved in 900 ml DMSO and 119 ml (851 mmol) triethylamine. A solution of 90.3 g (567 mmol) sulfur trioxide pyridine complex in 733 ml DMSO is added and the mixture stirred for about 2 h. After the reaction is completed (TLC control), the mixture is poured onto a mixture of 2 l 5% $Na_2CO_3$ solution with 2 kg ice and 5 l EtOAc and then stirred. The aqueous phase of the resulting suspension is separated off and twice extracted with 2 l EtOAc. The first organic phase comprises crystalline product, this is filtered off and washed with water and EtOAc. The organic phase is separated off from the filtrate and, together with the second and third organic phase, washed with water and brine, dried ($Na_2SO_4$) and evaporated. The evaporation residue is combined with the above crystalline product, stirred in EtOAc, and hexane added before being filtered. This yields the title compound; m.p. 262-265° C.; $^1$H-NMR (DMSO-$d_6$) 9.82 (s, HCO), 8.88 (d, 1H), 8.27 (d, 1H), 7.95 (m, 2H); FAB-MS $(M+H)^+$=175, $(M+H+MeOH)^+$=207.

4d) E/Z-4-[2-(Pyridin-3-yl)vinyl]phthalazin-1(2H)-one

Under $N_2$ atmosphere, 723 mg NaH (60% in oil; 18.1 mmol) is washed twice with hexane, 21 ml DMSO is added, and the mixture heated for 20 min to 70° C. (gas evolution). After cooling to RT, the mixture is diluted with 15 ml DMSO, 6.71 g (17.2 mmol) triphenyl(pyridin-3-yl-methyl) phosphonium chloride (for preparation, see 1a) is added in portions, and the blackish-yellow solution is stirred for 10 min (Wittig reagent). A second flask is prepared with 3.0 g (17.2 mmol) phthalazin-1(2H)-one-4-carbaldehyde in 39 ml DMSO under an inert gas. The above Wittig reagent is added and a little DMSO is then rinsed in. After stirring for 75 min at RT, the mixture is poured onto water/EtOAc, the aqueous phase separated off and extracted again twice with EtOAc. The organic phases are washed with water and brine, combined and extracted twice with 1 N HCl and then discarded. The acidic aqueous phases are immediately adjusted to alkaline pH with sat. $Na_2CO_3$ solution and extracted three times with EtOAc. The organic phases are washed with water and brine, dried ($Na_2SO_4$) and concentrated by evaporation. This yields the title compound as an E/Z mixture: TLC (EtOAc) $R_f$=0.18/0.22; $HPLC_{5-40}$ $t_R$=9.2/9.6; FAB-MS $(M+H)^+$=250.

4e) 4-[2-(Pyridin-3-yl)ethyl]phthalazin-1 (2H)-one

Hydrogenation of 2.66 g (10.7 mmol) E/Z-4-[2-(pyridin-3-yl)vinyl]phthalazin-1(2H)-one in 70 ml methanol/THF 1:1 in the presence of 0.5 g Pd/C 10% results in a clear solution. Filtration of the catalyst through Celite and evaporation yields the title compound:. TLC (EtOAc) $R_f$=0.13; HPLC$_{5-40}$ t$_R$=9.1; $^1$H-NMR (CDCl$_3$) 10.40 (s, HN), 8.55 (d, 1H), 8.48 (m, 2H), 7.81 (m, 3H), 7.57 (dt, 1H), 7.22 (m, 1H), 3.26 (m, 2H), 3.13 (m, 2H); FAB-MS. (M+H)$^+$=252.

4f) 1-Chloro-4-[2-(pyridin-3-yl)ethyl]phthalazine

Under exclusion of air, 2.4 g (9.55 mmol) 4-[2-(pyridin-3-yl)ethyl]phthalazin-1(2H)-one in 36 ml acetonitrile is mixed with 2.18 ml (23.8 mmol) phosphoryl chloride and 4.75 ml 4 N HCl in dioxane and stirred for 3.5 h at 60° C. After cooling to RT, the product is filtered off as hydrochloride and washed with CH$_3$CN. The crystals are dissolved in about 10 ml H$_2$O, mixed with 15 ml H$_2$O and 1.5 ml sat. NH$_3$ solution and extracted immediately 3 times with EtOAc. Drying (Na$_2$SO$_4$) of the organic phases and evaporation yield the title compound; FAB-MS (M+H)$^+$=270.

Example 5

The following compounds can be prepared by analogy with the above methods:

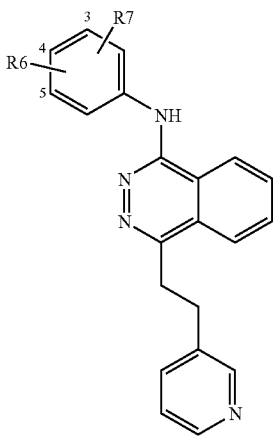

| Example | R6 | R7 | FAB-MS | m.p. [° C.] |
|---|---|---|---|---|
| 5a | 4-Chloro | H | 361 | |
| 5b | 4-n-Propyl | H | | |
| 5c | 3-i-Propyl | H | | |
| 5d | 3-Methyl | 4-Methyl | | |
| 5e | 3-Iodo | 4-Methyl | | |
| 5f | 4-i-Propyl | H | 369 | 148-150 |
| 5g | 3-Methoxy | 4-Methyl | | |
| 5h | 4-t-Butyl | H | 383 | 150-152 |
| 5i | 3-Methyl | 4-i-Propyl | 383 | 162-164 |
| 5j | 3-Trifluoromethyl | 4-Iodo | | |
| 5k | 3-t-Butyl | H | 383 | |
| 5l | 3-Bromo | 4-Methyl | 419/421 | |
| 5m | 3-Trifluoromethyl | 4-Bromo | | |
| 5n | 3-Ethyl | H | | |
| 5o | 3-Methyl | 5-Methyl | 355 | |
| 5p | 3-Trifluoromethyl | 4-Trifluoromethyl | 463 | 139-141 |
| 5q | 3-Trifluoromethyl | 5-Bromo | 473/475 | 189-190 |
| 5r | 3-Bromo | H | 405/407 | 182-183 |
| 5s* | 3-Trifluoromethyl | 5-Chloro | 429 | |
| 5t | 3-Trifluoromethyl | H | 395 | 179-181 |
| 5u | 3-Trifluoromethyl | 5-Trifluoromethyl | 463 | |
| 5v | 3-Trifluoromethyl | 5-Fluoro | | |
| 5w | 4-Trifluoromethyl | H | | |
| 5x | 3-Bromo | 4-Ethyl | 433/435 | 128-130 |

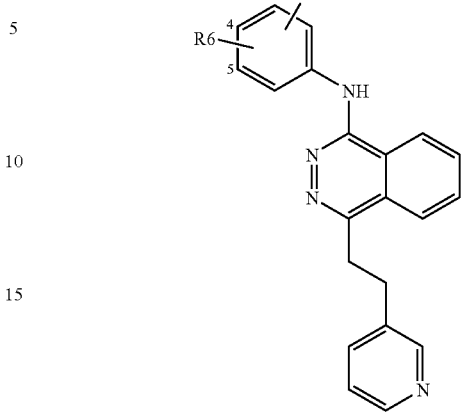

| Example | R6 | R7 | FAB-MS | m.p. [° C.] |
|---|---|---|---|---|
| 5y | 3-Chloro | 4-Methyl | 375 | 144-146 |
| 5z | 3-Trifluoromethyl | 4-Chloro | 429 | |

*Starting materials are prepared as follows:
5a) 5-Chloro-3-trifluoromethylnitrobenzene
(see also EP 0516 297 A1) To a brown solution of 90 g (374 mmol) 4-amino-3-chloro-5-nitrobenzenetrifluoride (Maybridge; Tintagel/England) in 500 ml ethanol, 56.7 ml sulfuric acid 96% (exothermic) is added dropwise over a period of 30 min. After the mixture has been heated to 75° C., 64.53 g (935 mmol) sodium nitrite is added in portions over a period of 1 h (gas evolution). After stirring for 2.5 h at 75° C., it is cooled to RT. The reaction mixture is poured onto 1.5 l ice-water and extracted four times with ether. Washing of the organic phases with 0.1 N HCl, sat. NaHCO$_3$ solution and brine, drying (Na$_2$SO$_4$), and evaporation yield a brown oil. Column chromatography (SiO$_2$; hexane) yields the title compound as oil: $^1$H-NMR (DMSO-d$_6$) 8.62 (m, 1H), 8.46 (m, 2H), FAB-MS (M − NO$_2$)$^+$ = 179.
5b) 5-Amino-3-chlorobenzotrifluoride
In the presence of 10.17 g Raney nickel, 92 g (0.408 mol) 5-chloro-3-trifluoromethyl-nitrobenzene is hydrogenated in 1 l methanol. The reaction mixture is filtered through Celite/activated carbon and the residue washed with methanol. Evaporation of the filtrate yields the oily title compound. $^1$H-NMR (DMSO-d$_6$) 6.80 (m, 3H), 5.92 (s, H$_2$N); FAB-MS (M + H)$^+$ = 196.

Example 6 trans and cis 1-(4-tert.-Butylcyclohexylamino)-4-[(2-(pyridin-3-yl)ethyl]phthalazine Under N$_2$-atmosphere, 500 mg (1.85 mmol) 1-chloro-4-[2-(pyridin-3-yl)ethyl]phthalazine and 1.25 g (8 mmol) of 4-tert.-butylcyclohexylamin (trans/cis mixture) are heated at 150° C. for 2.5 h. The reaction mixture is diluted with ethyl acetate, water and conc. NH$_3$-solution (=1 ml), then the aqueous layer is separated off and extracted 2× with ethyl acetate. The organic phases are washed twice with water and brine, dried (Na$_2$SO$_4$) and concentrated. Chromatography (SiO$_2$; ethyl acetate to ethyl acetate/ethanol 10:1) yields the trans isomer followed by the cis isomer of the title compound. trans 1-(4-tert.-Butylcyclohexylamino)-4-[(2-(pyridin-3-yl)ethyl]phthalazine: m.p. 155-157° C.; $^1$H-NMR (DMSO-d$_6$) 8.50 (s, 1H), 8.38 (d, 1H), 8.35 (d, 1H), 8.06 (d, 1H), 7.83 (m, 2H), 7.74 (d, 1H), 7.30 (m, 1H), 6.89 (d, HN), 4.08 (m, 1H), 3.38 (t, 2H), 3.10 (t, 2H), 2.12 (m, 2H), 1.81 (m, 2H), 1.35 (q, 2H), 1.14 (q, 2H), 1.07 (m, 1H), 0.88 (s, 9H); FAB-MS (M+H)$^+$=389. cis 1-(4-tert.-Butylcyclohexylamino)-4-[(2-(pyridin-3-yl)ethyl]phthalazine: $^1$H-NMR (DMSO-d$_6$) 8.48 (m, 2H), 8.38 (d, 1H), 8.08 (m, 1H), 7.84

(m, 2H), 7.73 (m, 1H), 7.29 (m, 1H), 6.49 (d, HN), 4.33 (sb, 1H), 3.39 (m, 2H), 3.10 (m, 2H), 2.18 (d, 2H), 1.6-1.4 (m, 6H), 1.06 (m, 1H), 0.87 (s, 9H); FAB-MS (M+H)+-=389.

Example 7

By Heating 1-chloro-4-[2-(pyridin-3-yl)ethyl]phthalazine with an Excess of 3-chlorobenzylamine, it is Possible to Prepare 1-(3-chlorobenzylamino)-4-[2-pyridin-3-yl)ethyl]phthalazine:

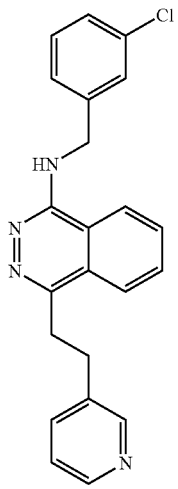

Example 8

1-(4-Chloro-3-trifluoromethylanilino)-4-[3-(pyridin-3-yl)propyl]phthalazine

A solution of 321 mg (1.13 mmol) 1-chloro-4-[3-(pyridin-3-yl)propyl]phthalazine, 243 mg (1.24 mmol) 3-trifluoromethyl-4-chloroaniline in 6 ml ethanol and 0.28 ml 4 N HCl in dioxane is stirred for 100 min at 60° C. The cooled reaction solution is poured onto a mixture of 2 ml sat. NH$_3$ solution and 20 ml water and extracted immediately 3 times with EtOAc. The organic phases are washed with water and brine, dried (Na$_2$SO$_4$) and concentrated by evaporation. Column chromatography (SiO$_2$; EtOAc/acetone 9:1) and stirring in EtOAc/DIPE yield the title compound: m.p. 165-166° C.; TLC (EtOAc/acetone 9:1) R$_f$=0.21; $^1$H-NMR (DMSO-d$_6$) 9.50 (s, HN), 8.58 (m, 2H), 8.47 (s, 1H), 8.39 (dd, 1H), 8.33 (dd, 1H), 8.16 (d, 1H), 8.01 (m, 2H), 7.67 (m, 2H), 7.30 (dd, 1H), 3.22 (t, 2H), 2.76 (t, 2H), 2.11 (quint., 2H); FAB-MS (M+H)+=443; an. calc. (C$_{23}$H$_{18}$N$_4$ClF$_3$) C, 62.38%; H, 4.10%; N, 12.65%; Cl, 8.01%; F, 12.87%; meas. C, 62.41%; H, 4.07%; N, 12.58%; Cl, 7.99%; F, 12.84%.

The starting material is prepared as follows:

8a) 3-(Pyridin-3-yl)propan-1-one

A mixture of 6.08 g (20 mmol) (formylmethylene)triphenylphosphorane (Fluka; Buchs/Switzerland) and 2.14 g (20 mmol) freshly distilled 3-pyridinecarbaldehyde in 200 ml benzene is stirred for 3 h at 80° C. After the addition of a further 0.30 g (formylmethylene)triphenylphosphorane, the mixture is stirred for another 3 h at 80° C. The cooled benzene solution is extracted with 250 ml, 100 ml and finally 50 ml 0.1 N HCl. The acidic H$_2$O phases are finally extracted with 150 ml ether and the organic phases discarded. The combined acidic H$_2$O phases are covered with a supernatant 150 ml ether and adjusted to alkaline pH with 100 ml 1 N NaOH. The H$_2$O phase is separated off and extracted 3 times with 150 ml EtOAc each time. Drying (Na$_2$SO$_4$) and partial evaporation of the organic phases yield 0.4 l of a solution of 3-(pyridin-3-yl)propen-1-one in EtOAc. Hydrogenation of the above solutions in the presence of 5% Pd/C, filtration of the catalyst, evaporation and column chromatography (SiO$_2$; EtOAc) yield the title compound; TLC (EtOAc) R$_f$=0.30; FAB-MS (M+H)+=136.

8b) E/Z-3-[3-(Pyridin-3-yl)propylidene]isobenzofuran-1(3H)-one

Under N$_2$ atmosphere, 0.87 g (6.44 mmol) 3-(pyridin-3-yl)propan-1-one is dissolved in 14 ml THF and mixed with 2.78 g (6.44 mmol) 1,3-dihydro-3-oxo-1-isobenzofuranyltriphenylphosphonium chloride (for preparation: H. Kunzek and K. Rühlmann, *J. Organomet. Chem.* 1972, 42, 391) and 0.90 ml (6.44 mmol) triethylamine at 0° C. After 3 h at 0° C., filtration is carried out, and the residue is washed with EtOAc and discarded. The filtrate is evaporated and chromatographed (SiO$_2$; EtOAc/toluene 1:1). This yields an E/Z mixture of title compound contaminated with a little triphenylphosphine oxide; TLC (hexane/EtOAc 1:2) R$_f$=0.15; FAB-MS (M+H)+=252.

8c) 4-[2-(Pyridin-3-yl)propyl]phthalazin-1(2H)-one

An emulsion of 1.2 g (4.8 mmol) E/Z-3-[3-(pyridin-3-yl)propylidene]isobenzofuran-1(3H)-one and 15 ml hydrazine hydrate in 15 ml THF is stirred for 2 h at 80° C. (oil dissolves). The cooled reaction mixture is diluted with 50 ml EtOAc, the aqueous phase separated off, extracted twice with 50 ml EtOAc and discarded. The organic phases are extracted 3 times with 20 ml 1 N HCl and likewise discarded. The combined HCl extracts are adjusted to alkaline pH with 1 N NaOH and extracted 3 times with 50 ml EtOAc each time. Drying (Na$_2$SO$_4$) and evaporation of the organic phases yield, after crystallization from EtOAc/DIPE, the title compound; m.p. 142° C.; $^1$H-NMR (CDCl$_3$) 10.45 (s, HN), 8.47 (m, 3H), 7.8 (m, 3H), 7.53 (dt, 1H), 7.22 (dd, 1H), 2.98 (t, 2H), 2.77 (t, 2H), 2.15 (quin., 2H); FAB-MS (M+H)+=266; anal. calc. (C$_{16}$H$_{15}$N$_3$O) C 72.43%, H 5.70%, N 15.84%; meas. C 72.04%, H 5.68%, N 15.47%.

8d) 1-Chloro-4-[3-(pyridin-3-yl)propyl]phthalazine

Under exclusion of air, 771 mg (2.9 mmol) 4-[3-(pyridin-3-yl)propyl]phthalazin-1(2H)-one in 14 ml acetonitrile is mixed with 1.11 g (7.25 mmol) phosphoryl chloride and 1.45 ml 4 N HCl in dioxane and stirred for 36 h at 45° C. Then 50 ml water is added, the reaction mixture adjusted to alkaline pH with sat. Na$_2$CO$_3$ solution and immediately extracted 3 times with EtOAc. Drying (Na$_2$SO$_4$) of the organic phases and evaporation yield the title compound; FAB-MS (M+H)+=284.

Example 9

The following compounds are prepared in a manner analogous to that described in Example 8:

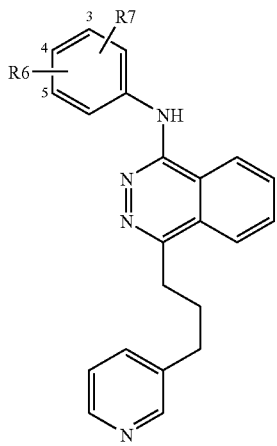

| Example | R6 | R7 | m.p. |
|---|---|---|---|
| a | 4-Chloro | H | 129-130° C. |
| b | 3-Chloro | 5-Trifluoromethyl | 178° C. |
| c | 4-$^t$Butyl | H | 180° C. |
| d | 4-Chloro | 3-Trifluoromethyl | |

Example 10

Test for Activity Against Flt-1 VEGF-receptor Tyrosine Kinase

The test is conducted using Flt-1 VEGF-receptor tyrosine kinase, as described hereinabove. The $IC_{50}$ values determined are given below, insofar as they have been accurately determined:

| Title compound from Example | $IC_{50}$ (µmol) |
|---|---|
| 1 (E isomer) | 0.715 |
| 1 (Z isomer) | 4.9 |
| 2 | 0.317 |
| 31D | 1.46 |

Example 11

Soft Capsules 5000 soft gelatin capsules, each comprising as active ingredient 0.05 g of one of the compounds of formula I mentioned in the preceding or subsequent Examples, are prepared as follows:

| Composition | |
|---|---|
| Active ingredient | 250 g |
| Lauroglycol | 2 liter |

Preparation process: The pulverized active ingredient is suspended in Lauroglykol® (propylene glycol laurate, Gattefossé S. A., Saint Priest, France) and ground in a wet pulverizer to produce a particle size of about 1 to 3 µm. Then 0.419 g portions of the mixture are introduced into soft gelatin capsules using a capsule-filling machine.

Example 12

As described in or in analogy to the methods described in the present disclosure or of the disclosure of WO 98/35958, or in the Examples hereinbefore and hereinafter, the following compounds are prepared:

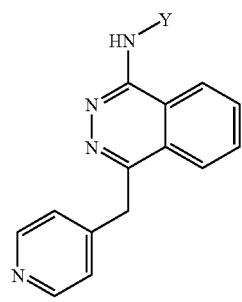

| Example | $H_2N-Y$ | $\overset{Y}{\underset{H}{N}}\diagup$ | m.p. [° C.] | An. meas.[9] | FAB MS $(M + H)^+$ |
|---|---|---|---|---|---|
| 12A | (2-ethyl-6-methylaniline) | (N-methyl-2-ethyl-6-methylaniline) | | | |

-continued

| Example | H$_2$N—Y | -Y) | m.p. [°C.] | An. meas.[9] | FAB MS (M + H)$^+$ |
|---|---|---|---|---|---|
| 12B | 3-aminophenylurea [2] | N-methyl analog | | | |
| 12C | 4-methyl-3-methoxyaniline [3] | N-methyl analog | 158-160 | CHN | 357 |
| 12D | 3-(trifluoromethylthio)aniline [4] | N-methyl analog | 200-201 | CHN | 413 |
| 12E | 4-chloro-3-(trifluoromethylsulfonyl)aniline [5] | N-methyl analog | | | |
| 12F | 4-amino-N-methylbenzamide [6] | N-methyl analog | | | 370 |
| 12G | 3-(1H-pyrazol-3-yl)aniline [6] | N-methyl analog | 236-237 | CHN | 379 |
| 12H | 3-(1-methyl-1H-pyrazol-3-yl)aniline [6] | N-methyl analog | 241-243 | CHN | 393 |

-continued
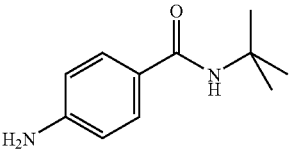
| Example | H₂N—Y | 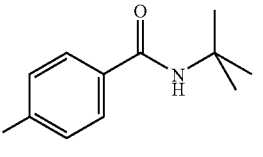 | m.p. [° C.] | An. meas.[9] | FAB MS (M + H)⁺ |
|---|---|---|---|---|---|
| 12I | 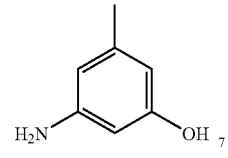 [6] | 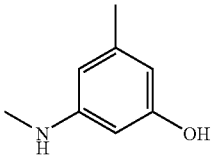 | | | |
| 12J | 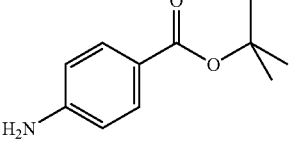 [7] | 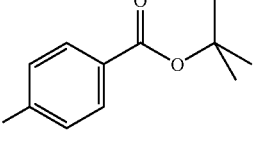 | | | |
| 12K | 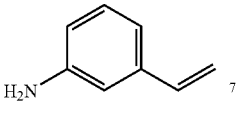 | 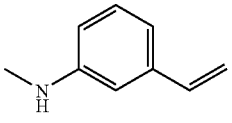 [6] | 217-219 | | 413 |
| 12L | 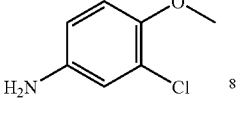 [7] | 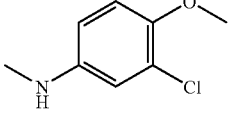 | | | |
| 12M | 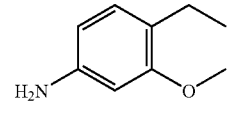 [8] | 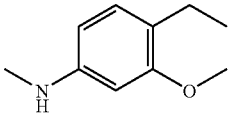 | 195-197 | | |
| 12N | 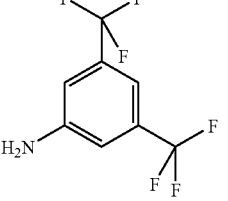 | | | | |
| 12O | 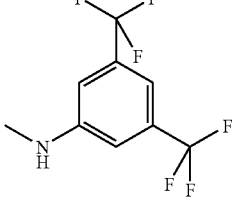 [1] | | | | 449 |
Provider: [1]Fluka; [2]Bayer; [3]Merck; [4]JRD Fluorochemicals; [5]Maybridge; [6]Butt Park; [7]ICN; [8]Aldrich; [9]within ±0.4% of the calculated values

Example 13

1-(5-Chloro-3-trifluormethyl-anilino)-4-(4-pyridyl-methyl)-phthalazine

A suspension of 27.9 g (109 mMol) of 1-chloro-4-(4-pyridyl-methyl)-phthalazine (Example 67A.1 in WO 98/35958) and 21.4 g (109 mMol) of 5-amino-3chloro-benzotrifluoride (Example 5b) in 500 ml of ethanol and 27.4 ml of 4 N HCl/dioxane is stirred during 3 h a 80° C. After cooling down, the reaction mixture is diluted with 0.3 l of ether, filtrated, and washed with ether. The remaining solid is then taken up in water and EtOAc, brought to alkaline pH by means of $NH_3$ solution, stirred for 15 min at room temperature and then filtered and washed with ether (→raw product). The water layer is removed from the filtrate and extracted twice with ethyl acetate. The organic layers are washed with water and brine, dried over $Na_2SO_4$ and evaporated. The residue is combined with the raw product mentioned above, and the solid is dissolved in ethyl acetate and methanol. About 100 g $SiO_2$ are added, followed by evaporation, and the powder is applied onto a silica gel column and eluted with ethyl acetate and subsequently with a mixture of ethyl acetate and methanol (98:2→95:5, v/v). Solving the obtained fractions in ethyl acetate/methanol, partial evaporation and crystallization by addition of ether/hexane leads to the title compound: m.p. 231-232° C.; An. calc. ($C_{21}H_{14}N_4ClF_3$) C, 60.81%; H, 3.40%; N, 13.51; %; Cl, 8.55%; F, 13.74%; An meas. C, 60.8%; H, 3.4%; N, 13.5%; Cl, 8.5%; F, 13.8%; $^1$H-NMR (DMSO-$d_6$) 9.63 (s, HN), 8.60 (d, 1H), 8.56 (s, 1H), 8.44 (d, 2H), 8.39 (s, 1H), 8.16 (d, 1H), 8.03 (t, 1H), 7.97 (t, 1H), 7.43 (s, 1H), 7.32 (d, 2H), 4.63 (s, 2H); FAB-MS (M+H)$^+$=415.

Example 14

In analogy to Example 13, the following compounds of the formula I are obtained (some are isolated as salt; salts are marked in the table):

| Example | $H_2N$—Y | product | m.p. [° C.] | An. meas.[1] | FAB MS (M + H)$^+$ |
|---|---|---|---|---|---|
| 14a | 3-chloro-4-methylaniline | | 229-231 | CHN | 361 |
| 14b | dimethyl 5-aminoisophthalate | | | CHN | 429 |
| 14c | 2,3-bis(trifluoromethyl)aniline | | 203-204 | CHN | 449 |

-continued
| Example | H₂N—Y | 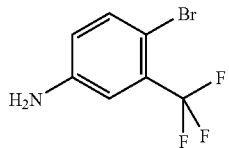 | m.p. [° C.] | An. meas.[1] | FAB MS (M + H)⁺ |
|---|---|---|---|---|---|
| 14d | 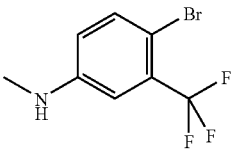 | 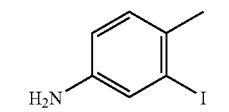 | | | 459/461 |
| 14e | 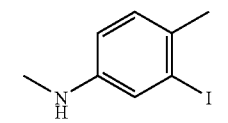 | 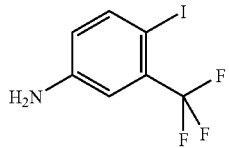 | 183-186 | | 453 |
| 14f | 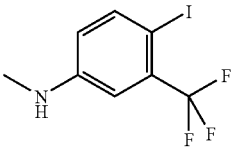 | 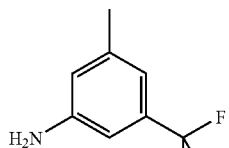 | | | 507 |
| 14g | 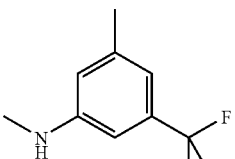 | 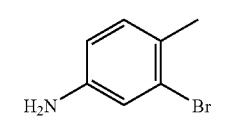 | | CHNIF | 507 |
| 14h | 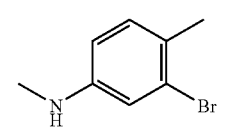 | 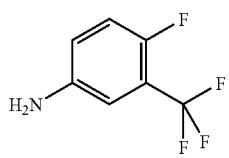 | 220-221 | CHNBr | 405/407 |
| 14i | 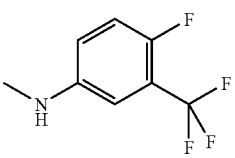 | 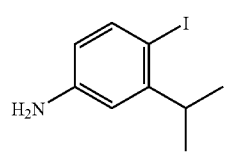 | 196-199 | | 399 |
| 14j | 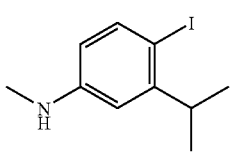 | | | | 481 |

-continued

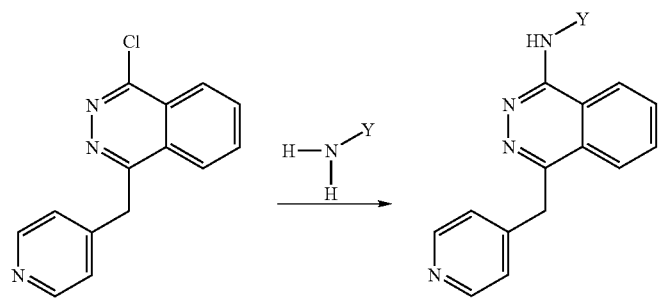

| Example | H₂N—Y | Y) | m.p. [°C] | An. meas.[1] | FAB MS (M + H)⁺ |
|---|---|---|---|---|---|
| 14k[2] | 3-isopropyl-5-methylaniline (H₂N-Ar) | N-methyl-3-isopropyl-5-methylaniline | | CHN | 369 |
| 14l | 3-methyl-5-(trifluoromethyl)aniline | N-methyl-3-methyl-5-(trifluoromethyl)aniline | | CHNF | 395 |
| 14m[2] | 4-bromo-3-isopropylaniline | N-methyl-4-bromo-3-isopropylaniline | | CHN | 433/435 |
| 14n | 4-bromo-3-propylaniline | N-methyl-4-bromo-3-propylaniline | | | 433/435 |
| 14o | 3-bromo-5-(2,2,2-trifluoroethyl)aniline | N-methyl-3-bromo-5-(2,2,2-trifluoroethyl)aniline | 229 | CHNBrF | 473/474 |
| 14p | 6-aminoquinoline | N-methyl-6-aminoquinoline | | | 364 |

| Example | H$_2$N—Y | | m.p. [°C] | An. meas.[1] | FAB MS (M + H)$^+$ |
|---|---|---|---|---|---|
| 14q[3] | 4-ethyl-3-bromo-aniline (H$_2$N–C$_6$H$_3$(Br)(Et)) | N-methyl-4-ethyl-3-bromo-aniline | 143–144 | CHNBr | 419/421 |
| 14r[3] | 4-tert-butyl-3-bromo-aniline | N-methyl-4-tert-butyl-3-bromo-aniline | 173–174 |  | 447/449 |
| 14s[3,4] | 4-amino-2-bromo-benzoic acid | N-methyl-4-amino-2-bromo-benzoic acid |  | CHNBrFO | 435/437 |
| 14t[5] | methyl 4-amino-2-bromo-benzoate | methyl N-methyl-4-amino-2-bromo-benzoate | 182–183 |  | 449/451 |
| 14r | 4-amino-2-bromo-benzyl alcohol | N-methyl-4-amino-2-bromo-benzyl alcohol |  |  |  |

[1] within ±0.4% of the calculated values
[2] isolated as salt (HCl)
[3] the starting material is obtained as follows:
14q.1) 3-Bromo-4-ethyl-aniline
Hydrogenation of 4.45 g (19 mMol) 3-bromo-4-ethyl-nitrobenzene (Macromolecules 1995, 28, 5618) in 100 ml ethanol in the presence of 1 g Raney-nickel gives, after filtration, concentration and chromatography (SiO$_2$; dichloromethane), the title compound: FAB-MS (M + H)$^+$ = 201.
14r.1) 3-Bromo-4-tert.butyl-aniline
Hydrogenation of 3-bromo-4-tert.butyl-nitrobenzene (Maybridge) as described in expl. 14q.1)
14s.1) 4-Amino-2-bromo-4-benzoic acid
Hydrogenation of 2-bromo-4-nitrobenzoic acid (Specs) as described in expl. 14q.1)
[4] isolated as salt (2 CF$_3$COOH)
[5] MeOH as solvent

Example 15

1-[(2,6-Dimethyl-pyrimidin-4-yl)-amino]4-(4-pyridyl-methyl)-phthalazine

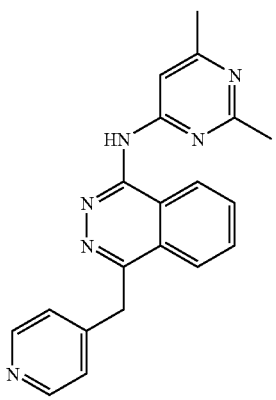

To a suspension of 308 mg (2.5 mMol) of 4-amino-2,6-dimethyl-pyrimidine and 694 mg (2.0 mMol) of 1-iodo-4-(4-pyridyl-methyl)-phthalazine in 20 ml of toluene, 415 mg (3.0 mMol) of $K_2CO_3$ and 231 mg (0.20 mMol) of tetrakis-(triphenylphosphin)-palladium are added, and the mixture is stirred during 1 h at RT and then 17 h at 110° C. The hot reaction mixture is filtrated, the remaining solid washed out with toluene and petrol ether and discarded. From the filtrate, product crystallizes after cooling. Filtration, washing with toluene/petrol ether and recrystallization from boiling dioxane yields the title compound: m.p 232-233° C.; An. calc.($C_{20}H_{18}N_6 \cdot 0.10\ H_2O$) C, 69.79%; H, 5.33%; N, 24.42%; $H_2O$, 0.52%; An. meas. C, 69.78%; H, 5.32%; N, 24.20%; $H_2O$, 0.5%; FAB-MS $(M+H)^+$=343.

The starting material is prepared as follows:

15a) 1-Iodo-4-(4-pyridyl-methyl)-phthalazine

Under exclusion of air, a suspension of 12.8 g (50 mMol) of 1-chloro-4-(4-pyridyl-methyl)-phthalazine (Example 67A.1 in WO 98/35958) and 25 g (166.8 mMol) of sodium-iodide in 0.3 l of acetone is mixed with 20 ml hydroiodic acid (55% HI in water; 144 mMol) and stirred in the dark during 6 days at RT. Filtration and washing with acetone follow. The remaining solid is suspended in 1 l of water, neutralized with 100 ml of an 1 M $Na_2CO_3$ solution, stirred during 10 min, filtered and washed with water, yielding the title compound: An. calc. ($C_{14}H_{10}N_3I \cdot 0.05\ H_2O$) C, 48.31%; H, 2.92%; N, 12.07%; I, 36.46%; $H_2O$, 0.26%; An. meas. C, 48.60%; H, 3.10%; N, 12.08%; I, 36.28%; $H_2O$, 0.28%; FAB-MS $(M+H)^+$=348.

Example 16

In analogy to the procedure described in Example 15, the following compounds of the formula I are obtained (some are isolated as salt; salts are marked in the table):

| Example | $H_2N$—Y | [structure] | m.p. [° C.] | An. meas.[1] | FAB MS $(M + H)^+$ |
|---|---|---|---|---|---|
| 16a | [2-aminopyrimidine] | [N-methyl pyrimidine] | 177-178 | CHN | 329 |
| 16b | [4-tert-butyl-6-aminopyrimidine] | [4-tert-butyl-6-(methylamino)pyrimidine] | 181 | CHN | 371 |

-continued
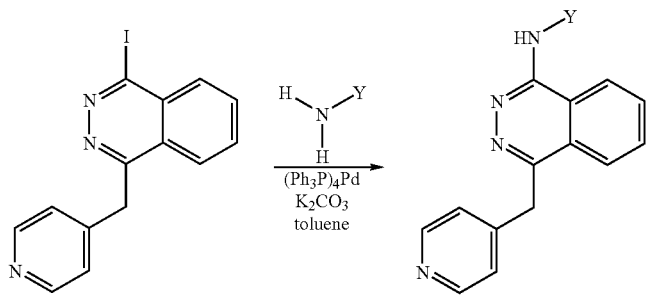
| Example | H$_2$N—Y | $\underset{H}{\overset{Y}{\underset{|}{N}}}$ | m.p. [°C.] | An. meas.[1] | FAB MS (M + H)$^+$ |
|---|---|---|---|---|---|
| 16c | | | 155 | CHN | 328 |
| 16d | | | 125 | CHN | 328 |
| 16e | | | 271-272 | CHNS | |
| 16f | | | 143-145 | CHNF | 382 |
| 16g | | | | | 344 |
| 16h[2] | | | | CHNF | 342 |
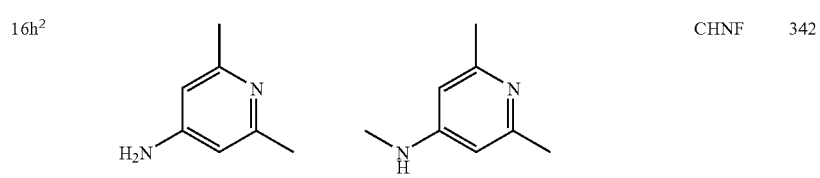

| Ex-ample | H₂N—Y | ![structure] | m.p. [°C.] | An. meas.[1] | FAB MS (M + H)⁺ |
|---|---|---|---|---|---|
| 16i | 5-bromo-2-aminopyridine | N-methyl derivative | | | 392/394 |
| 16j | 6-chloro-3-aminopyridine | N-methyl derivative | | | 348 |
| 16k | 2-amino-4,6-dimethylpyridine | N-methyl derivative | | | 342 |

[1] within ±0.4% of the calculated values
[2] isolateted as CF₃COOH-salt

Example 17

1-(3,5-Dimethylanilino)-4-(4-pyridylmethyl)-6-methyl-phthalazine and 1-(3,5-dimethylanilino)-4-(4-pyridylmethyl)-7-methyl-phthalazine A mixture of 440 mg (1.63 mmol) 1-chloro-4-(4-pyridylmethyl)-6-methyl-phthalazine and 1-chloro-4-(4-pyridylmethyl)-7-methyl-phthalazine, 208 mg (1.71 mmol) 3,5-dimethylaniline, 60 ml ethanol and 0.40 ml HCl (4 N in dioxane) is heated for 3 h to 80° C. At RT, the solution is poured onto 150 ml of water and 4.5 ml of a 25-% NH₃-solution. Then the precipitated product is filtered off and washed with water yielding the title compounds as an about 2:3 mixture: An. calc. ($C_{23}H_{22}N_4$. 0.65 $H_2O$): C 75.44%, H 6.41%, N 15.30%; An. meas. C 75.34%, H 6.45%, N 14.95%; ¹H NMR (DMSO-d₆) δ 6-methyl derivative:8.91 (s, HN), 8.49 (d, HC), 8.43 (d, 2HC), 7.90 (s, HC), 7.78 (d, HC), 7.57 (s, 2HC), 7.31 (d, 2HC), 6.66 (s, HC), 4.53 (s, $H_2C$), 2.51 (s, $H_3C$), 2.28 (s, 2$H_3C$), δ 7-methyl derivative:8.87 (s, HN), 8.43 (d, 2HC), 8.41 (s, HC), 7.97 (d, HC), 7.72 (d, HC), 7.59 (s, 2HC), 7.28 (d, 2HC), 6.66 (s, HC), 4.53 (s, $H_2C$), 2.55 (s, $H_3C$), 2.28 (s, 2$H_3C$); FAB MS (M+H)⁺=355.

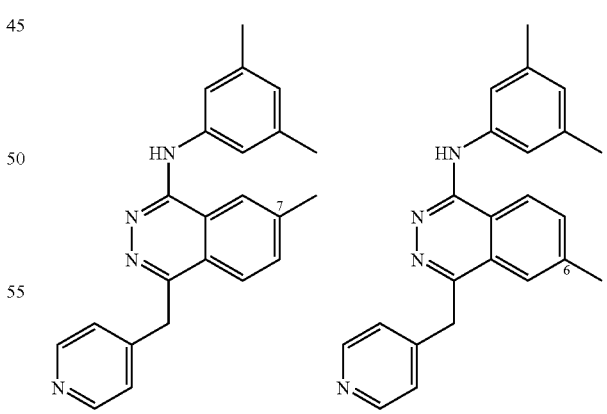

The starting material is prepared as follows:

17a: 3-Hydroxy-5-methyl-2-(pyridin-4-yl)-indene-1-one

A mixture of 47.5 g (293 mmol) 4-methyl-phthalic anhydride and 28.6 ml (293 mmol) 4-picoline is heated to 165°

C. for 18 h. The resulting material is stirred in 190 ml of boiling ethanol, filtered and washed with ethanol and diethyl ether, yielding the title compound: An. calc. ($C_{15}H_{11}NO_2$) C, 75.94%; H, 4.67%; N, 5.90%; O, 13.49%; An. meas. C, 75.60%; H, 4.64%; N, 6.02%; O, 13.60%; $^1$H NMR (DMSO-$d_6$) δ 8.70 (d, 2H), 8.14 (d, 2H), 7.34 (m, 2H), 7.29 (s, 1H), 2.38 (s, 3H); FAB MS (M+H)$^+$=238.

17b: 4-(Pyridin-4-yl)methyl-6-methyl-2.H.-phthalazin-1-one and 4-(pyridin-4-yl)methyl-7-methyl-2.H.-phthalazin-1-one Heating of a mixture of 7.0 g (29.5 mol) 3-hydroxy-5-methyl-2-(pyridin-4-yl)-indene-1-one in 25 ml of hydrazine monohydrate to 110° C. during 16 h gives a brown oil from which a precipitate is formed during cooling to RT. Filtration and washing with water and diethyl ether affords a –1:1 mixture of the regio isomers: An. calc. ($C_{15}H_{13}N_3O.16$ $H_2O$) C 70.88%, H 5.28%; N, 16.53%; O, 7.30%; $H_2O$, 1.13%; An meas. C, 70.99%; H, 5.43%; N, 16.78%; O, 6.99%; $H_2O$, 1.16%; $^1$H NMR (DMSO-$d_6$) δ 12.5 (sb, HN), 8.45 (d, 2H), 8.14 (d, $HC^{6-Me}$), 8.06 (s, $HC^{7-Me}$), 7.80 (d, $HC^{7-Me}$; NOE on signals at 7.69, 7.29 and 4.30 ppm), 7.74 (s, $HC^{6-Me}$; NOE on signals at 7.31, 4.31 and 2.46 ppm), 7.69 (d, $HC^{7-Me}$), 7.64 (d, $HC^{6-Me}$), 7.31 (d, $2HC^{6-Me}$), 7.29 (d, $2HC^{7-Me}$), 4.31 (s, $H_2C^{6-Me}$), 4.30 (s, $H_2C^{7-Me}$), 2.47 (s, $H_3C^{7-Me}$), 2.46 (s, $H_3C^{6-Me}$); FAB MS (M+H)$^+$=252.

17c

1-Chloro-4-(4-pyridylmethyl)-6-methyl-phthalazine and 1-chloro-4-(4-pyridyl-methyl)-7-methyl-phthalazine Preparation from a –1:1 mixture of 4-(pyridin-4-yl)methyl-6-methyl-2.H.-phthalazin-1-one and 4-(pyridin-4-yl)methyl-7-methyl-2.H.-phthalazin-1-one as described in expl. 8d) yields the title product as a mixture of regioisomers: $^1$H NMR (DMSO-$d_6$) δ 8.45 (m, 2H), 8.20, 8.09 and 7.95 (m, s, m, 3H), 7.34 and 7.30 (2d, 2H), 4.72 (s, 2H), 2.60 and 2.59 (2s, 3H); FAB MS (M+H)$^+$=270.

Example 18

In analogy to the procedure described in Example 17, the following compounds are obtained (some are isolated as salt; salts are marked in the table):

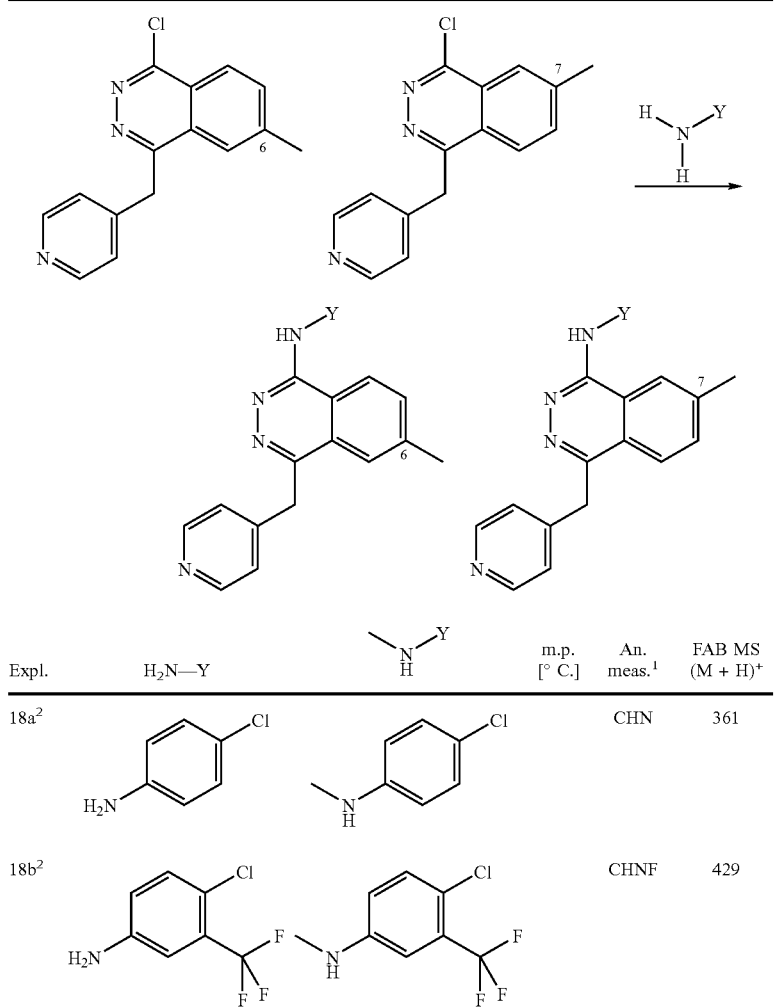

| Expl. | H$_2$N—Y | ![HN-Y structure] | m.p. [° C.] | An. meas.$^1$ | FAB MS (M + H)$^+$ |
|---|---|---|---|---|---|
| 18a$^2$ | 4-chloroaniline (H$_2$N-C$_6$H$_4$-Cl) | N-methyl-4-chloroaniline | | CHN | 361 |
| 18b$^2$ | 5-amino-2-chloro-benzotrifluoride | corresponding secondary amine | | CHNF | 429 |

| Expl. | H₂N—Y | ![structure] | m.p. [°C.] | An. meas.¹ | FAB MS (M + H)⁺ |
|---|---|---|---|---|---|
| 18c | 3-bromo-5-(trifluoromethyl)aniline | corresponding NH derivative | | CHNBrF | 473/475 |
| 18d | 4-bromo-3-(trifluoromethyl)aniline | corresponding NH derivative | | | 473/475 |
| 18e | 3-iodo-4-methylaniline | corresponding NH derivative | | | 467 |
| 18f | 4-chloro-3-methoxyaniline | corresponding NH derivative | | | 391 |

¹within ±0.4% of the calculated values
²dihydrochloride

Example 19

Trans and cis 1-(4-tert-Butylcyclohexyl-amino)-4-(4-pyridyl-methyl)-phthalazine A mixture of 1.0 g (3.91 mmol) 1-chloro-4-(4-pyridylmethyl)phthalazine (Example 67.A1 in WO 98/35958) and 1.82 g (11.7 mmol) 4-tert-butylcyclohexylamine (trans-/cis-mixture) is stirred overnight at 120° C. The cooled reaction mixture is then distributed between ethyl acetate and saturated aqueous sodium hydrogencarbonate solution. The organic phase is washed with water and brine, dried (MgSO₄) and evaporated and the residue purified on silica gel by flash chromatography using dichloromethane/methanol (9:1) yielding the title compound as a trans-/cis-mixture: FAB MS (M+H)$^+$=375. Separation of the isomers by reversed phase medium pressure chromatography (CH$_3$CN/H$_2$O/trace of TFA) gives the cis-isomer (m.p. 64-65° C.) followed by the trans-isomer (m.p. 132-134° C.).

Example 20

Analogously to Example 19, the following compounds can be obtained (some are isolated as salt; salts are marked in the table):

| Expl. | H$_2$N—Y | ![NH-Y structure] | m.p. [° C.] | An. meas.[1] | FAB MS (M + H)$^+$ |
|---|---|---|---|---|---|
| 20a | 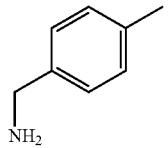 | 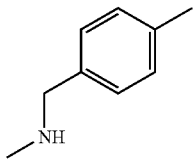 | | CHN | 341 |
| 20b | 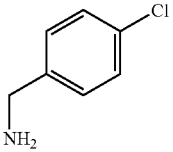 | 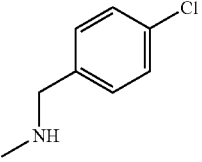 | | CHN | 361 |
| 20c | 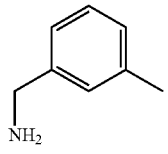 | 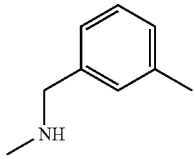 | | CHN | 341 |
| 20d | 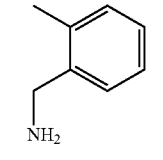 | 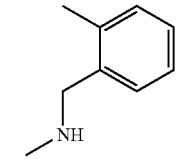 | 180-181 | CHN | 341 |
| 20e | 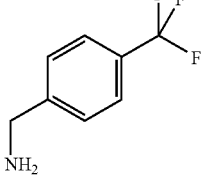 | 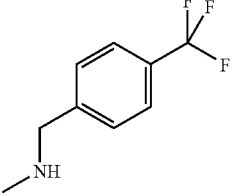 | 145 | CHNF | 395 |

-continued

| Expl. | H₂N—Y | ![structure] CH₃-NH-Y | m.p. [° C.] | An. meas.¹ | FAB MS (M + H)⁺ |
|---|---|---|---|---|---|
| 20f | 2-Cl-C₆H₄-CH₂-NH₂ | 2-Cl-C₆H₄-CH₂-NH-CH₃ |  | CHNCl | 361 |
| 20g | 3-CF₃-C₆H₄-CH₂-NH₂ | 3-CF₃-C₆H₄-CH₂-NH-CH₃ | 86 | CHNF | 395 |
| 20h | 3-Cl-C₆H₄-CH₂-NH₂ | 3-Cl-C₆H₄-CH₂-NH-CH₃ |  |  | 361 |
| 20i² | 3-Et-C₆H₄-CH₂-NH₂ | 3-Et-C₆H₄-CH₂-NH-CH₃ |  |  | 355 |
| 20j | 3-F-5-CF₃-C₆H₃-CH₂-NH₂ | 3-F-5-CF₃-C₆H₃-CH₂-NH-CH₃ | 148 | CHNF | 413 |
| 20k² | 4-Et-C₆H₄-CH₂-NH₂ | 4-Et-C₆H₄-CH₂-NH-CH₃ |  | CHNO | 355 |

-continued
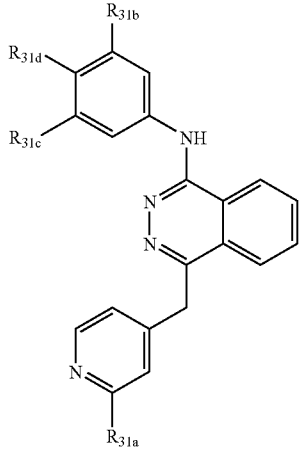
| Expl. | H₂N—Y |  | m.p. [° C.] | An. meas.[1] | FAB MS (M + H)⁺ |
|---|---|---|---|---|---|
| 20l | 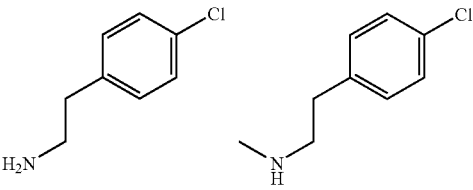 | 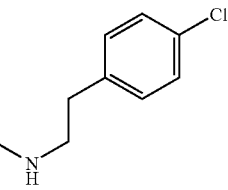 |  | CHNCl | 375 |
| 20m | 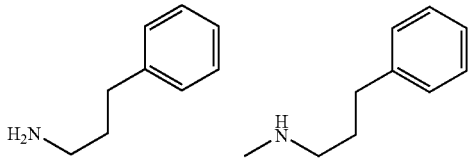 | 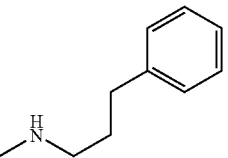 | 100-103 | CHN | 355 |
| 20n | 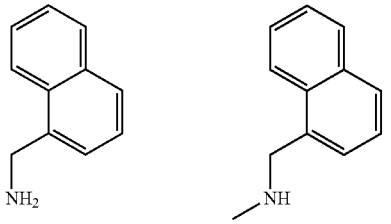 | 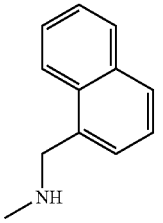 | 104-106 | CHN | 377 |
| 20o[3] | 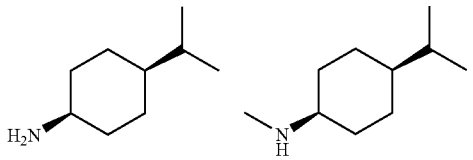 | 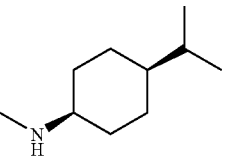 | 165-167 | CHN | 361 |
| 20p[3] | 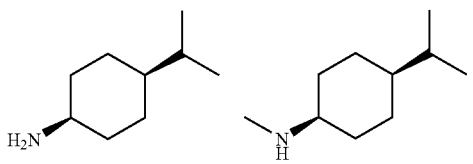 | 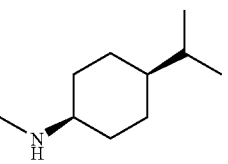 | 139-140 | CHN |  |

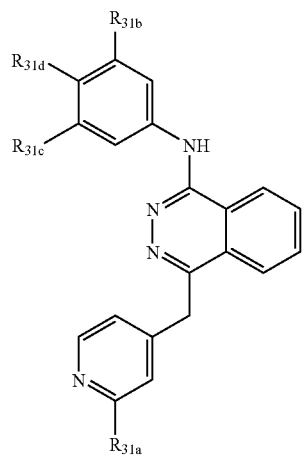
| Expl. | H₂N—Y | | m.p. [° C.] | An. meas.[1] | FAB MS (M + H)+ |
|---|---|---|---|---|---|
| 20p[3] | | | 181-182 | CHN | 347 |
| 20q[3] | | | | | 347 |
[1] within ±0.4% of the calculated values
[2] succinate salt
[3] preparation see: Arzneim. Forsch. 19 (1969), 140
Example 21
[4-(4-Chloranilino)phthalazin-1-yl](pyridin-4-yl) ketone
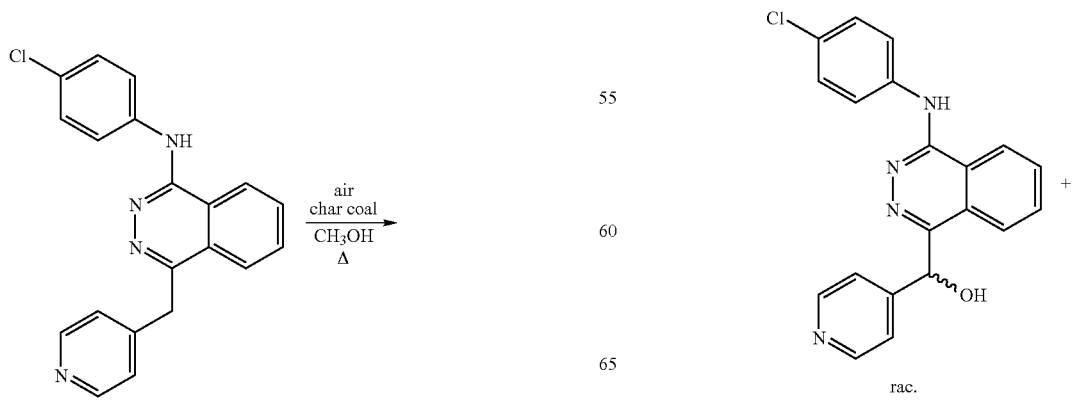

-continued

Heating of a mixture of 1-(4-chloranilino)-4-(4-pyridyl-methyl)-phthalazine (Example 4 in WO 98/35958) and charcoal in boiling methanol for about 7 days in an open vessel leads to partial oxidation of the methylen-bridge of 1-(4-chloranilino)-4-(4-pyridylmethyl)-phthalazine. After cooling to RT, unchanged 1-(4-chloranilino)-4-(4-pyridylmethyl)-phthalazine crystallizes out and can be filtered off. Chromatography ($SiO_2$; dichloromethane/methanol 98:2) of the concentrated filtrate then leads to [4-(4chloranilino) phthalazin-1-yl](pyridin-4-yl)ketone and rac. [4-(4-chloranilino)phthalazin-1-yl](pyridin-4-yl)methanol (see Expl. 78 in WO 98/35958). [4-(4-Chloranilino)phthalazin-1-yl] (pyridin-4-yl)ketone: $^1$H NMR (DMSO-$d_6$) δ 9.88 (bs, 1H, HN), 8.79 (d, 2H, pyridine), 8.71 (d, 1H), 8.63 (d, 1H), 8.07 (m, 2H), 7.97 (d, 2H, chloranilino), 7.77 (d, 2H, pyridine), 7.45 (d, 2H, chloranilino); IR (KBr): 3287, 3139, 3066, 1667 (CO), 1620 cm$^{-1}$; FAB MS (M+H)$^+$=361.

rac[4-(4-Chloranilino)phthalazin-1-yl](pyridin-4-yl) methanol: m.p. 197-197.5 dec; $^1$H NMR (DMSO-$d_6$) δ 9.32 (bs, 1H, HN), 8.57 (d, 1H), 8.49 (d, 2H, pyridine), 8.22 (d, 1H), 8.00 (d, 2H, chloranilino), 7.93 (m, 1H), 7.84 (m, 1H), 7.41 (d, 2H, pyridine); 7.40 (d, 2H, chloranilino), 6.77 (d, 1H, HO), 6.30 (d, 1H, HC—OH); IR (KBr): 3386 (OH), 3122, 2852, 1619, 1600, 1521, 1493, 1406 cm$^{-1}$; FAB MS (M+H)$^+$=363.

Example 22 rac[4-(4-Chloranilino)phthalazin-1-yl](1-oxypyridin-4-yl)methanol

To a solution of 400 mg (1.1 mmol) rac[4-(4-chloranilino) phthalazin-1-yl](pyridin-4-yl)methanol (Example 78 in WO 98/35958) in 20 ml dichloromethane and 20 ml methanol, a solution of 1.6 g (2.6 mmol) OXONE® (potassium peroxymonosulphate) in 40 ml water is added. The biphasic mixture is stirred at RT overnight and then concentrated in vacuo. After re-dissolving the resulting residue in 50 ml dichloromethane and 20 ml water, the aqueous layer is separated off and extracted twice with dichloromethane. The organic phases are washed twice with water and discarded. The aqueous phases (pH=1-2) are made basic by addition of 1 N NaOH yielding a precipitation, which is filtered off and washed with water. Chromatography ($SiO_2$; dichloromethane to dichloromethane/methanol 99:1, then 97:3, then 95:5, then 9:1) gives the crude compound. Reversed phase MPLC (Merck Lichroprep RP-18; water/acetonitril+ TFA), partial concentration, addition of $NaHCO_3$, filtration of the precipitate and washing with water finally affords the title compound: $^1$H NMR (DMSO-$d_6$) δ 9.39 (s, HN), 8.60 (d, 1H), 8.26 (d, 1H), 8.15 (d, 2H), 8.00 (d, 2H), 8.00 (t, 1H), 7.91 (t, 1H), 7.40 (d, 4H), 6.80 (d, HO), 6.30 (d, 1H); $^{13}$C NMR (DMSO-$d_6$) 153.9, 152.8, 141.6, 140.0, 138.7, 132.0, 128.7, 126.1, 125.7, 125.8, 124.4, 123.2, 122.7, 119.5, 73.3; FAB MS (M+H)$^+$=379.

Example 23

1-(3-Bromo-5-trifluoromethyl-anilino)-4-(2-methylpyridin-4-yl-methyl)-phthalazine A mixture of 200 mg (0.74 mmol) 1-chloro-4-(2-methylpyridin-4-ylmethyl)-phthalazine, 187 mg (0.78 mmol) 3-bromo-5-trifluormethylaniline, 3 ml ethanol and 0.18 ml HCl (4 N in dioxane) is heated for 90 h to 60° C. At RT, 8 ml of water and 0.3 ml of a 25-% $NH_3$-solution are added. Then the precipitating solution is diluted in ethyl acetate and water, and the aqueous phase is separated off and extracted twice with ethyl acetate. The organic layers are washed with water and brine, dried ($Na_2SO_4$) and partially concentrated. Upon addition of DIPE and hexane, the title compound crystallizes: m.p. 184-185° C.; An. calc. ($C_{22}H_{16}N_4BrF_3$) C, 55.83%; H, 3.41%; N, 11.84%; Br, 16.88%; F, 12.04%; An. meas. C, 55.9%; H, 3.5%; N, 11.4%; Br, 16.8%; F, 12.0%; $^1$H NMR (DMSO-$d_6$) δ 9.62 (s, HN), 8.71 (s, 1H), 8.62 (d, 1H), 8.46 (s, 1H), 8.31 (d, 1H), 8.15 (d, 1H), 8.0 (m, 2H), 7.56 (s, 1H), 7.19 (s, 1H), 7.12 (d, 1H), 4.58 (s, $H_2$C), 2.38 (s, $H_3$C); MS (M+H)$^+$=473/475.

The starting material is prepared as follows:

23a: 3-(2-Methyl-pyridin-4-ylmethylene)-3.H.-isobenzofuran-1-one

To an ice-cooled solution of 2.3 g (19 mmol) 2-methyl-pyridin-4carbaldehyde (*J. Med. Chem.* 1996, 39, 3929) in 40 ml THF are added 6.0 g (14 mMol) 1,3-dihydro-3-oxo-1-isobenzofuranyl-triphenyl-phosphonium chloride (*J. Organomet. Chem.* 1972, 42, 391) and 2.65 ml (19 mMol) $Et_3N$. After 2.5 h, the precipitate is filtered off, washed with ethyl acetate and discarded. After the addition of 13 g of $SiO_2$, the filtrate is concentrated and the resulting powder put on top of a silica-gel column. Eluation with toluene/acetone 3:2 affords the title compound: FAB MS (M+H)$^+$=238.

23b: 4-(2-Methyl-pyridin-4-ylmethyl)-2.H.-phthalazin-1-one

Heating of a mixture of 2.55 g (10.7 mol) 3-(2-methyl-pyridin-4-ylmethylene)-3.H.-isobenzofuran-1-one, 40 ml of hydrazine monohydrate and 40 ml THF to 80° C. during 28 h gives a clear solution. After diluting with water and ethyl acetate, the aqueous layer is separated off and extracted twice with ethyl acetate and discarded. The organic phases are washed with brine, extracted with 2 portions of 1 N HCl and discarded, too. The acidic layers are made basic by the addition of 1 N NaOH, extracted 3× with ethyl acetate and discarded. The last ethyl acetate phases are washed with water and brine, dried ($Na_2SO_4$) and partially concentrated. After addition of hexane, the title compound crystallizes: m.p. 195-196° C.; FAB MS (M+H)$^+$=252.

23c: 1-Chloro-4-(2-methylpyridin-4-ylmethyl)-phthalazine

Preparation from 4-(2-methyl-pyridin-4-ylmethyl)-2.H.-phthalazin-1-one analogously as described in expl. 8d) yields the title product: m.p. 122-123° C.; $^1$H NMR (DMSO-$d_6$) δ 8.34 (m, 3H), 8.14 (m, 2H), 7.19 (s, 1H), 7.13 (d, 1H), 4.71 (s, $H_2$C), 2.38 (s, $H_3$C); FAB MS (M+H)$^+$=270.

Example 24
In analogy to the procedure described in Example 23, the following compounds are obtained
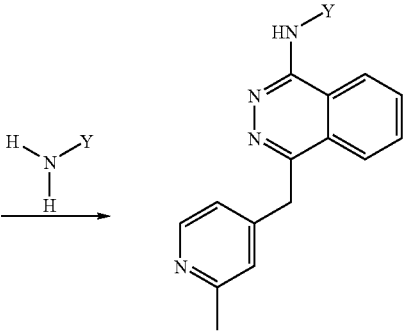
| Expl. | H$_2$N—Y | NH—CH$_3$ | m.p. [° C.] | An. meas.[1] | FAB MS (M + H)$^+$ |
|---|---|---|---|---|---|
| 24a | 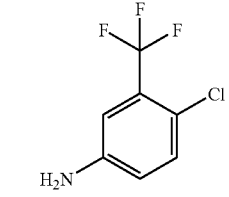 | 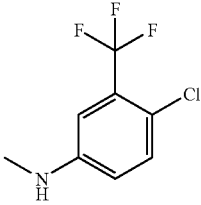 | 186-187 | | 429 |
| 24b | 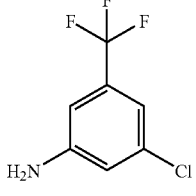 | 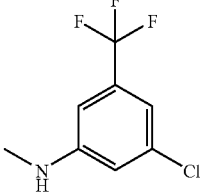 | 194-195 | | 429 |
| 24c | 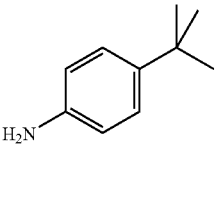 | 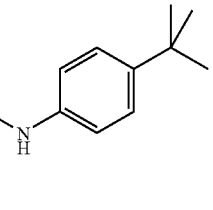 | 188-189 | | 383 |
| 24d | 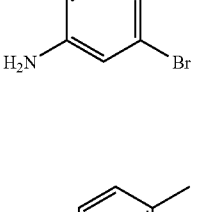 | 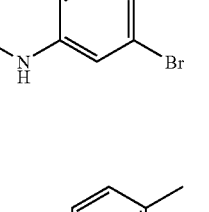 | 180-181 | CHNBr | 433/435 |
| 24e | 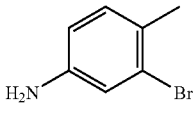 | 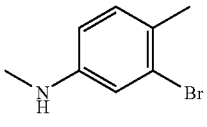 | 185-186 | CHNBr | 419/421 |

-continued

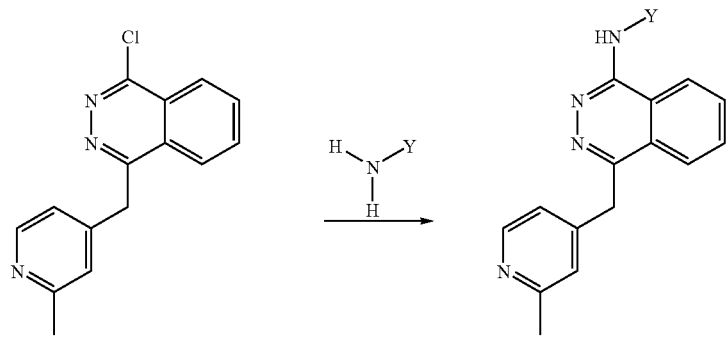

| Expl. | H₂N—Y | ![N(Y)H structure] | m.p. [° C.] | An. meas.[1] | FAB MS (M + H)⁺ |
|---|---|---|---|---|---|
| 24f | | | 155-156 | | 462 |
| 24g | | | | | |

[1] within ±0.4% of the calculated values

Example 25 rac. 1-(4-Chlor-anilino)-4-(pyridin-4-yl-fluorm-ethyl)-phthalazine

Under $N_2$-atmosphere, 7.02 ml (4.65 mmol; 15% in toluene) of potassium bis(trimethylsilyl)-amide are dissolved in 78 ml THF and then cooled to −78° C. A solution of 537.5 mg (1.55 mmol) of 1-(4-chlor-anilino)-4-(pyridin-4-yl-methyl)-phthalazine (see WO 98/35958) in 30 ml THF is added dropwise. The resulting black solution is stirred for additional 30 min, then 1.00 g (4.65 mmol) of 2-fluoro-3,3-dimethyl-2,3-dihydro-1,2-benzisothiazole (Fluka; Buchs, Switzerland) in 30 ml THF are added slowly. The reaction solution slowly turns to yellow-orange. After 3 h at −78° C., a solution of 1 ml acetic acid in 5 ml of THF is added. The reaction mixture is poured into a diluted $NaHCO_3$-solution and extracted three times with ethyl acetate. The organic layers are washed with 2 portions of water and brine, dried ($Na_2SO_4$) and concentrated. Chromatography ($SiO_2$; EtOAc/dichloromethane 2:1 to EtOAc to EtOAc/EtOH 9:1 to 4:1) and crystallization from acetonitrile/acetone finally gave the title compound: $^1$H NMR (DMSO-$d_6$) δ 9.50 (s, HN), 8.65 (d, 1H), 8.61 (d, 2H), 8.16 (d, 1H), 8.03 (t, 1H), 7.99 (t, 1H), 7.96 (d, 2H), 7.43 (d, 2H), 7.40 (d, 2H), 7.34 (s, 1H); $^{19}$F NMR (DMSO-$d_6$) δ −50.7; FAB-MS (M+H)⁺= 365.

Example 26

1-(4-Chlorphenyl-methylamino)-4-(2-methylpyridin-4-yl-methyl)-phthalazine can be prepared by analogy with the above methods

Example 27

1-(4-Ethyl-3-bromoanilino)-4-[(2-(6-methylpyridin-3-yl)ethyl]phthalazine hydrochloride A solution of 100 mg (0.35 mmol) 1-chloro-4-[2-(6-methylpyridin-3-yl)ethyl]phthalazine, 73 mg (0.35 mmol) 3-bromo-4-ethyl-aniline (expl. 14q.1) in 3 ml ethanol and 88 μl 4 N HCl in dioxane is stirred for 6 h at 85° C. The resulting cooled suspension is filtered and washed with ethanol: m.p. 164-167° C.; $^1$H-NMR (DMSO-$d_6$) 8.92 (d, 1H), 8.77 (s, 1H), 8.54 (d, 1H), 8.38 (d, 1H), 8.24 (m, 2H), 8.00 (s, 1H), 7.79 (d, 1H), 7.62 (d, 1H), 7.45 (d, 1H), 3.65 (t, 2H), 3.25 (t, 2H), 2.72 (q, 2H), 2.67 (s, 3H), 1.19 (t, 3H); FAB-MS (M+H)⁺=447/449.

The starting material is prepared as follows:

27a) Triphenyl-(6-methylpyridin-3-yl-methyl)phosphonium chloride

Prepared from 5-chlormethyl-2-methyl-pyridine (*Arch. Pharm.* 1975, 308, 359) as described in expl. 1a): $^1$H-NMR (DMSO-$d_6$) inter alia 5.24 (d, J=15.6 Hz, $H_2$C), 2.38 (s $H_3$C).

27b) E/Z-4-[2-(6-Methylpyridin-3-yl)vinyl]phthalazin-1(2H)-one

Prepared by Wittig reaction of triphenyl-(6-methylpyridin-3-yl-methyl)phosphonium chloride and phthalazin-1(2H)-one-4-carbaldehyde as described in expl. 4d): HPLC$_{5-40}$ $t_R$=11.7/12.2.

27c) 4-[2-(6-Methylpyridin-3-yl)ethyl]phthalazin-1(2H)-one

Hydrogenation of 250 mg (0.95 mmol) E/Z-4-[2-(6-methylpyridin-3-yl)vinyl]phthalazin-1(2H-one in 10 ml methanol in the presence of 150 mg Pd/C 10%, filtration and evaporation yields the title compound: $^1$H-NMR (DMSO-$d_6$) 12.48 (s, HN), 8.32 (s, 1H), 8.24 (d, 1H), 8.04 (d, 1H), 7.92 (t, 1H), 7.83 (t, 1H), 7.57 (m, 1H), 7.14 (d, 1H), 3.21 (t, 2H), 2.98 (t, 2H), 2.39 (s $H_3$C).

27d) 1-Chloro-4-[2-(6-methylpyridin-3-yl)ethyl]phthalazine

Under $N_2$-atmosphere, 217 mg (0.818 mmol) 4-[2-(6-methylpyridin-3-yl)ethyl]phthalazin-1(2H)-one in 3.3 ml acetonitrile is mixed with 187 µl (2.04 mmol) phosphoryl chloride and 0.41 ml 4 N HCl in dioxane and stirred for 9 h at 60° C. After cooling to RT, 2.6 ml $H_2O$, followed by a solution of 0.5 ml sat. $NH_3$ and 5 ml $H_2O$ is added. Immediate extraction with 3 portions of EtOAc, washing of the organic layers with water and brine, drying ($Na_2SO_4$) and evaporation yield the title compound; FAB-MS (M+H)$^+$=284.

Example 28

Trans 1-(4-Isopropyl-cyclohexylamino)-4-[(2-(6-methylpyridin-3-yl)ethyl]phthalazine Prepared as described in expl. 6 from 1-chloro-4-[2-(6-methylpyridin-3-yl)ethyl]phthalazine and trans 4-isopropyl-cyclohexylamine (*Arzneim. Forsch.* 19 (1969), 140): HPLC$_{20-100}$ $t_R$=11.1; FAB-MS (M+H)$^+$=389.

Example 29

1-(3-Brom-4-methyl-anilino)-4-(4-oxypyridyl-methyl)-phthalazine

To a solution of 0.90 g (2.22 mmol) 1-(3-brom-4-methyl-anilino)-4-(4-pyridyl-methyl)-phthalazine (expl. 14h) in 40 ml dichloromethane and 40 ml methanol, a solution of 3.23 g (5.25 mmol) OXONE® (potassium peroxymonosulphate) in 40 ml water and 40 ml methanol is added. After stirring for 5 h at RT, $Na_2CO_3$ solution is added to the biphasic mixture. The aqueous layer is separated off and extracted twice with EtOAc. The organic phases are washed twice with water and brine, dried (MgSO$_4$) and concentrated. Reversed phase MPLC (Merck Lichroprep RP-18; water/acetonitril+TFA) of a solution of the residue in TFA, partial concentration, addition of NaHCO$_3$, extraction with EtOAc and concentration finally affords the title compound: $^1$H NMR (DMSO-$d_6$) δ 9.22 (s, HN), 8.59 (d, 1H), 8.37 (d, 1H), 8.13 (d, 1H), 8.10 (d, 2H), 7.94 (m, 2H), 7.83 (dd, 1H), 7.3 (m, 3H), 4.55 (s, 2H), 2.32 (s, $H_3$C); FAB MS (M+H)$^+$=421/423.

Example 30

[4-(3-Brom-4-methyl-anilino)phthalazin-1-yl](pyridin-4-yl)ketone and rac. [4-(3-brom-4-methyl-anilino)phthalazin-1-yl](pyridin-4-yl)methanol A mixture of 1.22 g (3 mmol) 1-(3-brom-4-methyl-anilino)-4-(4-pyridyl-methyl)-phthalazine (expl. 14h) and 336 mg (3 mmol) potassium-tert.butylate in 10 ml DMSO is stirred in an open vessel for 10 days at RT. Then the yellow mixture is diluted with EtOAc and water, the aqueous layer separated off and extracted twice with EtOAc. The organic phases are washed twice with water and brine, dried ($Na_2SO_4$) and partly concentrated. After adding 10 g of $SiO_2$, the residue is dried in vacuo and the resulting powder put on top of a $SiO_2$-column. Eluation with dichloromethane/EtOAc (5:1→1:1→EtOAc) yields [4-(3-brom-4-methyl-anilino)phthalazin-1-yl](pyridin-4-yl)ketone (A) followed by [4-(3-brom-4-methyl-anilino)phthalazin-1-yl](pyridin-4-yl)methanol (B). A: m.p. 249-250° C.; FAB MS (M+H)$^+$=419/421. B: m.p. 240° C.; FAB MS (M+H)$^+$=421/423.

Example 31

In analogy to the methods described in WO 98/35958, especially as described in the Examples and on pages 22 and 23 under process c), the following compounds are prepared:

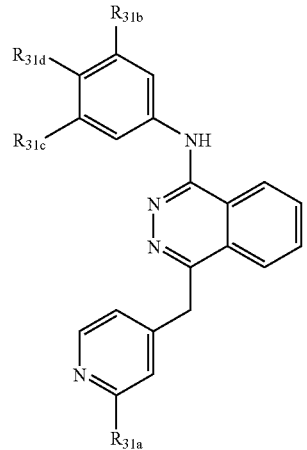

| Example | $R_{31a}$ | $R_{31b}$ | $R_{31c}$ | $R_{31d}$ |
|---|---|---|---|---|
| 31A | F | CF$_3$ | Cl | H |
| 31B | OMe | H | Br | Me |
| 31C | OMe | Cl | CF$_3$ | H |
| 31D | OMe | H | Me | i-Pr |
| 31E | Cl | H | Br | Et |

Example 32

Rat Adjuvant Arthritis Model

The rat adjuvant arthritis model is used to test the anti-arthritic activity of the compound of Example 1 of WO 98/35958, 1-(4-chloroanilino)-4-(4-pyridylmethyl)phthalazine dihydrochloride. The therapeutic dosing schedule with start of treatment at day 15 after induction of arthritis is used.

Method: Male Wistar rats (5 rats per group, weight about 200 g; Iffa Credo, France) are injected i.d. (intra-dermally) at the base of the tail with 0.1 ml of mineral oil containing 0.6 mg of lyophilized heat-killed *Mycobacterium tuberculosis*. The rats are treated with the test compound (3, 10 or 30 mg/kg p.o. s.i.d. (=once a day), or vehicle (water) from day 15 to day 22 (therapeutic dosing schedule). At the end of the experiment, the swelling of the tarsal joints is measured by means of a mico-calliper. Percentage inhibition of paw swelling is calculated by reference to vehicle treated arthritic animals (0% inhibition) and vehicle treated normal animals (100% inhibition).

The test compound shows dose-related inhibition of paw swelling in the therapeutic rat adjuvant arthritis model (dosing for 7 days, from day 15), as can be seen in the following table (as comparison, SDZ 115-155=DUP697, is used):

| Compound | Dose (mg/kg) | % inhibition of swelling |
|---|---|---|
| 115–155 | 3 | 53.8 ± 2.7 |
| 1-(4-Chloroanilino)-4-(4-pyridylmethyl)-phthalazine dihydrochloride | 3 | 0.8 ± 4.0 |
| 1-(4-Chloroanilino)-4-(4-pyridylmethyl)-phthalazine dihydrochloride | 10 | 12.4 ± 5.0 |
| 1-(4-Chloroanilino)-4-(4-pyridylmethyl)-phthalazine dihydrochloride | 30 | 37.0 ± 2.3 |

Example 33

Rat Inflammatory Hyperalgesia Model

Since the title compound of Example 1 of WO 98/35958, 1-(4-chloroanilino)-4-(4-pyridyl-methyl)phthalazine dihydrochloride, is observed to reduce the overall discomfort experienced by rats while being held for oral dosing in the adjuvant arthritis model, it is also tested in a simple model of nociception (pain). In this model, the hyperalgesia caused by an intra-planar yeast injection is measured by applying increased pressure to the foot until the animal vocalizes or withdraws its foot from the applied pressure pad. The model is sensitive to COX inhibitors, and diclofenac at 3 mg/kg is used as a positive control.

Method: The baseline pressure required to induce vocalization or withdrawal of the paw of male Sprague Dawley rats (5 rats per group; weight approximately 180 g, Iffa Credo, France) is measured (2 hours before treatment), followed by an intra-planar injection of 100 µl of a 20% yeast suspension in water in the hind paw. The rats are treated orally with the test compound (3, 10 or 30 mg/kg), diclofenac (3 mg/kg) or vehicle (saline) p.o. 2 hours later (time point 0 hours), and the pressure test is repeated 1 and 2 hours after dosing. The pressure required to induce vocalisation or paw withdrawal of the compound-treated rats at these time points is compared to that of vehicle-treated animals. Pressure is measured with the standard apparatus from Ugo Basile, Italy, for the paw pressure test (Randall-Selitto).

The test compound inhibits paw hyperalgesia noth at 1 and 2 hours after dosing in the Randall-Selitto test at the 30 mg/kg p.o. dose, demonstrating that the compound has analgesic activity.

The detailed results can be deduced from the following table:

| Compound | Dose (mg/kg) | % inhibition of swelling |
|---|---|---|
| Vehicle | 0 | 239 ± 13 |
| Diclofenac | 3 | 323 ± 14 |
| 1-(4-Chloroanilino)-4-(4-pyridylmethyl)-phthalazine dihydrochloride | 3 | 255 ± 15 |
| 1-(4-Chloroanilino)-4-(4-pyridylmethyl)-phthalazine dihydrochloride | 10 | 254 ± 3 |
| 1-(4-Chloroanilino)-4-(4-pyridylmethyl)-phthalazine dihydrochloride | 30 | 357 ± 23 |

What is claimed is:

1. A method of treating leukemias by inhibiting VEGF-receptor tyrosine kinase activity comprising administering a compound of formula I, $$\text{(I)}$$

wherein
r is 0 to 2,
n is 0 to 3
$R_1$ and $R_2$
a) are independently in each case a lower alkyl;
b) together form a bridge of subformula I*, $$\text{(I*)}$$

wherein a bond characterizing said bridge is achieved via two terminal C atoms of $R_1$ and $R_2$ and
m is 0 to 4, or
c) together form a bridge of subformula I, $$\text{(I)}$$

wherein one or two of the ring members $T_1$, $T_2$, $T_3$ and $T_4$ are nitrogen, and the others are in each case CH, and the bond is achieved via atoms $T_1$ and $T_4$;

G is —C(=O)—, —CHF—, —CF₂—, lower alkylene, C₂-C₆alkenylene, lower alkylene or C₃-C₆alkenylene substituted by acyloxy or hydroxy, —CH₂—O—, —CH₂—S—, —CH₂—NH—, —CH₂—O—CH₂—, —CH₂—S—CH₂—, oxa (—O—), thia (—S—), imino (—NH—), or —CH₂—NH—CH₂—;

A, B, D, E and T are independently N or CH subject to the proviso that at least one and not more than three of these radicals are N;

Q is lower alkyl, lower alkoxy, or halogen;

$R_a$ and $R_a'$ are each independently H or lower alkyl;

X is imino, oxa or thia;

Y is hydrogen, aryl, heteroaryl, or unsubstituted or substituted cycloalkyl; and Z is mono- or disubstituted amino, halogen, alkyl, substituted alkyl, hydroxy, etherified or esterified hydroxy, nitro, cyano, carboxy, esterified carboxy, alkanoyl, carbamoyl, N- mono- or N,N-disubstituted carbamoyl, amidino, guanidino, mercapto, sulfo, phenylthio, phenyl lower alkylthio, alkylphenylthio, phenylsulfinyl, phenyl-lower alkylsulfinyl, alkylphenylsulfinyl, phenylsulfonyl, phenyl-lower alkylsulfonyl, alkylphenylsulfonyl, or selected from the group consisting of ureido, halo-lower alkylthio, halo-lower alkansulfonyl, pyrazolyl, lower-alkyl pyrazolyl and C₂-C₇alkenyl;
wherein—if more than 1 radical Z(m≧2) is present—the substituents Z are selected independently from each other;
and wherein the bonds characterized in subformula I* by a wavy line are either single or double bonds;
or an N-oxide of said compound, wherein 1 or more N atoms carry an oxygen atom; or a pharmaceutically acceptable salt thereof.

2. The method according to claim 1, where in the compound of the formula I, or the salt thereof,
r is 0 to 2,
n is 0 to 3
R₁ and R₂
a) are independently in each case a lower alkyl;
b) together form a bridge of subformula I*,
wherein said bond is achieved via the two terminal C atoms and
m is 0 to 4, or
c) together form a bridge of subformula I**,
wherein one or two of the ring members T₁, T₂, T₃ and T₄ are nitrogen, and the others are in each case CH, and the bond is achieved via atoms T₁ and T₄;
G is —C(=O)—, —CHF—, —CF₂—, lower alkylene, C₂-C₆alkenylene, lower alkylene or C₃-C₆alkenylene substituted by acyloxy or hydroxy, —CH₂—O—, —CH₂—S—, —CH₂—NH—, —CH₂—O—CH₂—, —CH₂—S—CH₂—, —CH₂—NH—CH₂—, oxa (—O—), thia (—S—) or imino (—NH—);
A, B, D, E and T are independently N or CH subject to the proviso that at least one and not more than three of these radicals are N;
Q is lower alkyl;
$R_a$ and $R_a'$ are each independently H or lower alkyl;
X is imino, oxa, or thia;
Y is hydrogen, aryl, heteroaryl, or unsubstituted or substituted cycloalkyl; and
Z is mono- or disubstituted amino, halogen, alkyl, substituted alkyl, hydroxy, etherified or esterified hydroxy, nitro, cyano, carboxy, esterified carboxy, alkanoyl, carbamoyl, N-mono- or N,N-disubstituted carbamoyl, amidino, guanidino, mercapto, sulfo, phenylthio, phenyl lower alkylthio, alkylphenylthio, phenylsulfinyl, phenyl-lower alkylsulfinyl, alkylphenylsulfinyl, phenylsulfonyl, phenyl-lower alkylsulfonyl, alkylphenylsulfonyl, or selected from the group consisting of ureido, halo-lower alkylthio, halo-lower alkansulfonyl, pyrazolyl, lower-alkyl pyrazolyl and C₂-C₇alkenyl;
wherein—if more than 1 radical Z (m≧2) is present—the substituents Z are selected independently from each other;
and wherein the bonds characterized in subformula I* by a wavy line are either single or double bonds;
or an N-oxide of the defined compound, wherein 1 or more N atoms carry an oxygen atom.

3. The method according to claim 1, where in the compound of the formula I, or the salt thereof,
r is 0 to 2,
n is 0 to 2,
m is 0 to 4,
R₁ and R₂
(i) are lower alkyl, or
together form a bridge of subformula I*, wherein a bond characterizing said bridge is achieved via two terminal C atoms of R¹ and R²,
(iii) together form a bridge of subformula I**,
wherein one or two of the ring members T₁, T₂, T₃ and T₄ are nitrogen, and the others are in each case CH, and the binding is achieved via T₁ and T₄;
A, B, D, and E are, independently of one another, N or CH, with the stipulation that not more than 2 of these radicals are N;
T is nitrogen;
G is lower alkylene, lower alkylene substituted by acyloxy or hydroxy, —CH₂—O—, —CH₂—S—, —CH₂—NH—, oxa (—O—), thia (—S—), or imino (—NH—);
Q is lower alkyl;
$R_a$ and $R_a'$ are each independently H or lower alkyl;
X is imino, oxa or thia;
Y is aryl, pyridyl, or unsubstituted or substituted cycloalkyl; and
Z is mono- or disubstituted amino, halogen, alkyl, substituted alkyl, hydroxy, etherified or esterified hydroxy, nitro, cyano, carboxy, esterified carboxy, alkanoyl, carbamoyl, N- mono- or N,N-disubstituted carbamoyl, amidino, guanidino, mercapto, sulfo, phenylthio, phenyl lower alkylthio, alkylphenylthio, phenylsulfinyl, phenyl-lower alkylsulfinyl, alkylphenylsulfinyl, phenylsulfonyl, phenyl-lower alkylsulfonyl, or alkylphenylsulfonyl, wherein—if more than 1 radical Z(m=≧2) is present—the substituents Z are are selected independently from one another;
and wherein the bonds characterized, if present, by a wavy line are either single or double bonds;
or an N-oxide of the defined compound, wherein 1 or more N atoms carry an oxygen atom.

4. The method according to claim 1, where the compound of the formula I is selected from the group of compounds consisting of
1-(4-chloroanilino)-4-(4-pyridylmethyl)phthalazine;
[4-(4-chloroanilino)phthalazin-1-yl](pyridin-4-yl)methanol; and
1-(4-chloroanilino)4-[(1-oxypyridin-4-yl)methyl]phthalazine;
or a pharmaceutically acceptable salt thereof.

* * * * *